United States Patent [19]

Estruch et al.

[11] Patent Number: 5,877,012

[45] Date of Patent: Mar. 2, 1999

[54] CLASS OF PROTEINS FOR THE CONTROL OF PLANT PESTS

[75] Inventors: Juan J. Estruch, Durham; Cao-Guo Yu, Carrboro; Gregory W. Warren; Nalini M. Desai, both of Cary, all of N.C.; Michael G. Koziel, Clive, Iowa; Gordon J. Nye, Raleigh, N.C.

[73] Assignee: Novartis Finance Corporation, New York, N.Y.

[21] Appl. No.: 838,219

[22] Filed: Apr. 3, 1997

Related U.S. Application Data

[63] Continuation-in-part of Ser. No. 463,483, Jun. 5, 1995, which is a continuation-in-part of Ser. No. 314,594, Sep. 28, 1994, abandoned, which is a continuation-in-part of Ser. No. 218,018, Mar. 23, 1994, abandoned, which is a continuation-in-part of Ser. No. 37,057, Mar. 25, 1993, abandoned.

[51] Int. Cl.$^6$ .............................. C12N 1/20; C07H 21/04
[52] U.S. Cl. ................................. 435/252.3; 435/252.33; 435/252.31; 435/252.32; 435/252.34; 435/252.35; 435/235.1; 435/254.11; 435/257.2; 435/320.1; 536/23.71; 530/350
[58] Field of Search .......................... 435/252.3, 252.33, 435/252.31, 252.32, 252.34, 252.35, 235.1, 254.11, 257.2, 410, 412, 419; 536/23.71; 530/350

[56] References Cited

U.S. PATENT DOCUMENTS

| 3,632,747 | 1/1972 | Satohiro et al. | 424/93 |
|---|---|---|---|
| 3,651,215 | 3/1972 | Satohiro et al. | 424/93 |
| 4,996,155 | 2/1991 | Sick et al. | 435/252.3 |
| 5,262,323 | 11/1993 | Baird et al. | 435/252.5 |

FOREIGN PATENT DOCUMENTS

| 0498537A2 | 1/1992 | European Pat. Off. . |
|---|---|---|
| 0501650A2 | 2/1992 | European Pat. Off. . |
| WO88/08880 | 11/1988 | WIPO . |
| WO90/13651 | 11/1990 | WIPO . |
| WO91/16432 | 10/1991 | WIPO . |
| WO91/16434 | 10/1991 | WIPO . |
| US94/03131 | 7/1994 | WIPO . |
| WO94/21795 | 9/1994 | WIPO . |

OTHER PUBLICATIONS

Arellano, A., et al., "Evidence of a New *Bacillus thuriengiensis* Toxin Active Against the Australian Sheep Blowfly *Lucilla cuprina*", Proceedings and Abstracts of the 5th International Colloquium on Invertebrate Pathology and Microbial Control, Adelaide, Austrailia, 20–24 Aug., 1990, p. 291.

Chambers et al., Isolation and Characterization of a Novel Isecticidal Crystal Protein Gene from *Bacillus thuringiensis* subsp. aizawai, Journal of Bacteriology, Jul. 1991, 3966–3976.

Beecher, Douglas J., et al., "A Novel Bicomponent Hemolysin from *Bacillus cereus*", Inspection and Immunity, 58(7):2220–2227 (1990).

Estruch, Juan, et al, "VipA, a novel *Bacillus thuringiensis* vegetative insecticidal protein with a wide spectrum of activities against lepidopteran insects", *Proc. Natl. Acad. Sci. USA*, 93:5389–5394 (1996).

Faust, R.M., "Bacterial Diseases", In: *Insect Diseases*, G. Cantwell, ed., Marcel Dekker, NY 1974, pp. 90–102.

Faust, R.M., et al., "Bacteria and Their Toxins as Insecticides", In: *Microbial and Viral Pesticides*, E. Kurstak, Ed., Marcel Dekker, NY, 1982, pp. 84–89, 108–120.

Gleave, et al., Screening by Poymerase Chain Reaction of *Bacillus thuringiensis* Serotypes for the Presence of cryV–like Insecticidal Protein Genes and Characterization of a cryV Gene Cloned from *B. thuringiensis* subsp. kurstaki, Applied and Environmental.

Gilmore, Michael S., et al., "A *Bacillus cereus* Cytolytic Determinant, Cereolysin AB, Which Comprises the Phospholipase C and Sphingomyelinase Genes: Nucleotide Sequence and Genetic Linkage", *Journal of Bacteriology*, 171(2):744–753 (1989).

Heimpel, A.M., "The pH in the Gut and Blood of the Larch Sawfly, *Pristiphora erichsonii* (HTG.), and Other Insects with Reference to the Pathogenicity of *Bacillus cereus* FR. and FR.", *Can. J. Zool.*, 33:99–106 (1955).

Heimpel, A.M., "Investigations of the Mode of Action of Strains of *Bacillus cereus* FR. and FR. Pathogenic for the Larch Sawfly, *Pristiphora erichsonii* (HTG.)", *Can. J. Zool.*, 33:311–326 (1995).

Hofte, H., et al., "Insecticidal Crystal Proteins of *Bacillus thuringiensis*", *Microbiological Reviews*, 53(2):242–255 (1989).

Kostichka, et al. Cloning of a cryV–type Isecticidal Protein Gene from *Bacillus thuringiensis*: the cry–V encoded Protein Is Expressed Early in Stationary Phase.

Koziel, M.G., et al., "Field Performance of Elite Tansgenic Maize Plants Expressing an Insecticidal Protein Derived from *Bacillus thuringiensis*", *Bio/Technology*, 11:194–200 (1993).

Krieg, A., "Thuricin, a Bacteriocin Produced by *Bacillus thuringiensis*", *J. Invert. Path.*, 15:291 (1970).

Krieg, A., "Concerning Alpha–exotoxin Produced by Vegetative Cells of *Bacillus thuringiensis* and *Bacillus cereus*", *J. Invert. Path.*, 17:134–135 (1971).

Kushner, D.J., et al., "Lecithinase Production by Strains of *Bacillus cereus* FR. and FR. Pathogenic for the Larch Sawfly, *Pristiphora erichsonii* (HTG.)", *Can. J. Microbiol.*, 3:547–551 (1957).

Luthy, P., et al., "*Bacillus thuringiensis* as a Bacterial Insecticide: Basic Consideration and Application", In: *Microbial and Viral Pesticides*, E. Kurstak, Ed., Marcel Dekker, NY 1982, pp. 37–39, 54–56.

(List continued on next page.)

Primary Examiner—Robert A. Wax
Assistant Examiner—Nashaat T. Nashed
Attorney, Agent, or Firm—Gary M. Pace; J. Timothy Meigs

[57] ABSTRACT

The present invention is drawn to a novel class of proteins, and their receptors. Novel processes, assays and methods for controlling plant pests are provided.

30 Claims, 13 Drawing Sheets

OTHER PUBLICATIONS

Myers, P.S., et al., "Localization of a Mosquito–Larval Toxin of *Bacillus sphaericus* 1593", *Appl. Environ. Microbiol.*, 39(1):1205–1211 (1980).

Porter, A.G., et al., "Mosquitocidal Toxins of Bacilli and Their Genetic Manipulation for Effective Biological Control of Mosquitoes", *Microbiological Reviews*, 57(4):838–861 (1993).

Sekar, V., "The Insecticidal Crystal Protein Gene is Expressed in Vegetative Cells of *Bacillus thuringiensis* var. *temebropmos*", *Current Microbiology*, 17:347–349.

Shivakumar, A.G., et al., Abstract,:Cloned Crystal Protein Genes Express Vegetatively in *Bacillus subtilis, Plasmid*, 16(3):230 (1986).

Thanabalu, T., et al., "Proteolytic Processing of the Mosquitocidal Toxin from *Bacillus sphaericus* SSII–1", *J. Bacteriol.*, 174(15):5051–5056 (1992).

Yoshisue, H., et al., "Effects of *Bacillus thuringiensis* var. *israelensis* 20 kDa Protein on Production of the Bti 130–kDa Crystal Protein in *Escherichia coli*", *Bioscience, Biotechnology, and Biochemistry*, 56(9):1429–1433 (1992).

European International Search Report dated May 3, 1996.

Bernier et al., "*Bacillus thuringiensis* Strains A20 and A29 and Insecticidal Compounds Therefrom, and Compositions Containing These Compounds", Abstract No. 227249, *New Zealand Patent Office Journal*, 80(6):798, (1988).

Jellis et al., "*Bacillus thuringiensis* δ–Endotoxin Variants and Insecticidal Compositions", Abstract No. 228108, *New Zealand Patent Office Journal*, 81(3):359, (1992).

Schurter et al., "Genetic Manifpulation of *B.thuringiensis* and *B.cereus* Vectors and Insecticidal Composition", Abstract No. 229191, *New Zealand Patent Office Journal*, 81(3):363, (1992).

Tayabali et al., "Semiautomated Quantification of Cytotoxic Damage Induced in Cultured Insect Cells Exposed to Commercial *Bacillus thuringiensis* Biopesticides", *Journal of Applied Toxicology*, 15(5): 365–373 (1995).

Thanabalu et al., "Cytotoxicity and ADP–Ribosylating Activity of the Mosquitocidal Toxin from *Bacillus sphaericus* SSII–1: Possible Roles of the 27– and 70–Kilodalton Peptides", *Journal of Bacteriology*, 175(8): 2314–2320 (1993).

Vaithlingam et al., "Anti–Coleopteran Toxin and Gene", Abstract No. 226442, *New Zealand Patent Office Journal*, 80(7):931, (1991).

Wahisaka et al., "*Bacillus Thuringiensis* Mutant and Bacterial Insecticide", Abstract No. 199725, *New Zealand Patent Office Journal*, (1982).

Walther et al., "Analysis of Mosquito Larvicidal Potential Exhibited by Vegetative Cells of *Bacillus thuringiensis* subsp. *israelensis*", *Applied and Environmental Microbiology*, 52(4): 650–653 (1986).

Ward et al., "*Bacillus thuringiensis* var. *israelensis* δ–Endotoxin Cloning and Expression of the Toxin in Sporogenic and Asporogenic Strains of *Bacillus subtilis*", *Journal of Molecular Biology*, 191(1): 13–22 (1986).

```
  1                          20
SGSPGLQEFAAASTMYSRIFFLLVIVCAVKASLFTVN
    40                       60
VYDDNPETEIASSLKGCNPQECDQRCRRLKFPGGA
       80                       100
CVNGRCKCDNFLSVKDDVSVEEPAILKDLVSLEAEQ
              120                       140
  AAKSRCRNRVCDAVCRALHNTSGACVDGQCKCTN
                     160
KISAGDIVSDPAESLRTCNPIRCDEQCRRNGHEFGV
   180                       200
CFKGQCKCDYFLKEEVDEPEVTSLPKNCNPQECDQ
              220                       240
RCRRLKFPGGACVNGRCKCDNFFSAGDIVSDPAES
                260                       280
   LRSCNPIRCDEQCRRNGHEFGVCFKGQCKCDYFL
                     300
NSEVDAVNEFPQAGSKRYCNLTQCNQTCANRFYD
     320                       340
SARVIHGWCKCYSKMERQDASPLNDVTEDENEVS
           360                       380
  NDILRTVAEELSDVSPRACKSASCNQACRAFYFKG
                  396
GWCRFGRCQCF
```

Figure 1

```
  1 MNKNNTKLSTRALPSFIDYFNGIYGFATGIKDIMNMIFKTDTGGDLTLDE  50 SEQ ID NO:2
    ||||||||||||||||||||||||||||||||||||||||||||||||||
  1 MNKNNTKLSTRALPSFIDYFNGIYGFATGIKDIMNMIFKTDTGGDLTLDE  50 SEQ ID NO:4

51 ILKNQQLLNDISGKLDGVNGSLNDLIAQGNLNTELSKEILKIANEQNQVL 100
    ||||||||||||||||||||||||||||||||||||||||||||||||||
 51 ILKNQQLLNDISGKLDGVNGSLNDLIAQGNLNTELSKEILKIANEQNQVL 100

101 NDVNNKLDAINTMLRVYLPKITSMLSDVMKQNYALSLQIEYLSKQLQEIS 150
    ||||||||||||||||||||||||||||||||||||||||||||||||||
101 NDVNNKLDAINTMLRVYLPKITSMLSDVMKQNYALSLQIEYLSKQLQEIS 150

151 DKLDIINVNVLINSTLTEITPAYQRIKYVNEKFEELTFATETSSKVKKDG 200
    ||||||||||||||||||||||||||||||||||||||||||||||||||
151 DKLDIINVNVLINSTLTEITPAYQRIKYVNEKFEELTFATETSSKVKKDG 200

201 SPADILDELTELTELAKSVTKNDVDGFEFYLNTFHDVMVGNNLFGRSALK 250
    |||||  |||||||||||||||||||||||||||||||||||||||||||
201 SPADIRDELTELTELAKSVTKNDVDGFEFYLNTFHDVMVGNNLFGRSALK 250

251 TASELITKENVKTSGSEVGNVYNFLIVLTALQAQAFLTLTTCRKLLGLAD 300
    |||||||||||||||||||||||||||||||||||.||||||.|||||||
251 TASELITKENVKTSGSEVGNVYNFLIVLTALQAKAFLTLTPCRKLLGLAD 300

301 IDYTSIMNEHLNKEKEEFRVNILPTLSNTFSNPNYAKVKGSDEDAKMIVE 350
    ||||||||||||||||||||||||||||||||||||||||||||||||||
301 IDYTSIMNEHLNKEKEEFRVNILPTLSNTFSNPNYAKVKGSDEDAKMIVE 350

351 AKPGHALIGFEISNDSITVLKVYEAKLKQNYQVDKDSLSEVIYGDMDKLL 400
    ||||||||||||||||||||||||||||||||||||||||||||||||||
351 AKPGHALIGFEISNDSITVLKVYEAKLKQNYQVDKDSLSEVIYGDMDKLL 400
```

Figure 10A

```
401 CPDQSEQIYYTNNIVFPNEYVITKIDFTKKMKTLRYEVTANFYDSSTGEI 450
    |||||:||||||||||||||||||||||||||||||||||||||||||||
401 CPDQSGQIYYTNNIVFPNEYVITKIDFTKKMKTLRYEVTANFYDSSTGEI 450

451 DLNKKKVESSEAEYRTLSANDDGVYMPLGVISETFLTPINGFGLQADENS 500
    ||||||||||||||||||||||||||||||||||||||||||||||||||
451 DLNKKKVESSEAEYRTLSANDDGVYMPLGVISETFLTPINGFGLQADENS 500

501 RLITLTCKSYLRELLLATDLSNKETKLIVPPSGFISNIVENGSIEEDNLE 550
    ||||||||||||||||||||||||||||||||||||||||||||||||||
501 RLITLTCKSYLRELLLATDLSNKETKLIVPPSGFISNIVENGSIEEDNLE 550

551 PWKANNKNAYVDHTGGVNGTKALYVHKDGGISQFIGDKLKPKTEYVIQYT 600
    ||||||||||||||||||||||||||||||||||||||||||||||||||
551 PWKANNKNAYVDHTGGVNGTKALYVHKDGGISQFIGDKLKPKTEYVIQYT 600

601 VKGKPSIHLKDENTGYIHYEDTNNNLEDYQTINKRFTTGTDLKGVYLILK 650
    ||||||||||||||||||||||||||||||||||||||||||||||||||
601 VKGKPSIHLKDENTGYIHYEDTNNNLEDYQTINKRFTTGTDLKGVYLILK 650

651 SQNGDEAWGDNFIILEISPSEKLLSPELINTNNWTSTGSTNISGNTLTLY 700
    ||||||||||||||||||||||||||||||||||||||||||||||||||
651 SQNGDEAWGDNFIILEISPSEKLLSPELINTNNWTSTGSTNISGNTLTLY 700

701 QGGRGILKQNLQLDSFSTYRVYFSVSGDANVRIRNSREVLFEKRYMSGAK 750
    ||||||||||||||||||||||||||||||||||||||||||||||||||
701 QGGRGILKQNLQLDSFSTYRVYFSVSGDANVRIRNSREVLFEKRYMSGAK 750

751 DVSEMFTTKFEKDNFYIELSQGNNLYGGPIVHFYDVSIK 789
    ||||||||||||||||||||||||||||||||||||||
751 DVSEMFTTKFEKDNFYIELSQGNNLYGGPIVHFYDVSIK 789
```

Figure 10B

```
  1 MNKNNTKLSTRALPSFIDYFNGIYGFATGIKDIMNMIFKTDTGGDLTLDE  50  SEQ ID NO:2
    |||||.||||||||||||||||||||||||||||||||||||||||.|||
  1 MNKNNAKLSTRALPSFIDYFNGIYGFATGIKDIMNMIFKTDTGGDLALDE  50  SEQ ID NO:6

51 ILKNQQLLNDISGKLDGVNGSLNDLIAQGNLNTELSKEILKIANEQNQVL 100
    ||.|||||||||||||||||||||||||||||||||||||||||||||||
 51 ILENQQLLNDISGKLDGVNGSLNDLIAQGNLNTELSKEILKIANEQNQVL 100

101 NDVNNKLDAINTMLRVYLPKITSMLSDVMKQNYALSLQIEYLSKQLQEIS 150
    |||||||||||||||||||||||||||||||||||||||||||||||||
101 NDVNNKLDAINTMLRVYLPKITSMLSDVMKQNYALSLQIEYLSKQLQEIS 150

151 DKLDIINVNVLINSTLTEITPAYQRIKYVNEKFEELTFATETSSKVKKDG 200
    |||||||||||||||||||||||||||||||||||||||||||||||||
151 DKLDIINVNVLINSTLTEITPAYQRIKYVNEKFEELTFATETSSKVKKDG 200

201 SPADILDELTELTELAKSVTKNDVDGFEFYLNTFHDVMVGNNLFGRSALK 250
    |||||   |||.||||||||||.||||||||||||||||||||||||||
201 SPADIRDELSELTELAKSVTQNDVDGFEFYLNTFHDVMVGNNLFGRSALK 250

251 TASELITKENVKTSGSEVGNVYNFLIVLTALQAQAFLTLTTCRKLLGLAD 300
    |||||||||||||||||||||||||||||||||||||||.|||||||||
251 TASELITKENVKTSGSEVGNVYNFLIVLTALQAQAFLTLTPCRKLLGLAD 300

301 IDYTSIMNEHLNKEKEEFRVNILPTLSNTFSNPNYAKVKGSDEDAKMIVE 350
    |||||||||||||||||||||||||||||||||||||||||||||||||
301 IDYTSIMNEHLNKEKEEFRVNILPTLSNTFSNPNYAKVKGSDEDAKMIVE 350

351 AKPGHALIGFEISNDSITVLKVYEAKLKQNYQVDKDSLSEVIYGDMDKLL 400
    |||||||||||||||||||||||||||||||||||||||||||||||||
351 AKPGHALIGFEISNDSITVLKVYEAKLKQNYQVDKDSLSEVIYGDMDKLL 400
```

Figure 11A

```
401 CPDQSEQIYYTNNIVFPNEYVITKIDFTKKMKTLRYEVTANFYDSSTGEI 450
    ||||| :||||||||||||||||||||||||||||||||||||||||||
401 CPDQSGQIYYTNNIVFPNEYVITKIDFTKKMKTLRYEVTANFYDSSTGEI 450

451 DLNKKKVESSEAEYRTLSANDDGVYMPLGVISETFLTPINGFGLQADENS 500
    |||||||||||||||||||||||||||||||||||||||||||||||||
451 DLNKKKVESSEAEYRTLSANDDGVYMPLGVISETFLTPINGFGLQADENS 500

501 RLITLTCKSYLRELLLATDLSNKETKLIVPPSGFISNIVENGSIEEDNLE 550
    |||||||||||||||||||||||||||||||||||||||||||||||||
501 RLITLTCKSYLRELLLATDLSNKETKLIVPPSGFISNIVENGSIEEDNLE 550

551 PWKANNKNAYVDHTGGVNGTKALYVHKDGGISQFIGDKLKPKTEYVIQYT 600
    |||||||||||||||||||||||||||||||||||||||||||||||||
551 PWKANNKNAYVDHTGGVNGTKALYVHKDGGISQFIGDKLKPKTEYVIQYT 600

601 VKGKPSIHLKDENTGYIHYEDTNNNLEDYQTINKRFTTGTDLKGVYLILK 650
    |||||||||||||||||||||||||||||||||||||||||||||||||
601 VKGKPSIHLKDENTGYIHYEDTNNNLEDYQTINKRFTTGTDLKGVYLILK 650

651 SQNGDEAWGDNFIILEISPSEKLLSPELINTNNWTSTGSTNISGNTLTLY 700
    |||||||||||||||||||||||||||||||||||||||||||||||||
651 SQNGDEAWGDNFIILEISPSEKLLSPELINTNNWTSTGSTNISGNTLTLY 700

701 QGGRGILKQNLQLDSFSTYRVYFSVSGDANVRIRNSREVLFEKRYM 746
    |||||||||||||||||||||||||||||||||||||||||| : :
701 QGGRGILKQNLQLDSFSTYRVYFSVSGDANVRIRNSREVLFEKKDI 746
```

Figure 11B

CLASS OF PROTEINS FOR THE CONTROL OF PLANT PESTS

The present invention is a continuation-in-part application of U.S. Ser. No. 08/463,483 filed Jun. 5, 1995, which is a continuation-in-part application of U.S. application Ser. No. 08/314,594 filed Sep. 28, 1994, now abandoned, which is a continuation-in-part application of U.S. application Ser. No. 08/218,018 filed Mar. 23, 1994, now abandoned, which is a continuation-in-part application of U.S. application Ser. No. 08/037,057 filed Mar. 25, 1993, now abandoned, the disclosures of which are herein incorporated by reference.

FIELD OF THE INVENTION

The present invention relates to a novel class of proteins for the control of plant pests.

BACKGROUND OF THE INVENTION

Plant pests are a major factor in the loss of the world's commercially important agricultural crops resulting both in economic hardship to farmers and nutritional deprivation for local populations in many parts of the world. Broad spectrum chemical pesticides have been used extensively to control or eradicate pests of agricultural importance. There is, however, substantial interest in developing effective alternative pesticides.

Control of various pests through the use of biological molecules has been possible in only a limited number of cases. The best known examples of biological molecules with pesticidal uses are the δ-endotoxins from *Bacillus thuringiensis* (Bt), which is a gram-positive spore forming microorganism. Varieties of Bt are known that produce more than 25 different but related δ-endotoxins. Bt strains produce δ-endotoxins during sporulation.

The majority of δ-endotoxins made by Bt are toxic to larvae of certain insects in the orders Lepidoptera, Diptera and Coleoptera. Some of these δ-endotoxins have useful insecticidal activities against different insect pests. However, use of the δ-endotoxins is limited because they are active against only a very few of the many insect pests.

The limited specificity of the Bt endotoxins is dependent, at least in part, on both the activation of the toxin in the insect gut (Haider, M. Z. et al., 1986, Eur. J. Biochem. 156:531–540) and its ability to bind to specific receptors present on the insect's midgut epithelial cells (Hofmann, C. P. et al, 1988, PNAS 85:7844–7848). Among the factors which prevent activity of a particular δ-endotoxin against a specific insect is the lack of appropriate receptors in the insect gut or lack of affinity of the δ-endotoxin for the receptors which may be present, thus resulting in no binding of the δ-endotoxin to the brush border membranes. Therefore, the ability to control a specific insect pest using δ-endotoxins at present depends on the ability to find an appropriate δ-endotoxin with the desired range of activity. In many cases, no such δ-endotoxin is known, and it is not certain that one even exists.

Plants also routinely become infected by fungi and bacteria, and many microbial species have evolved to utilize the different niches provided by the growing plant. Some phytopathogens have evolved to infect foliar surfaces and are spread through the air, from plant-to-plant contact or by various vectors, whereas other phytopathogens are soil-borne and preferentially infect roots and newly germinated seedlings. In addition to infection by fungi and bacteria, many plant diseases are caused by nematodes which are soil-borne and infect roots, typically causing serious damage when the same crop species is cultivated for successive years on the same area of ground.

The severity of the destructive process of disease depends on the aggressiveness of the phytopathogen and the response of the host, and one aim of most plant breeding programs is to increase the resistance of host plants to disease. Novel gene sources and combinations developed for resistance to disease have typically only had a limited period of successful use in many crop-pathogen systems due to the rapid evolution of phytopathogens to overcome resistance genes. In addition, there are several documented cases of the evolution of fungal strains which are resistant to particular fungicides, such as powdery mildew, wheat mildew, *Botrytis, Pyrenophora, Pseudocercosporella* and *Mycosphaerellafijiensis* (Jones and Clifford; Cereal Diseases, John Wiley, 1983).

It is apparent, therefore, that scientists must constantly be in search of new methods with which to protect crops against plant pests. It has been found in the present invention a novel class of proteins which can be used to control plant pests.

Programmed cell death is a process whereby developmental or environmental stimuli activate a genetic program that culminate in the death of the cell (Jacobson, M. D. et al., 1997,Cell 88: 347–354). This genetic potential exists in most, if not all, multicellular organisms. In the case of invertebrates, programmed cell death appears to play a dual role by being an integral part of both the insect development process and a response mechanism to infections particularly of viral nature (Clem, R. J. et al.,1991, Science 254: 1388–1390). Programmed cell death appears to be executed in several different manners leading to either apoptosis, atrophy or differentiation. Apoptosis is one of the best characterized types of programmed cell death encompassing cytological changes including membrane-bound apoptotic bodies and cytoplasmic blebbing as well as molecular changes such as endonucleolysis typified by the generation of oligosomal length fragments (Vaux, D. L and Strasser, A., 1996, PNAS 93:2239–2244). Although the overall apoptotic phenomenology is rather conserved among the different organisms, it is interesting to point out that, for many insect cells, cytoplasmic vacuolization and swelling rather than condensation seem to be the cytological features associated with apoptotic processes (Bowen, I. D., et al,1996, Micros. Res. Techniq.34:202–217). The present invention provides a novel class of proteins which induce programmed cell death and exert a pesticidal effect.

SUMMARY OF THE INVENTION

The present invention is drawn to proteins of the VIP3 class. Preferred proteins are VIP3A(a), VIP3A(b) and VIP3A(c). Also preferred are homologues of VIP3A(a), VIP3A(b) and VIP3A(c). Also provided by the invention are domains of the VIP3 proteins, including the toxic domain and the stabilizing domain. A preferred embodiment of the invention is the toxic domain of the VIP3A(a) protein and homologues thereof. Another preferred embodiment are antibodies to proteins of the VIP3 class.

The invention also provides hybrid toxins comprising a toxic domain of a protein of the VIP3 class. In a preferred embodiment, the hybrid toxin is a chimeric proteins having a toxic core domain operably linked to a heterologous stabilizing domain. In another preferred embodiment, the hybrid toxin comprises an antibody, or immunologically-active fragment thereof, which immunologically recognizes the VIP3 receptor operably linked to a toxic domain from other proteins, wherein the toxin domain is obtained from a number of cytotoxic proteins including but not limited to Bacillus toxins, including endotoxins and vegetative insecticidal proteins.

Also encompassed by the invention are plants comprising a DNA sequence which encodes a protein of the VIP3 class. Preferred embodiments include plants selected from the group consisting of maize, sorghum, wheat, sunflower, tomato, cole crops, cotton, rice, soybean, sugarbeet, sugarcane, tobacco, barley, and oilseed rape. In a particularly preferred embodiment, the plant is a maize plant.

Also provided by the invention are plants further comprising a second DNA sequence which encodes a second insecticidal protein. Particularly preferred second DNA sequences are those which encode a δ-endotoxin, those which encode another protein of the VIP3 class, or those which encode a protein of the VIP1 or VIP2 classes. In a more preferred embodiment, the δ-endotoxin is active against an insect selected from the group consisting of Lepidoptera and Coleoptera. In a more particularly preferred embodiment the δ-endotoxin is active against Ostrinia, or Diabrotica. In another particularly preferred is a second DNA sequence which encodes a δ-endotoxin protein selected from the group consisting of Cry1, Cry3, Cry5 and Cry9. In a more particularly preferred embodiment, the δ-endotoxin is selected from the group consisting of Cry1Aa, Cry1Ab, Cry1Ac, Cry1B, Cry1C, Cry1D, Cry1Ea, Cry1Fa, Cry3A, Cry9A, Cry9C and Cry9B. Most particularly preferred are δ-endotoxins selected from the group consisting of Cry1Ab, Cry1Ba and Cry9C proteins.

The invention also provides microorganisms comprising a heterologous DNA sequence which encodes a protein of the VIP3 class. In a preferred embodiment, the microorganism is selected from the group consisting of bacteria, baculovirus, algae and fungi. In another preferred embodiment, the microorganism is selected from the group consisting of Bacillus, Pseudomonas, Clavibacter, and Rhizobium. Further encompassed by the invention are entomocidal compositions comprising microorganisms comprising a heterologous DNA sequence which encodes a protein of the VIP3 class. Also provided by the invention are microorganisms further comprising a second DNA sequence which encodes a second insecticidal protein. Particularly preferred second DNA sequences are those which encode a δ-endotoxin, those which encode another protein of the VIP3 class, or those which encode a protein of the VIP1 or VIP2 classes. In a more preferred embodiment, the δ-endotoxin is active against an insect selected from the group consisting of Lepidoptera and Coleoptera. In a more particularly preferred embodiment the δ-endotoxin is active against Ostrinia, or Diabrotica. In another particularly preferred is a second DNA sequence which encodes a δ-endotoxin endotoxin protein selected from the group consisting of Cry1, Cry3, Cry5 and Cry9. In a more particularly preferred embodiment, the δ-endotoxin is selected from the group consisting of Cry1Aa, Cry1Ab, Cry1Ac, Cry1B, Cry1C, Cry1D, Cry1Ea, Cry1Fa, Cry3A, Cry9A, Cry9C and Cry9B. Most particularly preferred are δ-endotoxins selected from the group consisting of Cry1Ab, Cry1Ba and Cry9C proteins.

The invention further provides a method of controlling insects by contacting the insects with an insecticidal amount of a protein of the VIP3 class or an insecticidal amount of a chemical ligand to a receptor of the VIP3 class of proteins. In one preferred embodiment, the insects are contacted with a transgenic plant comprising a DNA sequence which expresses a protein of the VIP3 class. In another preferred embodiment, the insects are contacted with a an entomocidal composition comprising a protein of the VIP3 class, or comprising a DNA sequence which expresses a protein of the VIP3 class. In another preferred embodiment, the transgenic plant comprises a DNA sequence which expresses the VIP3A(a) protein. In another preferred embodiment the insect is selected from the group consisting of Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, and Acari. In a particularly preferred embodiment, the insect is a Coleoptera or Lepidoptera. In another particularly preferred embodiment, the insect is selected from the group consisting of black cutworm (*Agrotis ipsilon*), fall armyworm (*Spodoptera frugiperda*), beet armyworm (*S. exigua*), yellow striped armyworm (*S. ornithogalli*), southwestern corn borer (*Diatraea grandiosella*), sugarcane borer (*D. saccharalis*), corn earworm (*Helicoverpa zea*), mediterranean corn borer (*Sesamia nonagroides*), cabbage looper (*Trichoplusia ni*), velvetbean caterpillar (*Anticarsia gemmatalis*), diamondback moth (*Plutella xylostella*) and tobacco budworm (*Heliothis virescens*).

Also provided by the invention is a method of controlling insects wherein the transgenic plant or microorganism further comprises a second DNA sequence which encodes a second insecticidal protein. Particularly preferred second DNA sequences are those which encode a δ-endotoxin, those which encode another protein of the VIP3 class, or those which encode a protein of the VIP1 or VIP2 classes. In a more preferred embodiment, the δ-endotoxin is active against an insect selected from the group consisting of Lepidoptera and Coleoptera. In a more particularly preferred embodiment the δ-endotoxin is active against Ostrinia, or Diabrotica. In another particularly preferred is a second DNA sequence which encodes a δ- endotoxin protein selected from the group consisting of Cry 1, Cry3, Cry5 and Cry9. In a more particularly preferred embodiment, the δ-endotoxin is selected from the group consisting of Cry1Aa, Cry1Ab, Cry1Ac, Cry1B, Cry1C, Cry1D, Cry1Ea, Cry1Fa, Cry3A, Cry9A, Cry9C and Cry9B. Most particularly preferred are δ-endotoxins selected from the group consisting of Cry1Ab, Cry1Ba and Cry9C proteins.

The invention further provides recombinant DNA sequences which encode a protein of the VIP3 class. Preferred embodiments of the DNA sequence encode a protein selected from the group consisting of VIP3A(a), VIP3A(b), VIP3A(c). Also preferred are DNA sequences identified as homologues of vip3A(a). In another preferred embodiment, the DNA sequence is a synthetic sequence which has been altered for optimum expression in a plant, particularly where the DNA sequence has been optimized for expression in a maize plant. Also preferred are DNA sequences which comprise both a synthetic portion and a native portion. In a particularly preferred embodiment, the DNA sequence encoding the VIP3A(a) protein has been optimized for expression in a maize plant. Another preferred embodiment are DNA sequences which are homologous to a DNA sequence which encodes a protein of the VIP3 class. Particularly preferred are DNA sequences which hybridize under moderately stringent conditions to the vip3A(a) coding sequence. Yet another embodiment of the invention is a recombinant DNA sequence which expresses a protein of the VIP3 class under the control of a heterologous promoter, or wherein the coding regions is incorporated into the genome of an organism where it is not naturally expressed or is expressed at higher levels than that occuring naturally.

The invention is further drawn to a method of identifying and isolating homologues of a protein of the VIP3 class or of a DNA sequence which encodes a protein of the VIP3 class. In a preferred embodiment, the method comprises obtaining a DNA sequence which encodes a protein of the VIP3 class, hybridizing said DNA sequence with DNA obtained from a test organism, and isolating said hybridized DNA. In another preferred embodiment, the method comprises obtaining a DNA sample from an organism, using primers to a DNA sequence encoding a protein of the VIP3 class and obtaining a reaction product, then isolating a DNA sequence which encodes a protein of the VIP3 class from said organism. In another preferred embodiment, the method comprises obtaining a protein sample from a test organism, obtaining an antibody to a protein of the VIP3 class, reacting said antibody with said protein sample, and detecting and isolating homologues by detecting the presence of an immunological reaction.

Also provided by the invention are expression cassettes comprising a promoter operably linked to a DNA sequence encoding a protein of the VIP3 class. In one preferred embodiment the promoter is selected from the group consisting of constitutive, tissue-preferred preferred and tissue-specific promoters for expression in plants. In a particularly preferred embodiment, the promoter is selected from the group consisting of the ubiquitin, PEP carboxylase, LPT and MTL promoters. In another preferred embodiment, the promoter is functional in a microorganism.

The invention further provides a receptor to a protein of the VIP3 class and DNA sequences which. In one embodiment of the invention, the receptor comprises a death domain and a repeated EGF-motif. A more preferred embodiment of the invention comprises a receptor to the VIP3A(a). A more particularly preferred embodiment is the receptor protein sequence set forth in SEQ ID NO:9, and homologues thereto. Also encompassed by the invention are DNA sequences which encode these receptor proteins, e.g., the DNA sequence set forth in SEQ ID NO:8 and homologues thereto. Antibodies to a receptor of the VIP3 class of proteins are also encompassed by the invention.

Also provided by the invention is a method of identifying a compound as a VIP3 receptor chemical ligand having pesticidal activity comprising exposing a cell, preferably an insect cell, to a test compound, and assaying said cell for apoptotic activity. In another embodiment of the invention, the method comprises measuring specific binding between VIP3 receptor and a test compound. A preferred embodiment are VIP3 receptor ligands identified by the method.

BRIEF DESCRIPTION OF THE FIGURES

FIG. 1: Amino acid sequence of the receptor for VIP3A(a) translated from the cDNA. Several features of the protein are shown: dotted line—signal peptide (amino acid 13 to 35); italic—domain spanning the putative death domain (amino acid 81–205); double underline—sequences with strong homology to sequences found in consensus death domains; bold—CKC motif repeated six times spanning the EGF-motifs; underline—sequences repeated within the EGF-motifs.

FIGS. 10a and b: Alignment of VIP3A(a) (Upper Line) against VIP3A(b) (Lower Line)

FIGS. 11a and b: Alignment of VIP3A(a) (Upper Line) against VIP3A(c) (Tower Line).

DETAILED DESCRIPTION OF THE INVENTION

Definitions

Figure 2:
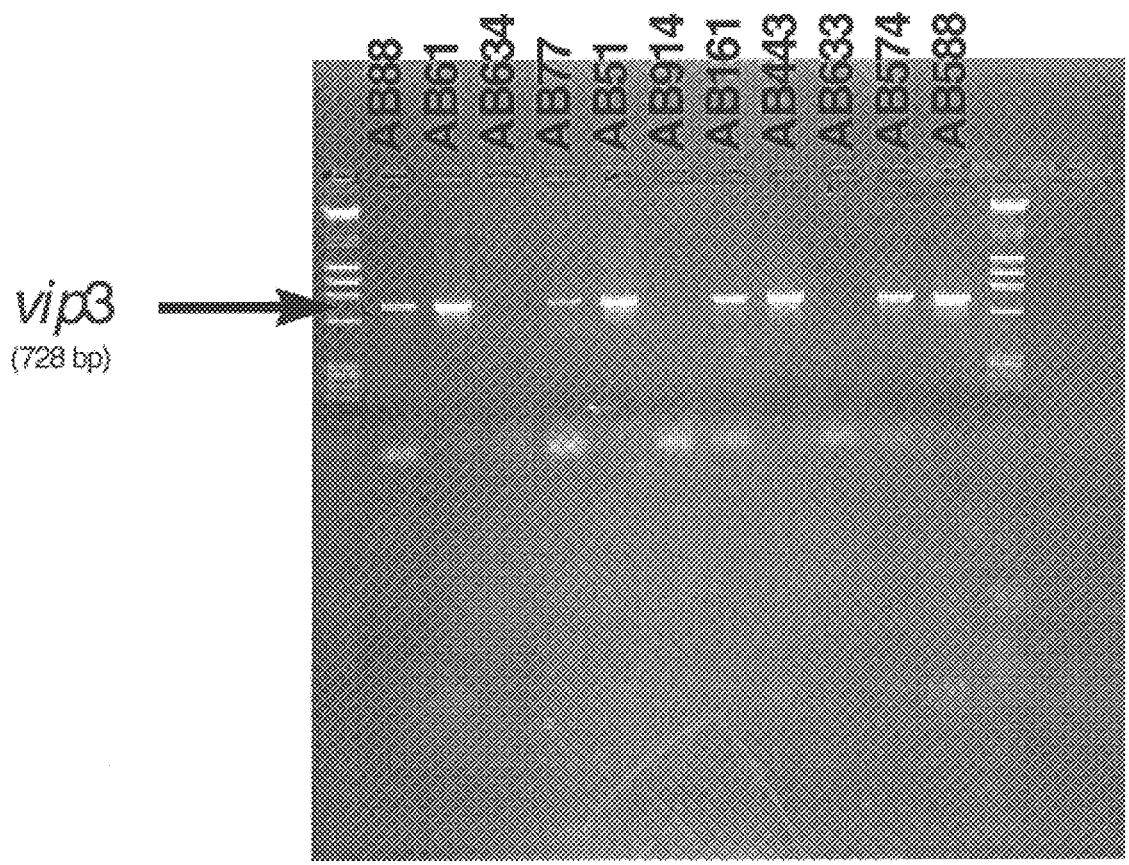
FIG. 2: Presence of vip3 genes in Bacillus isolates as identified by PCR assay.

"Plant pest" means any organism known to associate with plants and which, as a result of that association, causes a detrimental effect on the plant's health and vigor. Plant pests include but are not limited to fungi, bacteria, insects, and nematodes. The term plant as used herein encompasses whole plants and parts of plants such as roots, stems, leaves and seed, as well as cells and tissues within the plants or plant parts.

The "VIP3 class of proteins" comprises VIP3A(a), VIP3A (b) VIP3A(c) and their homologues. "Homologue" is used throughout to mean that the indicated protein or polypeptide bears a defined relationship to other members of the VIP3 class of proteins. This defined relationship includes but is not limited to, 1) proteins which are at least 70%, more preferably 80% and most preferably 90% identical at the sequence level to another member of the VIP3 class of proteins while also retaining pesticidal activity, 2) proteins which are cross-reactive to antibodies which immunologically recognize another member of the VIP3 class of proteins, 3) proteins which are cross-reactive with a receptor to another member of the VIP3 class of proteins and retain the ability to induce programmed cell death, and 4) proteins which are at least 70%, more preferably 80% and most preferably 90% identical at the sequence level to the toxic core region of another member of the VIP3 class of proteins while also retaining pesticidal activity.

A "hybrid toxin" is used to indicate a genetic fusion, having domains operably linked so that, when translated, a functional chimeric protein is formed having, in the aggregate, the properties of the individual domains. "Domain" is used to indicate a region or portion of a protein or confers a recognizable function or structure which contributes to the overall functionality of the protein. It is recognized that a DNA sequence which encodes a protein domain is also encompassed by this definition.

"Heterologous" is used to indicate that a protein, polypeptide or nucleotide sequence has a different natural origin with respect to its current host. For example, if a vip3A(a) gene from a *Bacillus thuringiensis* is genetically transformed into a plant cell, then the gene is described as being heterologous with respect to its current host, which is the plant cell. Furthermore, if a vip3A(a) gene from *Bacillus thuringiensis* is genetically transformed into a Pseudomonas bacterium, then the gene is also described as being heterologous with respect to the Pseudomonas. "Heterologous" is also used to indicate that one or more of the domains present in a chimeric protein, polypeptide or nucleotide sequence differ in their natural origin with respect to other domains present. For example, if the toxic domain from VIP3A(a) protein is fused to the binding domain from the VIP1A(a) protein to make a functional insecticidal protein, then the chimeric fusion would have domains that are heterologous to each other. In addition, a heterologous chimeric protein or polypeptide comprising the fusion of a toxic domain from VIP3A(a) protein to the binding domain from the VIP1A(a) protein, when expressed in a plant, would also be considered heterologous with respect to the plant host.

The term "chimeric" is used to indicate that the protein, polypeptide, or nucleotide sequence is comprised of domains at least one of which has an origin that is heterologous with respect to the other domains present. These chimeric proteins or polypeptides are encoded by chimeric nucleotide sequences which have been fused or ligated together resulting in a coding sequence which does not occur naturally. Such chimeric constructions may also be designated as "recombinant."

"Expression cassette" as used herein means a DNA sequence capable of directing expression of a gene in plant cells, comprising a promoter operably linked to an amino acid coding region which is operably linked to a termination region. The gene may be chimeric, meaning that at least one component of the gene is heterologous with respect to at least one other component of the gene. The gene may also be naturally occurring, but which has been obtained in a recombinant form useful for genetic transformation of a plant or microorganism.

Arthropod Pests

For purposes of the present invention, pests include insects and arachnids selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, and Acari, particularly Coleoptera and Lepidoptera.

A list of pests associated with major crop plants are provided in Tables 1–19. Such pests are included within the scope of the present invention.

TABLE 1

Lepidoptera (Butterflies and Moths)

| Maize | *Agrotis ipsilon*, black cutworm |
|---|---|
| *Ostrinia nubilalis*, European corn borer | Tomato |
| *Agrotis ipsilon*, black cutworm | *Helicoverpa zea*, tomato fruitworm |
| *Helicoverpa zea*, corn earworm | *Spodoptera exigua*, beet armyworm |
| *Spodoptera frugiperda*, fall armyworm | *Spodoptera frugiperda*, fall armyworm |
| *Diatraea grandiosella*, southwestern corn borer | *Spodoptera ornithogalli*, yellowstriped armyworm |
| *Elasmopalpus lignosellus*, lesser cornstalk borer | *Spodoptera praefica*, western yellowstriped armyworm |
| *Diatraea saccharalis*, sugarcane borer | |
| *Sesamia nonagroides*, Mediterranean corn borer | *Spodoptera eridania*, southern armyworm |
| *Ostrinia furnacali's*, Asian corn borer | *Agrotis ipsilon*, black cutworm |
| Sorghum | *Peridroma saucia*, variegated cutworm |
| *Chilo partellus*, sorghum borer | *Papaipema nebris*, stalk borer |
| *Spodoptera frugiperda*, fall armyworm | *Trichoplusia ni*, cabbage looper |
| *Helicoverpa zea*, corn earworm | *Keiferia lycopersicella*, tomato pinworm |
| *Elasmopalpus lignosellus*, lesser cornstalk borer | *Manduca sexta*, tobacco hornworm |
| *Feltia subterranea*, granulate cutworm | *Manduca quinquemaculata*, tomato hornworm |
| Wheat | |
| *Pseudaletia unipunctata*, army worm | |
| *Spodoptera frugiperda*, fall armyworm | |
| *Elasmopalpus lignosellus*, lesser cornstalk borer | |
| *Agrotis orthogonia*, pale western cutworm | |
| *Elasmopalpus lignosellus*, lesser cornstalk borer | |
| Sunflower | |
| *Suleima helianthana*, sunflower bud moth | |
| *Homoeosoma electellum*, sunflower moth | |
| Cotton | |
| *Heliothis virescens*, cotton boll worm | |
| *Helicoverpa zea*, cotton bollworm | |
| *Spodoptera exigua*, beet armyworm | |
| *Pectinophora gossypiella*, pink bollworm | |
| *Helicoverpa armigera*, cotton bollworm | |
| Rice | |
| *Diatraea saccharalis*, sugarcane borer | |
| *Spodoptera frugiperda*, fall armyworm | |
| *Helicoverpa zea*, corn earworm | |
| *Chilo suppressalis*, asiatic rice borer | |
| *Scirpophaga sp.* | |
| Soybean | |
| *Pseudoplusia includens*, soybean looper | |
| *Anticarsia gemmatalis*, velvetbean caterpillar | |
| *Plathypena scabra*, green cloverworm | |
| *Ostrinia nubilalis*, European corn borer | |
| *Agrotis ipsilon*, black cutworm | |
| *Spodoptera exigua*, beet armyworm | |
| *Heliothis virescens*, cotton boll worm | |
| *Helicoverpa zea*, cotton bollworm | |

TABLE 1-continued

Lepidoptera (Butterflies and Moths)

Barley

*Ostrinia nubilalis*, European corn borer
Crucifers (broccoli, cabbage, cauliflower, collards)

*Artogeia rapae*, imported cabbageworm
*Pieris brassicae*, cabbage butterfly
*Trichoplusia ni*, cabbage looper
*Plutella xylostella*, diamondback moth
*Spodoptera exigua*, beet armyworm
*Agrotis ipsilon*, black cutworm
*Agrotis segetum*, common cutworm
*Mamestra configura*, bertha army worm
Grapes

*Endopiza viteana*, grape berry moth
Deciduous Fruits and Nuts

*Cydia pomonella*, codling moth
*Platynota idaeusalis*, tufted apple bud moth
Peppers

*Ostrinia nubilalis*, European corn borer
*Spodoptera exigua*, beet armyworm
*Spodoptera eridania*, southern armywonn
Potato

*Ostrinia nubilalis*, European corn borer
*Phthorimaea operculella*, potato tuberworm
Canola

*Plutella xylostella*, diamondback moth
Sugarcane

*Diatraea saccharalis*, sugarcane borer

TABLE 2

Coleopetera (Beetles)

| Maize | Cotton |
|---|---|
| *Diabrotica virgifera. virgifera*, western corn rootworm | *Anthonomus grandis*, boll weevil |
| | Rice |
| *Diabrotica longicornis barberi*, northern corn rootworm | *Colaspis brunnea*, grape colaspis |
| | *Lissorhoptrus oryzophilus*, rice water weevil |
| *Diabrotica undecimpunctata howardi*, southern corn rootworm | *Sitophilus oryzae*, rice weevil |
| | *Oulema oryzae*, rice beetle |
| *Melanotus spp.*, wireworms | Soybean |
| *Cyclocephala borealis*, northern masked chafer (white grub) | *Epilachna varivestis*, Mexican bean beetle |
| | Tomato |
| *Cyclocephala immaculata*, southern masked chafer (white grub) | *Leptinotarsa decemlineata*, Colorado potato beetle |
| | *Epitrix hirtipennis*, tobacco flea beetle |
| *Popillia japonica*, Japanese beetle | Crucifers (broccoli, cabbage, cauliflower, collards) |
| *Chaetocnema pulicaria*, corn flea beetle | *Phyllotreta cruciferae*, crucifer flea beetle |
| *Sphenophorus maidis*, maize billbug | *Phyllotreta pusilla*, western black flea beetle |
| Sorghum | Peppers |
| *Phyllophaga crinita*, white grub | *Anthonomus eugenii*, pepper weevil |
| *Eleodes, Conoderus,* and *Aeolus spp.*, wireworms | Potato |
| *Oulema melanopus*, cereal leaf beetle | *Leptinotarsa decemlineata*, Colorado potato beetle |
| *Chaetocnema pulicaria*, corn flea beetle | *Epitrix cucumeris*, potato flea beetle |
| *Sphenophorus maidis*, maize billbug | *Hemicrepidus memnonius*, wireworms |

TABLE 2-continued

| Coleopetera (Beetles) | |
|---|---|
| Wheat | *Melanpotus spp.*, wireworms |
| *Oulema melanopus*, cereal leaf beetle | Canola |
| *Hypera punctata*, clover leaf weevil | *Ceutorhychus assimils*, cabbage seedpod weevil |
| *Diabrotica undecimpunctata howardi*, southern corn rootworm | *Phyllotreta cruciferae*, crucifer flea beetle |
| Sunflower | |
| *Zygogramma exclamationis*, sunflower beetle | |
| *Bothyrus gibbosus*, carrot beetle | |

TABLE 3

| Homoptera (Whiteflies, Aphids etc..) | |
|---|---|
| Maize | *Bemisia tabaci*, sweetpotato whitefly |
| *Rhopalosiphum maidis*, corn leaf aphid | *Bemisia argentifolii*, silverleaf whitefly |
| *Anuraphis maidiradicis*, corn root aphid | Crucifers (Broccoli, cabbage, cauliflower, collards) |
| Sorghum | *Brevicoryne brassicae*, cabbage aphid |
| *Rhopalosiphum maidis*, corn leaf aphid | *Myzus persicae*, green peach aphid |
| *Sipha flava*, yellow sugarcane aphid | Peppers |
| Wheat | *Myzus persicae*, green peach aphid |
| Russian wheat aphid | Potato |
| *Schizaphis graminum*, greenbug | *Enipoasca fabae*, potato leafhopper |
| *Macrosiphum avenae*, English grain aphid | *Myzus persicae*, green peach aphid |
| Cotton | *Macrosiphum euphorbiae*, potato aphid |
| *Aphis gossypii*, cotton aphid | *Paratrioza cockerelli*, potato psyllid |
| *Pseudatomoscelis seriatus*, cotton fleahopper | Melon |
| *Trialeurodes abutilonea*, bandedwinged whitefly | *Bemisia argentifolii*, silverleaf whitefly |
| Rice | *Bemisia tabaci*, sweetpotato whitefly |
| *Nephotettix nigropictus*, rice leafhopper | Carrot |
| *Nilaparvata lugens* | *Cavariella aegopodii*, carrot aphid |
| *Sogatella furcifera* | Canola |
| *Laodelphaax striatellus* | *Brevicoryne brassicae*, cabbage aphid |
| Soybean | Vegetables |
| *Myzus persicae*, green peach aphid | *Aphis fabae*, bean aphid |
| *Empoasca fabae*, potato leafhopper | Sugar Beet |
| Barley | *Pemphigus populivenae*, sugar beet root aphid |
| *Schizaphis graminum*, greenbug | Deciduous Fruits and Nuts |
| Oil Seed Rape | *Dysaphis plantaginea*, rosy apple aphid |
| *Brevicoryne brassicae*, cabbage aphid | Sugarcane |
| Tomato | *Saccharosydne saccharivora*, West Indian canefly |
| *Myzus persicae*, green peach aphid | *Sipha flava*, yellow sugarcane aphid |
| *Macrosiphum euphorbiae*, potato aphid | |
| *Trileurodes vaporariorum*, greenhouse whitefly | |

TABLE 4

Hemiptera (Bugs)

Maize

*Blissus leucopterus leucopterus*, chinch bug

Sorghum

*Blissus leucopterus leucopterus*, chinch bug

Cotton

*Lygus lineolaris*, tarnished plant bug

Rice

*Blissus leucopterus leucopterus*, chinch bug
*Acrosternum hilare*, green stink bug

Soybean

*Acrosternum hilare*, green stink bug

Barley

*Blissus leucopterus leucopterus*, chinch bug
*Acrosternum hilare*, green stink bug
*Euschistus servus*, brown stink bug

Tomato

*lygus bug*
*Acrosternum hilare*, green stink bug
*Euschistus servus*, brown stick bug

TABLE 5

Orthoptera (Grasshoppers Crickets, and Cockroaches)

Maize

*Melanoplus femurrubrum*, redlegged grasshopper
*Melanoplus sanguinipes*, migratory grasshopper

Wheat

*Melanoplus femurrubrum*, redlegged grasshopper
*Melanoplus differenualis*, differential grasshopper
*Melanoplus sanguinipes*, migratory grasshopper

Cotton

*Melanoplus femurrubrum*, redlegged grasshopper
*Melanoplus differentialis*, differential grasshopper

Soybean

*Melanoplus femurrubrum*, redlegged grasshopper
*Melanoplus differentiahs*, differential grasshopper

TABLE 6

Diptera (Flies and Mosquitoes)

Maize

*Hylemya platura*, seedcorn maggot
*Agromyza parvicornis*, corn blotch leafminer

Sorghum

*Contarinia sorghicola*, sorghum midge

Wheat

*Mayetiola destructor*, Hessian fly
*Sitodiplosis mosellana*, wheat midge
*Meromyza americana*, wheat stem maggot
*Hylemya coarctata*, wheat bulb fly

Sunflower

*Neolasioptera murtfeldtiana*, sunflower seed midge

Soybean

*Hylemya platura*, seedcorn maggot

TABLE 6-continued

Diptera (Flies and Mosquitoes)

Barley

*Hylemya platura*, seedcorn maggot
*Mayetiola destructor*, Hessian fly

Tomato

*Liriomyza trifolli*, leafminer
*Liriomyza sativae*, vegetable leafminer
*Scrobipalpula absoluta*, tomato leafminer

Crucifers (broccoli, cabbage, cauliflower, collards)

*Delia brassicae*, cabbage maggot
*Delia radicum*, cabbage root fly

Carrot

*Psilia rosae*, carrot rust fly

Sugarbeet

*Tetanops myopaeformis*, sugarbeet root maggot

Vegetables

*Liviomyza sativae*, vegetable leaf miner

TABLE 7

Thysanontera (Thrips)

Maize

*Anaphothrips obscurus*, grass thrips

Wheat

*Frankliniella fusca*, tobacco thrips

Cotton

*Thrips tabaci*, onion thrips
*Frankliniella fusca*, tobacco thrips

Soybean

*Sericothrips vanabilis*, soybean thrips
*Thrips tabaci*, onion thrips

Tomato

*Frankliniella occidentakis*, western flower thrips
*Frankliniella fusca*, tobacco thrips
*Thrips tabaci*, onion thrips

Crucifers (broccoli, cabbage, cauliflower, collards)

*Thrips tabaci*, onion thrips

Peppers

*Thrips palmi*, melon thrips

Potato

*Thrips palmi*, melon thrips

TABLE 8

Hymenoptera (Sawflies, Ants, Wasps etc)

Maize

*Solenopsis milesta*, thief ant

Wheat

*Cephus cinctus*, wheat stem sawfly

TABLE 9

Acari (Mites and Ticks)

Maize

*Tetranychus urticae*, twospotted spider mite

Sorghum

*Tetranychus cinnabarinus*, carmine spider mite
*Tetranychus urticae*, twospotted spider mite

Wheat

*Aceria tulipae*, wheat curl mite

Cotton

*Tetranychus cinnabarinus*, carmine spider mite
*Tetranychus urticae*, twospotted spider mite

Soybean

*Tetranychus turkestani*, strawberry spider mite.
*Tetranychus urticae*, twospotted spider mite

Barley

*Petrobia latens*, brown wheat mite

Tomato

*Tetranychus urticae*, two spotted spider mite
*Aculops iycopersici*, tomato russet mite
*Steneotarsonemus pallidus*, cyclamen mite

Citrus

*Panonychus citri*, citrus red mite
*Brevipalpus lewisi*, citrus flat mite
*Phyllocoptrutra oleivora*, citrus rust mite

Deciduous Fruits and Nuts

*Panonychus ulmi*, European red mite
*Tetranchus sp*, spider mite

---

For purposes of the present invention, pests also include fungal phytopathogens of plants. A list of fungal pests associated with major crop plants is provided in Table 10. Such pests are included within the scope of the present invention.

TABLE 10

Fungal Diseases of Plants

Ear Molds

| | |
|---|---|
| Gibberella ear mold | *Gibberella zeae* |
| | *G. saubinetti* |
| Aspergillus ear rot | *Aspergillus flavus* |
| | *A. parasiticus* |
| Diplodia ear rot | *Diplodia maydis* |
| | *D. macrospora* |
| Fusarium ear rot | *Fusarium moniliforme* |
| | *F. monilif. var. subglutinans* |

Stalk Rots

| | |
|---|---|
| Pythium stalk rot | *Pythium aphanidermata* |
| Anthracnose stalk rot | *Colletotrichum graminicola* |
| | *C. tucumanensis* |
| | *Glomerella graminicola* |
| Diplodia stalk rot | *Diplodia maydis* |
| | *D. zeae-maydis* |
| | *Stenocarpella maydis* |
| | *Macrodiplodia zeae* |
| | *Sphaeria maydis* |
| | *S. zeae* |
| | *D. macrospora* |
| Fusarium stalk rot | *Fusarium moniliforme* |
| Gibberella stalk rot | *G. zeae* |
| | *G. saubinetti* |
| Stewart's wilt & leaf blight | *Erwinia stewartii* |

TABLE 10-continued

Fungal Diseases of Plants

Ear Molds

Leaf Diseases

| | |
|---|---|
| Northern corn leaf blight | *Exserohilum turcicum* |
| Southern corn leaf blight | *Bipolaris maydis* |
| Gray leaf spot | *Cercospora zeae-maydis* |
| | *C. sorghi var. maydis* |
| Anthracnose leaf blight | *Colletotrichum graminicola* |
| Common rust | *Puccinia sorghi* |
| | *P. maydis* |
| Southern rust | *Puccinia polysora* |
| | *Dicaeoma polysorum* |
| Head smut | *Sphacelotheca reiliana* |
| Common smut | *Ustilago maydis* |
| Carbonum leaf spot | *Helminthosporium carbonum* |
| Eye spot | *Kabatiella zeae* |

Downy Mildews

| | |
|---|---|
| Sorghum downy mildew | *Peronosclerospora sorghi* |
| Brown stripe downy mildew | *Sclerophthora rayssiae* |
| Sugarcane downy mildew | *Peronosclerospora sacchari* |
| Phillipine downy mildew | *Peronoscler. philippinensis* |
| Java downy mildew | *Peronosclerospora maydis* |
| Spontaneum downy mildew | *Peronosclerospora spontanea* |
| Rajasthan downy mildew | *Peronosclerospora heteropogoni* |
| Graminicola downy mildew | *Sclerospora graminicola* |
| Rusts | *Puccinia graminis f.sp. tritici* |
| | *Puccinia recondita f.sp. tritici* |
| | *Puccinia striiformis* |
| Smuts | *Tilletia tritici* |
| | *Tilletia controversa* |
| | *Tilletia indica* |
| | *Ustilago tritici* |
| | *Urocystis tritici* |
| Root rots, Foot rots and Blights | *Gaeumannomyces graminis* |
| | *Pythium spp.* |
| | *Fusarium culmorum* |
| | *Fusarium graminaerum* |
| | *Fusarium avenaceum* |
| | *Drechslere tritici-repentis* |
| | *Rhizoctonia spp.* |
| | *Colletotrichum graminicola* |
| | *Helminthosporium spp.* |
| | *Microdochium nivale* |
| | *Pseudocercosporella herpotrichoides* |
| Mildews | *Erysiphe graminis f.sp. tritici* |
| | *Sclerophthora macrospora* |
| Miscellaneous Fungal Diseases | *Septoria tritici* |
| | *Septoria nodorum* |

VIP3 is a Novel Class of Proteins

The proteins of the VIP3 class are secreted to the media by Bacillus spp. in vegetative stages of growth. VIP3A(a) is a member of a newly discovered class of proteins displaying insecticidal activity against a broad spectrum of lepidopteran insects including black cutworm (*Agrotis ipsilon*), fall armyworm (*Spodoptera frugiperda*), beet armyworm (*S. exigua*), yellow striped armyworm (*S. ornithogalli*), southwestern corn borer (*Diatraea grandiosella*), sugarcane borer (*D. saccharalis*), corn earworm (*Helicoverpa zea*), Mediterranean corn borer (*Sesamia nonagroides*), cabbage looper (*Trichoplusia ni*), velvetbean caterpillar (*Anticarsia gemmatalis*), diamondback moth (*Plutella xylostella*) and tobacco budworm (*Heliothis virescens*). Some of these lepidopteran insects have been shown to be very resistant to other insecticidal proteins such as δ-endotoxin. For example, the reported $LC_{50}$ for Cry1A(c), which is one of the most effective δ-endotoxin against black cutworm, is greater than 6000 ng/cm$^2$ (MacIntosh et al., J. Invertebr. Pathol. 56:258–266 (1990)). In contrast, it takes 260-fold less of VIP3A(a) protein to kill 50% of the black cutworm larvae, Thus, the VIP3A(a) protein displays a unique spectrum of insecticidal activities.

Both the DNA (SEQ ID NO:1) and the protein sequence of VIP3A(a) (SEQ ID NO:2) were used to search existing publicly available databases. The search was performed by using FastA (for nucleic acid), TFastA (for protein) and BLAST (for protein)(Wisconsin Package, Programe Manual, version 9 UNIX, 1997). FastA and TFastA use the method of Pearson and Lipman (Proc. Natl. Acad. Sci. U.S.A. 85:2444–2448 (1988)) to search for similarities between one sequence (query) and any group of sequences of the same type. BLAST (Basic Local Alignment Search Tool) uses the method of Altschul et al. (J. Biol. Mol. 215:403–41,1990) to search the similarities between a query sequence and all sequences in a database. The three methods combined constitute a very powerful tool to search for relationships between a query sequence and sequences in databases. The search using vip3A(a) gene sequence and VIP3A(a) protein sequence as query sequences resulted in no significant homology with any other gene or protein of the databases (GenBank, EMBL and the SWISS-PROT). Therefore, the proteins of the VIP3 class, and the genes which encode them, are novel.

HOMOLOGUES TO VIP3A(a)

It is recognized that there are multiple approaches to identifying and isolating homologues within the VIP3 class of proteins and the DNA sequences which encode them. For example, to obtain the nucleotide sequence encoding a protein which is a member of the VIP3 class, cosmid clones, which express the protein, can be isolated from a genomic library. From larger active cosmid clones, smaller subclones can be made and tested for activity. In this manner, clones which express an active VIP3 protein can be sequenced to determine the nucleotide sequence of the gene. Then, an amino acid sequence can be deduced for the protein. For general molecular methods, see, for example, Molecular Cloning, A Laboratory Manual, Second Edition, Vols. 1–3, Sambrook et al. (eds.) Cold Spring Harbor Laboratory Press, Cold Spring Harbor, N.Y. (1989), and the references cited therein.

The present invention also encompasses nucleotide sequences from organisms other than Bacillus, where the nucleotide sequences can be isolated by hybridization with the nucleotide sequences of vip3A(a). Proteins encoded by such nucleotide sequences can be tested for pesticidal activity. The invention also encompasses the proteins encoded by the nucleotide sequences. Furthermore, the invention encompasses proteins obtained from organisms other than Bacillus wherein the protein cross-reacts with antibodies raised against the proteins of the invention. Again the isolated proteins can be assayed for pesticidal activity by the methods disclosed herein or by other methods well-known in the art.

Genes homologous to vip3A(a) can also be identified by means of Southern analysis of DNA isolated from different biological sources. Total DNA can be isolated from any organism (see Ausubel, F. et al Current Protocols in Molecular Biology, 1988), restriction digested, run in agarose gels and blotted onto either nitrocellulose or nylon filters. These filters can be probed with full or partial-length coding sequences of the vip3A(a) gene. At high stringent hybridization and washing conditions only the genes with a similarity to the vip3A(a) higher than 80% will be identified. These high stringent conditions consist of an overnight hybridization at 68° C in a variety of buffers (Ausubel, F. et al. Current Protocols in Molecular Biology, 1988), followed by 2 washes of 10 min each at 68° C. in 2×standard saline citrate, SSC,/0.1% SDS, one wash of 10 min at 68° C. in 1×SSC/0.1% SDS, and one wash of 5 min at 68° C. in 0.1×SSC/0. 1% SDS). At low stringent hybridization and washing conditions, genes with a degree of similarity to the vip3A(a) gene as low as 30% can be identified. These low stringent conditions consist of an overnight hybridization at 52° C. followed by 2 washes of 5 min at 42° C. in 2×SSC/0.1% SDS.

Once the nucleotide sequences encoding the proteins of the VIP3 class have been isolated, they can be manipulated and used to express the protein in a variety of hosts, including microorganisms and plants.

Another means by which homologues to vip3A(a) can be identified and isolated is through the use of PCR technology. Primer sequences can be made which recognize either conserved or variable regions of the coding sequence, and then used to screen DNA samples obtained from either known or unknown strains.

Homologues to the VIP3A(a) protein can also be identified and isolated through the use of antibody cross-reaction. Either monoclonal or polyclonal antibodies can be raised against the protein and then used to screen protein preparations obtained from the strains themselves or from the medium in which they are grown. Useful methods of screening protein samples obtained in this way include but are not limited to Western analysis and ELISA analysis.

Members of the proteins of the VIP3 class include but are not limited to VIP3A(a) isolated from strain AB88 (deposited as Accession No. NRRL B-21225) as disclosed in SEQ ID NO:1–2; VIP3A(b) isolated from strain AB424 (deposited as Accession No. NRRL B-21439) as disclosed in SEQ ID NO:3–4; and VIP3A(c) isolated from strain AB51 (deposited as Accession No. NRRL B-21675) as disclosed in SEQ ID NO:5–6. All deposits were made in accordance with the Budapest Treaty by submission to the Agricultural Research Service, Patent Culture Collection (NRRL), Northern Regional Research Center, 1815 North University Street, Peoria, Ill. 61604, U.S.A. The DNA and protein sequences for the above three proteins are aligned in Tables 11–12.

Polypeptide Domains of the VIP3 Class of Proteins

It has been shown that the VIP3A(a) protein undergoes proteolytic processing when mixed with the gut fluids of insect larvae. When gut fluids isolated from black cutworm are mixed with purified VIP3A(a), four major proteolytic products derived from VIP3A(a) can be identified having a molecular weight of approximately 66, 45, 33 and 22 kDa. The 22 kDa band comprises the N-terminal portion of the VIP3A(a) protein from amino acid 1 to amino acid 198 of SEQ ID NO:2. The 66 kDa band comprises the rest of the VIP3A(a) protein from amino acid 200 to amino acid 789 of SEQ ID NO:2. Both the 45 and 33 kDa bands are derived by proteolysis from the 66 kDa band and constitute amino acid 412 to amino acid 789, and from amino acid 200 to amino acid 455, respectively, of SEQ ID NO:2. The 33 kDa band is the main component of the VIP3A(a) protein that remains after an incubation period of more than two hours. This 33 kDa "toxic core" domain (amino acids 200 to 455 of SEQ ID NO:2) of the VIP3A(a) protein retains full insecticidal properties against a broad spectrum of lepidopteran insects. Similar results are obtained when VIP3A(a) is incubated with gut fluids isolated from fall armyworm, another insect sensitive to VIP3A(a).

In addition to the toxic core domain, the VIP3A(a) protein also possesses a stabilizing domain at the C-terminus. The role of the stabilizing domain was explored using mutants of the VIP3A(a) protein and the VIP3A(c) protein, neither of which display insecticidal properties when ingested by insects known to be sensitive to VIP3A(a). When similar studies addressing the stability in black cutworm gut fluid was conducted with VIP3A(a)-mutants, in particular with a mutant of the VIP3A(a) protein that contains three point mutations located at the carboxy-terminal domain (amino acid 742(E→D); amino acid 770 (S→P); and amino acid 784 (Y→H)), it was found that the protein was completely hydrolyzed. Similar results were obtained for the VIP3A(c) (SEQ ID NO:6) protein isolated from AB51, which shares an overall identity of 96% with the VIP3A(a) protein but lacks the carboxy-terminal domain of VIP3A(a). Both the mutant and VIP3A(c) protein, however, are active against the insect cell line Sf-9. These results indicate that the function of the carboxy-terminal domain of proteins of the VIP3 class is to provide stability to the protein in the gut environment of susceptible insects.

Hybrid Toxins Comprising a VIP3 Region and a Heterologous Region

Toxins, enzymes, transcription factors, antibodies, cell binding moieties or other protein domains can be operably linked to the novel proteins of the present invention by producing in frame genetic fusions which, when translated by ribosomes, would produce a fusion protein with the combined attributes of the VIP and the other component used in the fusion. Furthermore, if the protein domain fused to the VIP has an affinity for another protein, nucleic acid, carbohydrate, lipid, or other chemical or factor, then a three-component complex can be formed. This complex will have the attributes of all of its components. A similar rationale can be used for producing four or more component complexes. These complexes are useful as insecticidal toxins, pharmaceuticals, laboratory reagents, and diagnostic reagents, etc. Examples where such complexes are currently used are fusion toxins for potential cancer therapies, reagents in ELISA assays and immunoblot analysis.

The hybrid toxins of the invention include chimeric proteins having a toxic core domain which is heterologous to the stabilizing domain. Hybrid toxins are also created by combining an antibody, or immunologically-active fragment thereof, which immunologically recognizes the VIP3 receptor with a toxic domain from other proteins. The toxin domain is obtained from a number of cytotoxic proteins. These include but are not limited to Bacillus toxins, including endotoxins and vegetative insecticidal proteins. See for example U.S. application Ser. No. 08/037,057, filed Mar. 25, 1993 and U.S. application Ser. No. 07/951,715 filed Sep. 25, 1992, herein incorporated by reference. Other toxins include catalytic ribosome inactivators such as gelonin, Pseudomonas exotoxin A or phytolaccin, (the structure of Pseudomonas exotoxin has been well characterized in Chaudhary et al., J. Biol. Chem. 265:16303–16310 (1990)); cell metabolism disrupters, such as ribonucleases, (see, for example, Mariani et al. Nature 347:737–741 (1990)); Barnase toxin (or PE-Bar), a chimeric toxin derived from Pseudomonas exotoxin A and a ribonuclease, (see, Prior et al Cell 64:1017–1023 (1991)); hydrophilic peptides that create pores in membranes (see, Frohlich and Wells, Int. J. Peptide Protein Res. 37:2–6 (1991)).

Mode of Action of VIP3A(a)

The VIP3A(a) protein has been shown to be active against a broad spectrum of plant pests. For example, histopathological observations indicate that VIP3A(a) ingestion by susceptible insects such as black cutworm (Agrotis epsilon) and fall armyworm (Spodoptera frugiperda) causes gut paralysis at concentrations as low as 4 ng/cm$^2$ of diet, with complete lysis of the gut epithelial cells resulting in larval death at concentrations above 40 ng/cm$^2$. Less susceptible insects like European corn borer (Ostrinia nubilalis) do not develop any pathology upon ingesting VIP3A(a). While the proteolytic processing of the VIP3A(a) protein by midgut fluids obtained from susceptible and non-susceptible insects is comparable, in vivo immuno-localization studies show that VIP3A(a) binding is restricted to gut cells of susceptible insects. Therefore, the insect host range for VIP3A(a) seems to be determined by its binding ability to gut cells. Histopathological observations indicate that midgut epithelial cells of susceptible insects are the primary target for the VIP3A(a) insecticidal protein and their subsequent lysis is the primary mechanism of lethality.

Programmed cell death is an active process of self-destruction that seems to be important for development and maintenance of multicellular organisms (Clem, R. J. et al. Science 254: 1388–1390 (1991)). Cells undergoing apoptosis, which is a form of programmed cell death, generate membrane-bound apoptotic bodies and activate endogenous nucleases that cleaves the chromatin into discrete fragments. SF-9 insect cells derived from S. frugiperda exposed to the VIP3A(a) protein undergo a series of cytological and molecular changes including membrane protrusions, profuse vacuolization and endonucleolysis which are indicative of an apoptotic-type of programmed cell death. Histological studies have shown that the VIP3A (a) protein targets midgut epithelial cells of susceptible insects initiating a series of cytological changes comprising profuse vacuolization and swelling prior to cell lysis and larval death. These midgut cells also experienced an endonucleolysis process when exposed to the VIP3A(a) protein as revealed by in situ detection of DNA fragmentation. These results indicate that VIP3A(a) exerts its insecticidal properties on susceptible insect cells by triggering an apoptotic-type of programmed cell death.

The Receptor for VIP3A(a) has been Isolated

The immunohistochemistry results provided above indicate that VIP3A(a) has the ability to bind to the apical membranes of midgut epithelial cells and that this binding triggers the process that will eventually end with cell lysis. This indicates that there exists one or more proteins located in the apical membrane that recognize and bind to VIP3A(a) acting as a receptor. This receptor signals the interaction with VIP3A(a) and triggers the process of apoptosis. Thus, the receptor will mediate the response of the insect cell to VIP3A(a).

To isolate this receptor, a cDNA library was screened which was made from mRNA isolated from midgut tissue of black cutworm. The objective of the screen was to identify and isolate cDNA sequences which encode proteins that will interact with VIP3A(a) in the two hybrid system (see Fields, S. and Song, O.-K. Nature 340:245–246 (1989)). This approach resulted in the identification and isolation of one cDNA whose encoded protein strongly interacted with the VIP3A(a) protein. This 1.75 Kb-long cDNA (SEQ ID NO:8) encodes a protein of approximately 48 kDa (396 amino acids; see SEQ ID NO:9). The cloned cDNA is similar in size to the mRNA encoding the cDNA as analyzed by Northern. A portion of the DNA sequence which encodes the first 5 to 20 amino acids may be missing. The following features can be identified in the cDNA encoded protein (see FIG. 1): 1) it contains a signal peptide; 2) it contains a domain with homology to the so-called death domain (Feinstein, E. et al. Trends in Biochem. 20:342–344 (1995)); and 3) it contains EGF-like motifs or repeats (Fantl, W. J. et al. Annu. Rev. Biochem. 62:453–481 (1993)). A search of protein databases using the receptor of VIP3A(a) showed homology with a family of extracellular glycoproteins known as Tenascins (Pearson, C. A. et al EMBO J. 7:2677–2681 (1988)) or Hexabrachion (Nies, D. E. et al. J. Biol. Chem. 266:2818–2823 (1991)). This family of proteins contains EGF-like repeats, interacts with multiple ligands, and performs a role in cell adhesion and/or signaling. The combination of a death domain and repeated EGF-motifs as observed in the VIP3 receptor is unique among programmed cell death receptors.

In addition, a portion of the VIP3A(a) receptor shares homology with the so-called "death domain." The death domain is a 60 to 70 amino acid long motif which is involved in protein to protein interaction and is shared by proteins with diverse cellular functions (Feinstein, E. et al. Trends in Biochem. 20:342–344 (1995)). Some of the protein members containing death domain motifs include receptors known to be associated with apoptotic processes. Some examples include the Fas receptor (Brakebush, C. et al. EMBO J. 11:943–950 (1992)) and the tumor necrosis factor (TNF) (Tartaglia, L. A. et al. Cell 74:845–853 (1993)).

Homologues to the VIP3A(a) receptor can be identified and isolated by various means, for example, by nucleic acid hybridization. Southern blot analysis can be performed on DNA samples taken from insect cells or fungal cells that has been enzyme restricted, run in agarose and blotted onto nitrocellulose and/or nylon filters. The Southern blot can be probed with the full-or partial length of the nucleic acid encoding the receptor of the VIP3A(a) protein under low stringency hybridization and washing conditions. The genes can be readily cloned and sequenced from a cDNA or genomic library. A size-selected genomic library can also be obtained to facilitate cloning of the gene(s) of interests. The technical protocols to perform the experiments outlined above are readily available (see for instance Molecular Cloning, A Laboratory Manual, Second Edition, Vols. 1–3, Sambrook et al. (eds.) Cold Spring Harbor Laboratory Press, Cold Spring Harbor, N.Y. (1989) and reference therein).

Antibodies to VIP3A(a) and its Receptor

Polyclonal and monoclonal antibodies to a VIP3 protein or its receptor, including fragments thereof which immunologically recognize a portion of either protein, are provided. The antibody and monoclonal antibodies of the present invention can be prepared by utilizing a VIP3 protein or its receptor as the antigen.

The antibodies of the invention include polyclonal and monoclonal antibodies as well as fragments thereof which retain their ability to bind a VIP3 protein or its receptor. An antibody, monoclonal antibody, or fragment thereof is said to be capable of binding a molecule if it is capable of specifically reacting with the molecule to thereby bind the molecule to the antibody, monoclonal antibody, or fragment thereof. The term "antibody" (Ab) or "monoclonal antibody" (Mab) is meant to include intact molecules as well as fragments or binding regions or domains thereof (such as, for example, Fab and F(ab)$_2$ fragments) which are capable of binding hapten. Such fragments are typically produced by proteolytic cleavage, such as papain or pepsin. Alternatively, hapten-binding fragments can be produced through the application of recombinant DNA technology or through synthetic chemistry.

Methods for the preparation of the antibodies of the present invention are generally known in the art. For example, see Antibodies, A Laboratory Manual, Ed Harlow and David Lane (eds.) Cold Spring Harbor Laboratory, New York (1988), as well as the references cited therein. Standard reference works setting forth the general principles of immunology include: Klein, J. Immunology: The Science of Cell-Noncell Discrimination, John Wiley & Sons, New York (1982); Dennett, R., et al. Monoclonal Antibodies, Mybridoma: A New Dimension in Biological Analyses, Plenum Press, New York (1980); and Campbell, A. "Monoclonal Antibody Technology," In Laboratory Techniques in Biochemistry and Molecular Biology, Vol. 13, Burdon et al. (eds.), Elsevier, Amsterdam (1984). See also, U.S. Pat. Nos: 4,609,893; 4,713,325; 4,714,681; 4,716,111; 4,716,117; and 4,720,459.

It is recognized that following the methods described herein, antibodies specific for a particular VIP3 protein or its receptor can be generated. The subset of MAb lines which possess the desired binding specificity can be used as a source of messenger RNA for cloning of the cDNA for the particular monoclonal antibody.

The cloned DNA can then be sequenced by methods known in the art. See, for example, Sambrook et al, Molecular Cloning: A Laboratory Manual, 2nd. Edition, Cold Spring Harbor Laboratory Press, New York (1989) vol. 1–3, and the references cited therein. From the nucleic acid sequence, the protein sequence of the binding region from the selected MAb can be deduced.

One use of the antibodies and monoclonal antibodies of the invention includes but is not limited to the production of hybrid toxin molecules. That is, when linked, the monoclonal antibody or antibody fragment retains its binding properties and the toxin moiety retains its cytotoxic properties.

Various methods are known for obtaining antibody genes. One method is to clone a random library of antibody genes in a phage and screen the library for ability to bind to a VIP3 protein or its receptor. Another available approach is to generate monoclonal antibodies which bind to a VIP3 protein or its receptor and then clone the antibody genes from such lines. For the present example, the second method is used. Antibody genes can be cloned from hybridoma cells using primers to conserved DNA sequences within the constant regions and the framework regions of the variable regions and amplified for cloning using the polymerase chain reaction (PCR). See generally, Mullis et al, Meth. Enzymol., 155:335–350 (1987); Erlich, (ed.), PCR Technology, Stockton Press (New York 1989). A database of mouse heavy chain and light chain sequences compiled by Kabat et al, U.S. Dept Health and Human Services, U.S. Government Printing Offices (1991) has been successfully used to generate both isotype specific and degenerate primers for cloning antibody genes. (Jones et al Bio/technology 9:88–89 (1991)). Additionally, techniques are well known for cloning of smaller fragments of antibodies (Fab) which possess the binding properties of the original antibody. Complete antibodies are large molecules (150 kDa), but much smaller Fab and Fv antigen-binding fragments (12 kDa–50 kDa) have been shown to retain full binding affinity. Single chain Fv fragments (scFv) in which Vh and Vl domains are linked by a hydrophilic and flexible peptide have been used successfully to target enzymes and toxins to specific cells (Bird, Science 423:423–426 (1988); Huston, PNAS 85:5879–5883 (1988)). Single Vh domains (Dabs) and single complementary determining regions as small as 20 amino acids in length, called minimal recognition units (m.r.u.), have also been used for antigen binding (Ward, Nature 341:544–546 (1989); Taub, J. Biol. Chem 264:259–265 (1989); Williams, PNAS 86:5537–5541 (1989)). Thus, it is possible to reduce the binding domain specific for a VIP3 or its receptor to a very small size.

Polymerase chain reaction technology and specific oligonucleotide primers are used to clone immunoglobulin genes or regions from immunoglobin genes. PCR primers specific for both the heavy and light chains of IgM and the three IgG isotypes were selected from the Kabat database described above. Primers for the region encoding the $NH_2$-terminal end of the mature variable region were designed to initiate at the first framework region and were made with some degeneracy to allow these to be used as "universal primers". The 3' primers used for the specific PCR amplification of the variable regions were designed from conserved sequences of the first constant domain (CH1) of both the light and heavy chains. A different 3' primer is used for immunoglobulin isotypes IgG1, IgG3, and IgM. Isotypes IgG2A and IgG2B can be amplified with the same primers used for IgG1. Antibody variable regions are cloned into a light and heavy chain expression vector containing an endoplasmic reticulum signal peptide and the constant regions of IgG1 light and heavy chains, respectively.

Primer sequences used for the PCR cloning of the mouse immunoglobulin light and heavy variable regions are available in the published literature (Coloma et al. Bio/Techniques 11: 152–156 (1991); Jones et al Bio/Technology 9:88–89 (1991)). Oligonucleotides were made on an Applied Biosystems DNA synthesizer 380B (Applied Biosystems, Foster City, Calif.) using standard conditions as described below. The PCR primers incorporate restriction sites and, after amplification and digestion, can be cloned into a plant expression vector under the control of a plant-expressible promoter. Restriction sites were chosen that were known to be absent in sequenced antibody genes.

Another use of the polyclonal and/or monoclonal antibodies of the invention includes the stimulation of apoptosis by targeting the receptor to Vip3A with antibodies. The interaction of antibodies raised against cell surface-located proteins that are involved in controlling the cell growth result in the induction of apoptosis by means of preventing the said receptor from binding to its natural ligand(s). For instance, the anti-APO-1 antibody completely blocks proliferation of leukemia cells bearing the APO-1 protein and triggers apoptosis in these cells (Trauth, B. C. et al Science 245:301–305 (1989)). Also, the activity resulting from the interaction between a given receptor and a ligand is mimicked by substituting the ligand for antibodies raised against the receptor. For instance, the addition of certain anti-Fas antibodies to cells bearing the Fas receptor in their cell surfaces will mediate apoptosis in a similar fashion as when the ligand of the Fas receptor is added (Itoh, N. et al. Cell 66:233–243 (1991)).

The receptor to Vip3A(a) isolated from black cutworm shares homology with a family of extracelular glycoproteins known as Tenascins, and in particular with Tenascin-X (Bristow, J. et al. J. Cell Biol. 122:265–278 (1993)). Tenascin-Xs are known to be involved in cell-to-cell adhesion and signaling. Lack of functionality of Tenascin-X either by mutation or by removal of the gene leads to lethality. Therefore, antibodies raised against different domains of the receptor to Vip3A(a) either effectively block the receptor from binding to its ligand(s) or mimic the interaction of the Vip3A(a) protein triggering apoptosis. This approach is extended to different receptors with similar biological functions. In this sense, antibodies raised against insect cell receptors involved in crucial cell growth and interaction processes lead to induction of apoptosis and are used as an strategy to control insects.

Screening for Novel Insecticidal Activities whose Mode of Action is Apoptosis

The materials described in this invention are used to screen for chemical ligands that have pesticidal properties triggering apoptotic responses. Chemical ligands include small organic molecules, peptides, and proteins. In one embodiment of the invention, insect cell lines are used as model organisms for insects to screen for compounds that are insecticidal as a consequence of their ability to induce apoptosis. These cell lines are handled in a high-throughput screening format where the cells are grown in multi-well plates and are exposed to a variety of compounds. Yeast is also used as a model organism. Using procedures described herein or known in the art, determining whether a compound is pesticidal as a consequence of inducing apoptosis is accomplished.

One means by which to identify compounds that trigger apoptotic responses through interaction with a known receptor is to resort to identified receptors involved in the signal transduction pathway triggered in apoptotic insect cell lines. These receptors are transformed into heterologous cell lines creating isogenic lines with one of them containing a gene for expression of a specific receptor and another one which does not either possess, or express, such a gene. These cell lines are handled in a high-throughput screening format whereby the transformed cell lines expressing the receptor have a differential response against compounds that trigger apoptosis through their specific interaction with said receptor.

Also encompassed by the present invention is the characterization of biochemical and/or molecular markers that specifically identify an insect cell line undergoing apoptosis. For example, it is possible to isolate specific cDNAs induced during an apoptotic process in specific insect cell lines. Although the death core pathway seems to be phylogenetically conserved (Nagata, S. Cell 88:355–365 (1997)), the signal transduction pathway from the receptor to the death core pathway is subject to variation across organisms. Messenger RNAs differentially expressed in insect cells undergoing apoptosis are identified by a number of techniques readily available such as differential display (Bauer, D. et al. Nucleic Acid Res. 21:4272–4280 (1993)) or subtractive libraries (Sommer, H. et al EMBO J. 9:605–613 (1990)). The differentially expressed cDNA-encoded proteins are used as markers for apoptosis in specific insect cell lines.

Transgenic Plants Comprising a DNA Sequence Encoding a Protein of the VIP3 Class A host plant expressing at least one of the sequences of the invention has enhanced resistance to attack by plant pests and is thus better equipped to withstand crop losses associated with such attack. By plant is meant any plant species which can be genetically transformed by methods known in the art. Methods known in the art for plant transformation are discussed below. Host plants include, but are not limited to, those species previously listed as target crops.

PLANT EXPRESSION CASSETTES

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence. It is further recognized that promoters or terminators of the VIP3 genes can be used in expression cassettes.

Toxin genes derived from microorganisms may also differ from plant genes. Plant genes differ from genes found in microorganisms in that their transcribed RNA does not possess defined ribosome binding site sequence adjacent to the initiating methionine. Consequently, microbial genes can be enhanced by the inclusion of a eukaryotic consensus translation initiator at the ATG (Kozak, Cell 44:283–292

(1986)). Clontech (1993/1994 catalog, page 210) has suggested the sequence GTCGACCATGGTC as a consensus translation initiator for the expression of the *E. coli* uidA gene in plants. Further, Joshi (Nucleic Acids Res. 15: 6643–6653 (1987)) has compared many plant sequences adjacent to the ATG and suggests the consensus TAAACA ATGGCT. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. By surveying the sequence of maize genes present in the GenBank/EMBL database it can be discerned which nucleotides adjacent to the ATG should be modified to enhance translation of the toxin gene introduced into maize.

In addition, it has been shown that removal of illegitimate splice sites can enhance expression and stability of introduced genes. Genes cloned from non-plant sources and not optimized for expression in plants may contain motifs which can be recognized in plants as 5' or 3' splice sites. Consequently, the transcription process can be prematurely terminated, generating truncated or deleted mRNA. The toxin genes can be engineered to remove these illegitimate splice sites using multiple techniques. For example, several available methods can be utilized to identify potential splice sites in a DNA sequence. First, potential splice sites may be identified by computer analysis of the DNA sequence. Consensus sequences which identify splice sites are known in the art. See, for example, Goodall, G. J. and Filipowicz, W., EMBO J. 10, 2635–2644 (1991) and Brown, J. W. S., Nucleic Acids Research 14, 9549–9559 (1986). Alternately, one can identify splice sites actually processed by a plant by comparing PCR analysis of cDNA derived from the gene with actual gene products. Shorter than expected products are indicative of splicing. Such smaller products are then cloned and sequenced and the exact location of the splice determined. It is also recognized that a combination of computer searching and PCR analysis can be utilized.

The novel toxin genes of the present invention, either as their native sequence or as optimized synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. Preferred constitutive promoters include the CaMV 35S and 19S promoters (Fraley et al., U.S. Pat. No. 5,352,605, issued Oct. 4, 1994). An additionally preferred promoter is derived from any one of several of the actin genes, which are known to be expressed in most cell types. The promoter expression cassettes described by McElroy et al (Mol. Gen. Genet. 231: 150–160 (1991)) can be easily modified for the expression of the novel toxin gene and are particularly suitable for use in monocotyledonous hosts.

Yet another preferred constitutive promoter is derived from ubiquitin, which is another gene product known to accumulate in many cell types. The ubiquitin promoter has been cloned from several species for use in transgenic plants (e.g. sunflower—Binet et al Plant Science 79: 87–94 (1991), maize—Christensen et al Plant Molec. Biol. 12: 619–632 (1989)). The maize ubiquitin promoter has been developed in transgenic monocot systems and its sequence and vectors constructed for monocot transformation are disclosed in the patent publication EP 0 342 926. The ubiquitin promoter is suitable for the expression of the novel toxin gene in transgenic plants, especially monocotyledons.

Tissue-specific or tissue-preferential promoters useful for the expression of the novel toxin gene in plants, particularly maize, are those which direct expression in root, pith, leaf or pollen. Such promoters are disclosed in U.S. Ser. No. 07/951,715 and published as WO 93/07278, herein incorporated by reference in its entirety. Chemically inducible promoters useful for directing the expression of the novel toxin gene in plants are disclosed in U.S. Ser. No. 08/181, 271, herein incorporated by reference in its entirety.

In addition to promoters, a variety of transcriptional terminators are also available for use in chimeric gene construction using the novel toxin gene of the present invention. Transcriptional terminators are responsible for the termination of transcription beyond the transgene and its correct polyadenylation. Appropriate transcriptional terminators and those which are known to function in plants include the CaMV 35S terminator, the tml terminator, the nopaline synthase terminator, the pea rbcS E9 terminator and others known in the art. These can be used in both monocotyledons and dicotyledons.

Numerous sequences have also been found to enhance gene expression from within the transcriptional unit and these sequences can be used in conjunction with the novel toxin gene of this invention to increase their expression in transgenic plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (Callis et al, Genes Develop. 1: 1183–1200 (1987)). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "Ω-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15; 65–79 (1990))

The 5' regulatory region of the expression cassette may also include other enhancing sequences. Numerous sequences have been found to enhance gene expression in transgenic plants. For example, a number of non-translated leader sequences derived from viruses are known to enhance expression. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15:8693–8711 (1987); Skuzeski et al. *Plant Molec. Biol.* 15:65–79 (1990)). Other leaders known in the art include but are not limited to:

Picornavirus leaders, for example, EMCV leader (Encephalomyocarditis 5' noncoding region) (Elroy-Stein, O., Fuerst, T. R., and Moss, B. *PNAS USA* 86:6126–6130 (1989));

Potyvirus leaders, for example, TEV leader (Tobacco Etch Virus) (Allison et al., (1986); MDMV leader (Maize Dwarf Mosaic Virus); *Virology,* 154:9–20);

Human immunoglobulin heavy-chain binding protein (BiP) leader, (Macejak, D. G., and Sarnow, P., *Nature,* 353: 90–94 (1991);

Untranslated leader from the coat protein mRNA of alfalfa mosaic virus (AMV RNA 4), (Jobling, S. A., and Gehrke, L., *Nature*, 325:622–625 (1987);

Tobacco mosaic virus leader (TMV), (Gallie, D. R. et al., *Molecular Biology of RNA*, pages 237–256 (1989); and Maize Chlorotic Mottle Virus leader (MCMV) (Lommel, S. A. et al., *Virology*, 81:382–385 (1991). See also, Della-Cioppa et al., *Plant Physiology*, 84:965–968 (1987).

Various intron sequences have been shown to enhance expression when added to the 5' regulatory region, particularly in monocotyledonous cells. For example, the introns of the maize Adh1 gene have been found to significantly enhance the expression of the wild-type gene under its cognate promoter when introduced into maize cells (Callis et al., *Genes Develop.* 1:1183–1200(1987)).

In addition to promoters, a variety of 3' transcriptional terminators are also available for use in the present invention. Transcriptional terminators are responsible for the termination of transcription and correct mRNA polyadenylation. Appropriate transcriptional terminators and those which are known to function in plants include the CaMV 35S terminator, the tml terminator, the nopaline synthase terminator, the pea rbcS E9 terminator and others known in the art. These can be used in both monocotyledons and dicotyledons.

OPITMIZING vip3 GENES FOR PLANT EXPRESSION

The pesticidal genes of the invention can be optimized for enhanced expression in plants. See, for example, EPA 0359472; EPA 0385962; WO 91/16432; and, Perlak et al., Proc. Natl. Acad. Sci. 88:3324–3328 (1991). In this manner, the coding sequences can be synthesized which are optimized for plant expression.

In one embodiment of the invention the vip3A(a) is made according to the procedure disclosed in U.S. Ser. No. 07/951,715, herein incorporated by reference. In this procedure, maize preferred codons, i.e., the single codon which most frequently encodes that amino acid in maize, are used. The maize preferred codon for a particular amino acid may be derived, for example, from known gene sequences from maize. Maize codon usage for 28 genes from maize plants is found in Murray et al., Nucleic Acids Research 17: 477–498 (1989), the disclosure of which is incorporated herein by reference. Examples of synthetic sequences made with maize optimized codons are set forth in SEQ ID NO:7 (VIP3A(a)), in SEQ ID NO:19 (VIP3A(b)), and in SEQ ID NO:20 (VIP3A(c)).

In this manner, the nucleotide sequences can be optimized for expression in any plant.

It is recognized that all or any part of the gene sequence may be optimized or synthetic. That is, synthetic or partially optimized sequences may also be used.

PLANT TRANSFORMATION

The recombinant DNA molecules can be introduced into the plant cell in a number of art-recognized ways. Those skilled in the art will appreciate that the choice of method might depend on the type of plant, i.e. monocot or dicot, targeted for transformation. Suitable methods of transforming plant cells include microinjection (Crossway et al., BioTechniques 4:320–334 (1986)), electroporation (Riggs et al, Proc. Natl. Acad. Sci. U.S.A. 83:5602–5606 (1986), Agrobacterium-mediated transformation (Hinchee et al., Biotechnology 6:915–921 (1988)), direct gene transfer (Paszkowski et al., EMBO J. 3:2717–2722 (1984)), and ballistic particle acceleration using devices available from Agracetus, Inc., Madison, Wis. and Dupont, Inc., Wilmington, Del. (see, for example, Sanford et al., U.S. Pat. 4,945,050; and McCabe et al., Biotechnology 6:923–926 (1988); see also Weissinger et al., Annual Rev. Genet. 22:421–477 (1988); Sanford et al., Particulate Science and Technology 5:27–37 91987)(onion); Christou et al., Plant Physiol. 87:671–674 (1988)(soybean); McCabe et al., Bio/Technology 6:923–926 (1988)(soybean); Datta et al., Bio/Technology 8:736–740 (1990)(rice); Klein et al., Proc. Natl. Acad. Sci. U.S.A., 85:4305–4309 (1988)(maize); Klein et al., Bio/Technology 6:559–563 (1988)(maize); Klein et al., Plant Physiol. 91:440–444 (1988)(maize); Fromm et al., Bio/Technology 8:833–839 (1990); and Gordon-Kamm et al., Plant Cell 2:603–618 (1990)(maize); Svab et al. Proc. Natl. Acad. Sci. U.S.A. 87: 8526–8530 (1990) (tobacco chloroplast); Koziel et al. (Biotechnology 11: 194–200 (1993)) (maize); Shimamoto et al Nature 338: 274–277 (1989) (rice); Christou et al. Biotechnology 9: 957–962 (1991) (rice); European Patent Application EP 0 332 581 (orchardgrass and other Pooideae); Vasil et al (Biotechnology 11: 1553–1558 (1993) (wheat); Weeks et al. (Plant Physiol. 102: 1077–1084 (1993) (wheat); Wan et al (Plant Physiol. 104: 37–48 (1994)(barley)); Umbeck et al., (Bio/Technology 5: 263–266 (1987)(cotton); Casas, A. M. et al. Proc. Natl. Acad. Sci. U.S.A. 90: 11212–11216 (1991) (sorghum).

One particularly preferred set of embodiments for the introduction of the expression cassettes of the present invention into maize by microprojectile bombardment is described in U.S. Ser. No. 08/008,374, herein incorporated by reference in its entirety. An additional preferred embodiment is the protoplast transformation method for maize as disclosed in European Patent Application EP 0 292 435, as well as in U.S. Pat. No. 5,350,689, hereby incorporated by reference in its entirety. One particularly preferred set of embodiments for the introduction of the expression cassettes of the present invention into wheat by microprojectile bombardment can be found in U.S. Pat. No. 5,610,042 herein incorporated by reference in its entirety.

Transformation of plants can be undertaken with a single DNA molecule or multiple DNA molecules (i.e. co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

Numerous transformation vectors are available for plant transformation, and the genes of this invention can be used in conjunction with any such vectors. The selection of vector for use will depend upon the preferred transformation technique and the target species for transformation.

Many vectors are available for transformation using *Agrobacterium tumefaciens*. These typically carry at least one T-DNA border sequence and include vectors such as pBIN19 (Bevan, Nucl. Acids Res. (1984)). In one preferred embodiment, the novel toxin gene of the present invention may be inserted into either of the binary vectors pCIB200 and pCIB2001 for use with Agrobacterium. These vector cassettes for Agrobacterium-mediated transformation can be constructed in the following manner. pTJS75kan was created by NarI digestion of pTJS75 (Schmidhauser & Helinski, J Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982); Bevan et al., Nature 304: 184–187 (1983); McBride et al., Plant Molecular Biology 14: 266–276 (1990)). XhoI linkers were ligated to the EcoRV fragment of pCIB7 which contains the left and right T-DNA borders, a plant selectable nos/nptII chimeric gene and the pUC polylinker (Rothstein et al., Gene 53: 153–161 (1987)), and the XhoI-digested fragment was cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 which created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

An additional vector useful for Agrobacterium-mediated transformation is the binary vector pCIB10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al. (Gene 53: 153–161 (1987)). Various derivatives of pCIB10 have been constructed which incorporate the gene for hygromycin B phosphotransferase described by Gritz et al (Gene 25: 179–188 (1983)). These derivatives enable selection of transgenic plant cells on hygromycin only (pCIB743), or hygromycin and kanamycin (pCIB715, pCIB717).

Methods using either a form of direct gene transfer or Agrobacterium-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention unless the expression of this resistance and its biochemical activity interferes with the choice of protoxin to toxin conversion chosen for use in creating conditional fertility.

For certain plant species, different antibiotic or herbicide selection markers may be preferred. Selection markers used routinely in transformation include the nptli gene which confers resistance to kanamycin and related antibiotics (Messing & Vierra, *Gene* 19: 259–268 (1982); Bevan et al., *Nature* 304:184–187 (1983)), the bar gene which confers resistance to the herbicide phosphinothricin (White et al., *Nucl Acids Res* 18:1062 (1990), Spencer et al., *Theor Appl Genet* 79:625–631(1990)), the hph gene which confers resistance to the antibiotic hygromycin (Blochinger & Diggelmann, *Mol Cell Biol* 4: 2929–2931), the dhfr gene, which confers resistance to methotrexate (Bourouis et al, *EMBO J.* 2: 1099–1104 (1983)), the mannose phosphate isomerase gene, which allows selection on mannose as a carbon source (EP 530 129,WO 94/20627).

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the *E. coli* GUS gene and the CaMV 35S transcriptional terminator and is described in the PCT published application WO 93/07278, herein incorporated by reference. The gene providing resistance to phosphinothricin is the bar gene from *Streptomyces hygroscopicus* (Thompson et al. EMBO J. 6: 2519–2523 (1987)). This vector is suitable for the cloning of plant expression cassettes containing their own regulatory signals. Another useful selectable marker is obtained by operably linking a ubiquitin promoter, a synthetic PAT gene and a nos terminator. Once example of a vector comprising this marker is the plasmid pCIB9804.

An additional transformation vector is pSOG35 which utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp; see Dennis et al., Nucleic Acid Res. 12:3983–4000 (1984)) and 18 bp of the GUS untranslated leader sequence (see Jefferson et al., Proc. Nat. Acad. Sci. U.S.A. 83: 8447–8451 (1986). A 250 bp fragment encoding the *E. coli* dihydrofolate reductase type II gene was also amplified by PCR and these two PCR fragments were assembled with a SacI-PstI fragment from pBI221 (Clontech) which comprised the pUC19 vector backbone and the nopaline synthase terminator. Assembly of these fragments generated pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus check (MCMV) generated the vector pSOG35. pSOG19 and pSOG35 carry the pUC gene for ampicillin resistance and have HindIII, SphI, PstI and EcoRI sites available for the cloning of foreign sequences.

Another transformation vector is the vector pGL2 (Shimamoto et al. Nature 338, 274–276 (1989)) which contains the Streptomyces hygromycin phosphotransferase gene (hpt) operably linked to the 35S promoter and 35S terminator sequences.

Transgenic plants can also be identified through the use of a scorable marker. Examples of scorable markers useful in the invention are β-glucuronidase, green fluorescent protein, and the C1 and B-peru regulatory genes of the maize anthocyanin pathway. In addition, transgenic plants expressing a VIP3 protein can be identified by screening them for insecticidal activity without the need for either scorable or selectable markers.

Transformation of maize with a DNA sequence encoding a protein of the VIP3 class according to any of the above methods can be readily achieved by microprojectile bombardment of either immature zygotic embryos or serially-propagatable Type I embryogenic callus.

For transformation using immature zygotic embryos, ears are self-pollinated and immature zygotic embryos are obtained approximately 10 days later. Approximately eight hundred immature zygotic embryos are divided among different target plates containing a medium capable of inducing and supporting the formation of embryogenic callus. The immature zygotic embryos are transferred immediately to the same medium but containing 12% sucrose. After 5 hours, the immature zygotic embryos are bombarded with a plasmid or plasmids using the PDS-1000/He device from Bio-Rad. The plasmid or plasmids comprise a selectable marker, such as a gene conferring resistance to phosphinothricin, or a scorable marker, such as green fluorescent protein, and a gene encoding a protein of the VIP3 class prepared for delivery to and expression in maize according to the above description. The plasmid or plasmids are precipitated onto 1 μm gold particles essentially according to the published procedure from BioRad. The particles are delivered using a burst pressure of 1550 psi of helium. Each target plate is shot twice with the plasmid and gold particle preparation. Since in one embodiment of the invention the plasmid or plasmids comprise a chimeric gene coding for resistance to phosphinothricin this substance could be used to select transformed cells in vitro. If used, the selection agent is applied at 10 mg/L on the day of gene delivery and increased to 40 mg/L after approximately one month. The embryogenic callus so obtained may be regenerated in the presence of the selection agent phosphinothricin if the selectable marker is used. Plants are obtained from the selected embryogenic callus lines. The regenerated plants are assayed for resistance to a susceptible insect. All the plants that are resistant to the insect also express the introduced chimeric gene encoding a protein or proteins of the VIP3 class as evidenced by the detection of VIP3 protein in the plant using an ELISA assay. Plants resistant to the insect and expressing the VIP3 protein are transformed.

For transformation of maize using Type I embryogenic callus, the callus is obtained from immature zygotic embryos using standard culture techniques. For gene delivery, approximately 300 mg of the Type I callus is prepared by either chopping with a scalpel blade or by subculturing 3–5 days prior to gene delivery. Prior to gene delivery, the prepared callus is placed onto semi-solid culture medium again containing 12% sucrose. After approximately 4 hours, the tissue is bombarded using the PDS-1000/He Biolistic device from BioRad. The plasmid or plasmids comprise a selectable marker, such as a gene conferring resistance to phosphinothricin, or a scorable marker, such as green fluorescent protein, and a gene encoding a protein of the VIP3 class prepared for delivery to and expression in maize according to the above description. The plasmids are precipitated onto 1 μm gold particles using essentially the standard protocol from BioRad. Approximately 16 hours after gene delivery the callus is transferred to standard culture medium containing 2% sucrose and, if the selectable marker is used, to 1 mg/L phosphinothricin. The callus is subcultured on selection for 8 weeks, after which surviving and growing callus is transferred to standard regeneration medium for the production of plants. The regenerated plants are assayed for resistance to a susceptible insect. All the plants that are resistant to the insect also express the introduced chimeric gene encoding a protein of the VIP3 class as evidenced by the detection of VIP3 protein in the plant using an ELISA assay. Plants resistant to the insect and expressing a protein of the VIP3 class are transformed.

SUPPLEMENTAL INSECT CONTROL PRINCIPLES

The pesticidal proteins of the invention can be used in combination with Bt δ-endotoxins or other insecticidal proteins to increase insect target range. Furthermore, the use of the VIPs of the present invention in combination with Bt δ-endotoxins or other insecticidal principles of a distinct nature has particular utility for the prevention and/or management of insect resistance.

The various insecticidal crystal proteins from *Bacillus thuringiensis* have been classified based upon their spectrum of activity and sequence similarity. The classification put forth by Höfte and Whiteley, Microbiol. Rev. 53: 242–255 (1989) placed the then known insecticidal crystal proteins into four major classes. Generally, the major classes are defined by the spectrum of activity, with the Cry1 proteins active against Lepidoptera, Cry2 proteins active against both Lepidoptera and Diptera, Cry3 proteins active against Coleoptera, and Cry4 proteins active against Diptera.

Within each major class, the δ-endotoxins are grouped according to sequence similarity. The Cry1 proteins are typically produced as 130–140 kDa protoxin proteins which are proteolytically cleaved to produce active toxin proteins about 60–70 kDa. The active portion of the δ-endotoxin resides in the $NH_2$-terminal portion of the full-length molecule. Höfte and Whiteley, supra, classified the then known Cry1 proteins into six groups, 1Aa, 1Ab, 1Ac, 1B, 1C, and 1D. Since then, proteins classified as Cry1Ea, Cry1Fa, Cry9A, Cry9C and Cry9B have also been characterized.

The spectrum of insecticidal activity of an individual δ-endotoxin from *Bacillus thuringiensis* tends to be quite narrow, with a given δ-endotoxin being active against only a few insects. Specificity is the result of the efficiency of the various steps involved in producing an active toxin protein and its subsequent ability to interact with the epithelial cells in the insect digestive tract. In one preferred embodiment, expression of VIPs in a transgenic plant is accompanied by the expression of one or more Bt δ-endotoxins. Particularly preferred Bt δ-endotoxins are those disclosed in U.S. application Ser. No. 07/951,715, herein incorporated by reference.

It is well known that many δ-endotoxin proteins from *Bacillus thuringiensis* are actually expressed as protoxins. These protoxins are solubilized in the alkaline environment of the insect gut and are proteolytically converted by proteases into a toxic core fragment (Höfte and Whiteley, Microbiol. Rev. 53: 242–255 (1989)). For δ-endotoxin proteins of the CryI class, the toxic core fragment is localized in the N-terminal half of the protoxin. It is within the scope of the present invention that genes encoding either the full-length protoxin form or the truncated toxic core fragment of the novel toxin proteins can be used in plant transformation vectors to confer insecticidal properties upon the host plant.

Other insecticidal principles include protease inhibitors (both serine and cysteine types), lectins, α-amylase, peroxidase and cholesterol oxidase. Other VIP genes, such as vip 1A(a) and vip2A(a) as disclosed in U.S. Ser. No. 08/463,483 and herein incorporated by reference, are also useful in the present invention.

This co-expression of more than one insecticidal principle in the same transgenic plant can be achieved by genetically engineering a plant to contain and express all the genes necessary. Alternatively, a plant, Parent 1, can be genetically engineered for the expression of VIPs. A second plant, Parent 2, can be genetically engineered for the expression of a supplemental insect control principle. By crossing Parent 1 with Parent 2, progeny plants are obtained which express all the genes introduced into Parents 1 and 2.

Recombinant Microorganisms Comprising Genes and Proteins of the VIP3 Class

It is recognized that the isolated genes of the present invention which encode a protein of the VIP3 class can be transferred into any microbial host and confer their insecticidal properties upon that host. Alternate hosts for the novel genes of the present invention can be selected as suitable for cloning purposes, for purposes of characterizing the form and function of the gene or encoded protein, for use as a fermentation host to increase production of the toxin protein, for purposes of delivering at least one of the toxin proteins more effectively to the target insect pest, or introduction of the novel toxin gene into insect pathogens such as baculovirus (a nuclear polyhedrosis virus, e.g. *Autographica californica*) to improve their effectiveness.

It is envisioned that said alternate host would be applied to the environment or plants or animals for insect control. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Bacillus, Caulobacter, Agmenellum, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as Bacillus spp., *Pseudomonas syringae, Pseudomonas fluorescens, Serratia marcescens, Acetobacter xylinum,* Agrobacteria, *Rhodopseudomonas spheroides, Xanthomonas campestris, Rhizobium melioti, Alcaligenes entrophus, Clavibacter xyli* and *Azotobacter vinlandii;* and phytosphere yeast species such as *Rhodotorula rubra, R. glutinis, R. marina, R. aurantiaca, Cryptococcus albidus, C. difuens, C. laurentii, Saccharomyces rosei, S. pretoriensis, S. cerevisiae, Sporobolomyces rosues, S. odorus, Kluyveromyces veronae,* and *Aureobasidium pollulans.* Of particular interest are the pigmented microorganisms.

Suitable host cells, where the pesticide-containing cells will be treated to prolong the activity of the toxin in the cell when the then treated cell is applied to the environment of the target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such a Saccharomyces and Schizosaccharromyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities.

Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula sp., Aureobasidium sp., Saccharomyces sp.,* and *Sporobolomyces sp.;* phylloplane organisms such as *Pseudomonas, Erwinia sp.* and *Flavobacterium sp.;* or such other organisms as Escherichia, *LactoBacillus sp., Bacillus sp.,* and the like. Specific organisms include *Pseudomonas aeurginosa, Pseudomonas fluorescens, Saccharomyces cerevisiae, Bacillus thuringiensis, Escherichia coli, Bacillus subtilis,* and the like.

A number of ways are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,33 1; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

The novel genes or recombinant forms thereof can be transformed into such alternate hosts using a variety of art recognized methods. One such preferred method is electroporation of microbial cells, as described, for example, by the method of Dower (U.S. Pat. No. 5,186,800). Another preferred method is that of Schurter et al. (Mol. Gen. Genet. 218: 177–181 (1989)), which is also disclosed in U.S. Ser. No. 07/353,565 which is incorporated herein in its entirety.

Genes encoding the VIP3 class of proteins can be introduced into microorganisms that multiply on plants (epiphytes) or in plants (endophytes) to deliver proteins of the VIP3 class to potential target pests. Many bacterial species are capable of living in the vascular tissues of plants. Most of these endophytes and epiphytes appear to have little physiological impact on plant growth and productivity.

Root colonizing bacteria, for example, can be isolated from the plant of interest by methods known in the art. Specifically, a *Bacillus cereus* strain which colonizes roots could be isolated from roots of a plant (for example see J. Handelsman, S. Raffel, E. Mester, L. Wunderlich and C. Grau, Appl. Environ. Microbiol. 56:713–718, (1990)). Vip3 genes can also be introduced into a root colonizing *Bacillus cereus* by standard methods known in the art. Specifically, a gene encoding a protein of the VIP3 class derived from strain AB88 can be introduced into a root colonizing *Bacillus cereus* by means of conjugation using standard methods (J. Gonzalez, B. Brown and B. Carlton, Proc. Natl. Acad. Sci. 79:6951–6955, (1982)).

Also, the novel genes of the invention can be introduced into the root colonizing Bacillus by means of electrotransformation. For example, vip3A(a) can be cloned into a shuttle vector, for example, pHT3101 (D. Lereclus et al., FEMS Microbiol. Letts., 60:211–218 (1989)). The shuttle vector pHT3101 containing the coding sequence can then be transformed into the root colonizing Bacillus by means of electroporation (D. Lereclus et al. 1989, FEMS Microbiol. Letts. 60:211–218). It is also possible to use the cotton colonizing *Bacillus megaterium.*

Another example is afforded by the endophyte *Clavibacter xyli,* which is from a genus/species known contain phytopathogenic bacteria which cause plant stunting. This bacterium can grow to very high levels in the vascular system of plants. A δ-endotoxin was introduced into this endophyte, which when inoculated into a plant, provided good control of corn borer. Other endophytes are also known.

Expression systems can be designed so that VIP3 proteins are secreted outside the cytoplasm of gram negative bacteria, *E. coli*, for example. Advantages of having VIP3 proteins secreted are (1) it can increase the level of VIP3 protein expressed and (2) can aid in efficient purification of VIP3 protein.

VIP3 proteins can be made to be secreted in *E. coli*, for example, by fusing an appropriate *E. coli* signal peptide to the amino-terminal end of the VIP3 signal peptide or replacing the VIP3 signal peptide with the *E. coli* signal peptide. Signal peptides recognized by *E. coli* can be found in proteins already known to be secreted in *E. coli*, for example the OmpA protein (J. Ghrayeb, H. Kimura, M. Takahara, Y. Masui and M. Inouye, EMBO J., 3:2437–2442 (1984)). OmpA is a major protein of the *E. coli* outer membrane and thus its signal peptide is thought to be efficient in the translocation process. Also, the OmpA signal peptide does not need to be modified before processing as may be the case for other signal peptides, for example lipoprotein signal peptide (G. Duffaud, P. March and M. Inouye, Methods in Enzymology. 153:492 (1987)).

Specifically, unique BamHI restriction sites can be introduced at the amino-terminal and carboxy-terminal ends of the VIP coding sequences using standard methods known in the art. These BarmHI fragments can be cloned, in frame, into the vector pIN-III-ompA1, A2 or A3 (J. Ghrayeb, H. Kimura, M. Takahara, H. Hsiung, Y. Masui and M. Inouye, EMBO J., 3:2437–2442 (1984)) thereby creating ompA:VIP fusion gene which is secreted into the periplasmic space. The other restriction sites in the polylinker of pIN-III-ompA can be eliminated by standard methods known in the art so that the VIP3 amino-terminal amino acid coding sequence is directly after the ompA signal peptide cleavage site. Thus, the secreted VIP3 sequence in *E. coli* would then be identical to the native VIP3 sequence.

When the VIP3 native signal peptide is not needed for proper folding of the mature protein, such signal sequences can be removed and replaced with the ompA signal sequence. Unique BamHI restriction sites can be introduced at the amino-termini of the proprotein coding sequences directly after the signal peptide coding sequences of VIP3 and at the carboxy-termini of VIP3 coding sequence. These BamHI fragments can then be cloned into the pIN-III-ompA vectors as described above.

General methods for employing the strains of the invention in pesticide control or in engineering other organisms as pesticidal agents are known in the art. See, for example U.S. Pat. No. 5,039,523 and EP 0480762A2.

VIP3 can be fermented in a bacterial host and the resulting bacteria processed and used as a microbial spray in the same manner that *Bacillus thuringiensis* strains have been used as insecticidal sprays. In the case of a VIP3 which is secreted from Bacillus, the secretion signal is removed or mutated using procedures known in the art. Such mutations and/or deletions prevent secretion of the VIP3 protein(s) into the growth medium during the fermentation process. The VIP3 proteins are retained within the cell and the cells are then processed to yield the encapsulated VIP3 protein. Any suitable microorganism can be used for this purpose. Psuedomonas has been used to express *Bacillus thuringiensis* endotoxins as encapsulated proteins and the resulting cells processed and sprayed as an insecticide. (H. Gaertner et al. 1993, In Advanced Engineered Pesticides, L. Kim ed.)

Various strains of *Bacillus thuringiensis* are used in this manner. Such Bt strains produce endotoxin protein(s) as well as VIP3. Alternatively, such strains can produce only VIP3. A sporulation deficient strain of *Bacillus subtilis* has been shown to produce high levels of the Cry3A endotoxin from *Bacillus thuringiensis* (Agaisse, H. and Lereclus, D., "Expression in *Bacillus subtilis* of the *Bacillus thuringiensis* CryIIIA toxin gene is not dependent on a sporulation-specific sigma factor and is increased in a spoOA mutant", J. Bacteriol., 176:4734–4741 (1994)). A similar spoOA mutant can be prepared in *Bacillus thuringiensis* and used to produce encapsulated VIP3 which are not secreted into the medium but are retained within the cell.

Target crops to be protected within the scope of the present invention comprise, e.g., the following species of plants:

cereals (wheat, barley, rye, oats, rice, sorghum and related crops), beet (sugar beet and fodder beet), forage grasses (orchardgrass, fescue, and the like), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fiber plants (cotton, flax, hemp, jute), citrus fruit (oranges, lemons, grapefruit, mandarins), vegetables (spinach, lettuce, asparagus, cabbages and other Brassicae, onions, tomatoes, potatoes, paprika), lauraceae (avocados, carrots, cinnamon, camphor), deciduous trees and conifers (e.g. linden-trees, yew-trees, oak-trees, alders, poplars, birch-trees, firs, larches, pines), or plants such as maize, tobacco, nuts, coffee, sugar cane, tea, vines, hops, bananas and natural rubber plants, as well as ornamentals (including composites).

The microorganisms which have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

Entomocidal Compositions Comprising a Recombinant *Bacillus thuringiensis* Strain The present invention further provides an entomocidal composition comprising a recombinant *Bacillus thuringiensis* strain containing at least one of the novel toxin genes in recombinant form, or derivatives or mutants thereof, together with an agricultural adjuvant such as a carrier, diluent, surfactant or application-promoting adjuvant. The composition may also contain a further biologically active compound selected from fertilizers, micronutrient donors, plant growth preparations, herbicides, insecticides, fungicides, bactericides, nematicides and molluscicides and mixtures thereof. The composition may comprise from 0.1 to 99% by weight of a recombinant *Bacillus thuringiensis* strain containing at least one of the novel genes in recombinant form, or the derivatives or mutants thereof, from 1 to 99.9% by weight of a solid or liquid adjuvant, and from 0 to 25% by weight of a surfactant. The recombinant *Bacillus thuringiensis* strain containing at least one of the novel genes in recombinant form, or the composition containing it, may be administered to the plants or crops to be protected together with certain other insecticides or chemicals (1993 Crop Protection Chemicals Reference, Chemical and Pharmaceutical Press, Canada) without loss of potency. It is compatible with most other commonly used agricultural spray materials but should not be used in extremely alkaline spray solutions. It may be administered as a dust, a suspension, a wettable powder or in any other material form suitable for agricultural application.

A recombinant *Bacillus thuringiensis* strain containing at least one of the novel genes in recombinant form is normally applied in the form of entomocidal compositions and can be applied to the crop area or plant to be treated, simultaneously or in succession, with further biologically active compounds. These compounds may be both fertilizers or micronutrient donors or other preparations that influence plant growth. They may also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. The formulations, i.e. the entomocidal compositions, preparations or mixtures containing the recombinant *Bacillus thuringiensis* strain containing the novel gene in recombinant form as an active ingredient or combinations thereof with other active ingredients, and, where appropriate, a solid or liquid adjuvant, are prepared in known manner, e.g., by homogeneously mixing and/or grinding the active ingredients with extenders, e.g., solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils such as epoxidised coconut oil or soybean oil; or water.

The solid carriers used, e.g., for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredients to be formulated, suitable surface-active compounds are nonionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds. Suitable soaps are the alkali metal salts, alkaline earth metal salts or unsubstituted or substituted ammonium salts of higher fatty acids (C sub 10-C sub 22), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates. The fatty sulfonates or sulfates are usually in the forms of alkali metal salts, alkaline earth metal salts or unsubstituted or substituted ammonium salts and generally contain a C sub 8-C sub 22 alkyl radical which also includes the alkyl moiety of acyl radicals, e.g. the sodium or calcium salt of ligno-sulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide. Non-ionic surfactant are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one C sub 8-C sub 22 alkyl radical and, as further substituents, lower unsubstituted or halogenated alkyl, benzyl or hydroxyl-lower alkyl radicals. The salts are preferably in the form of halides, methylsulfates or ethylsulfates, e.g., stearyltrimethylammonium chloride or benzyldi-(2-chloroethyl) ethylammonium bromide.

The surfactants customarily employed in the art of formulation are described, e.g., in "McCutcheon's Detergents and Emulsifiers Annual", MC Publishing Corp. Ridgewood, N.J., 1979; Dr. Helmut Stache, "Tensid Taschenbuch" (Handbook of Surfactants), Carl Hanser Verlag, Munich/Vienna.

Another particularly preferred characteristic of an entomocidal composition of the present invention is the persistence of the active ingredient when applied to plants and soil. Possible causes for loss of activity include inactivation by ultra-violet light, heat, leaf exudates and pH. For example, at high pH, particularly in the presence of reductant, δ-endotoxin crystals are solubilized and thus become more accessible to proteolytic inactivation. High leaf pH might also be important, particularly where the leaf surface can be in the range of pH 8–10.Formulation of an entomocidal composition of the present invention can address these problems by either including additives to help prevent loss of the active ingredient or encapsulating the material in such a way that the active ingredient is protected from inactivation. Encapsulation can be accomplished chemically (McGuire and Shasha, 1992) or biologically (Barnes and Cummings, 1986). Chemical encapsulation involves a process in which the active ingredient is coated with a polymer while biological encapsulation involves the expression of the δ-endotoxin genes in a microbe. For biological encapsulation, the intact microbe containing the δ-endotoxin protein is used as the active ingredient in the formulation. The addition of UV protectants might effectively reduce irradiation damage. Inactivation due to heat could also be controlled by including an appropriate additive.

The entomocidal compositions usually contain 0.1 to 99%, preferably 0.1 to 95%, of a recombinant *Bacillus thuringiensis* strain containing at least one of the novel genes in recombinant form, or combination thereof with other active ingredients, 1 to 99.9% of a solid or liquid adjuvant, and 0 to 25%, preferably 0.1 to 20%, of a surfactant. Whereas commercial products are preferably formulated as concentrates, the end user will normally employ dilute formulations of substantially lower concentration. The entomocidal compositions may also contain further ingredients, such as stabilizers, antifoams, viscosity regulators, binders, tackifiers as well as fertilizers or other active ingredients in order to obtain special effects.

Methods of Controlling Insects

In view of the above description of the invention, it is apparent that there are several methods by which insects may be controlled using proteins of the VIP3 class as an insecticidal principle, either alone or in combination with supplementary insect control principles such as δ-endotoxins. Any method of delivering a VIP3 protein for ingestion by a susceptible insect will result in the control of that insect.

In one embodiment of the invention, plants are transformed with a gene encoding a protein of the VIP3 class. Expression of the protein may occur at any time during growth and development of the plant, depending on the nature of the insect to be controlled. For example, a protein of the VIP3 class can, according to the invention, be expressed in roots, stems, leaves, seeds, pollen, etc. This provides the advantage of expressing the protein only in those cells or tissues upon which the target insect feeds. Feeding the cells or tissues of a plant expressing VIP3 protein to a susceptible insect will result in the control of that insect. In one embodiment of the invention, a VIP3 protein is expressed in the stem or stalk of a plant in order to control black cutworm. The plants may be grown under either field or greenhouse conditions. Seed containing a VIP3 protein can also be protected against insect damage when in storage.

EXAMPLES

The following examples further describe the materials and methods used in carrying out the invention and the subsequent results. They are offered by way of illustration, and their recitation should not be considered as a limitation of the claimed invention.

Example 1

Isolation and Biological Characterization of *Bacillus thuringiensis* Strain AB88

A Bt strain, designated AB88, was isolated from grain bin dust samples by standard methodologies. A subculture of AB88 was grown for 24–48 hrs. and cell-free culture supernatant was tested for insecticidal activity as follows. For European corn borer (*Ostirina nubilalis*), black cutworm (*Agrotis ipsilon*), fall armyworm (*Spodoptera frugiperda*), corn earworm (*Helicoverpa zea*) and tobacco budworm (*Heliothis virsecens*) 100 $\mu$l of culture supernatant was pipetted onto the surface of 18 $cm^2$ of solidified artificial diet (Bioserv #F9240) and allowed to air dry. Neonates were then placed onto the surface of the diet and held at 30° C. Mortality was scored after 36–72 hrs.

For Colorado potato beetle (*Leptinotarsa decemlineata*) five $cm^2$ potato leaf pieces were dipped into culture supernatant, air dried, and placed on moistened filter paper in 50×9 mm petri dishes. Neonates were then placed on the leaf pieces and held at 30° C. Mortality was scored after 36–72 hrs.

For western corn rootworm (*Diabrotica virigifera*) culture supernatant was mixed with molten artificial diet (Marrone et al. (1985) J. of Economic Entomology 78:290–293) and allowed to soldify. Soldified diet was cut into pieces and placed in plastic dishes. Neonates were then placed on the diet pieces and held at 30° C. Mortality was scored after 6 days.

For all bioassays half of the culture supernatant sample was autoclaved 15 minutes to test for the presence of β-exotoxin. The results are as follows:

TABLE 11

| Insect species tested | Order | Percent mortality of culture supernatant | |
|---|---|---|---|
| | | Non-autoclaved | Autoclaved |
| Agrotis ipsilon | Lepidoptera | 100 | 5 |
| Ostrinia nubilalis | Lepidoptera | 100 | 0 |
| Spodoptera frugiperda | Lepidoptera | 100 | 4 |
| Helicoverpa zea | Lepidoptera | 100 | 12 |
| Heliothis virescens | Lepidoptera | 100 | 12 |
| Leptinotarsa decemlineata | Coleoptera | 0 | 0 |
| Diabrotica virgifera virgifrra | Coleoptera | 0 | 5 |

The reduction of insecticidal activity of the culture supernatant to insignificant levels by autoclaving indicates that the active principle is not β-exotoxin.

Delta-endotoxin crystals were purified from strain AB88 by standard methodologies. No activity from pure crystals was observed when bioassayed against *Agrotis ipsilon*.

Example 2

Purification of the VIP3A(a) Protein from Strain AB88

Bacterial liquid culture was grown overnight at 30° C. in TB media and the supernatant retained. Proteins were precipitated with ammonium sulfate (70% saturation), centrifuged and the pellet retained. The pellet was resuspended in the original volume of 20 mM Tris pH 7.5 and dialyzed against the same buffer. AB88 proteins have been separated by several different methods following clarification including isoelectric focusing (Rotofor, BioRad, Hercules, Calif.), precipitation at pH 4.5, ion-exchange chromotography, size exclusion chromatography and ultrafiltration.

European corn borer (ECB)-active protein remained in the pellet obtained by pH 4.5 precipitation of dialysate. When preparative IEF was done on the dialysate using pH 3–10 ampholytes, ECB insecticidal activity was found in all fractions with pH of 7 or greater. SDS-PAGE analysis of these fractions showed protein bands of MW ~60 kDa and ~80 kDa. The 60 kDa and 80 kDa bands were separated by anion exchange HPLC on a Poros-Q column (PerSeptive Biosystems, Cambridge, Mass.). N-terminal sequence was obtained from two fractions containing proteins of slightly differing MW, but both of approximately 60 kDa in size. The sequences obtained were similar to each other and to some δ-endotoxins.

anion exchange fraction 23 (smaller): xEPFVSAxxxQxxx (SEQ ID NO:10)

anion exchange fraction 28 (larger): xEYENVEPFVSAx (SEQ ID NO:11)

When the ECB-active pH 4.5 pellet was further separated by anion exchange on a Poros-Q column, activity was found only in fractions containing a major band of ~60 kDa.

Black cutworm-active protein also remained in the pellet when AB88 dialysate was brought down to pH 4.5. In preparative IEF using pH 3–10 ampholytes, activity was not found in the ECB-active IEF fractions; instead, it was highest in a fraction of pH 4.5–5.0. Its major components have molecular weights of ~35 and ~80 kDa.

The pH 4.5 pellet was separated by anion exchange HPLC to yield fractions containing only the 35 kDa material and fractions containing both 35 kDa and 80 kDa bands.

Example 3

Characterization of VIP3A(a) from AB88

Fractions containing the various lepidopteran active vegetative proteins were generated as described in Example 2. Biological analysis of fractions demonstrated that different VIPs s were responsible for the different lepidopteran species activity.

The *Agrotis ipsilon* activity is due to an 80 kDa and/or a 35 kDa protein, either delivered singly or in combination. These proteins are not related to any δ-endotoxins from Bt as evidenced by the lack of sequence homology of known Bt δ-endotoxin sequences. Also, these proteins are not found in the AB88 δ-endotoxin crystal. N-terminal sequences of the major δ-endotoxin proteins were compared with the N-terminal sequences of the 80 kDa and 35 kDa VIP and revealed no sequence homology. A summary of the results follows:

TABLE 12

| Agrotis VIP N-terminal sequences | N-terminal sequence of major δ-endotoxin proteins |
|---|---|
| | 130 kDa |
| | MDNNPNINE (SEQ ID NO:14) |
| 80 kDa | 80 kDa |
| MNKNNTKLPTRALP (SEQ ID NO:12) | MDNNPNINE (SEQ ID NO:15) |
| | 60 kDa |
| | MNVLNSGRTTI (SEQ ID NO:16) |
| 35 kDa | |
| ALSENTGKDGGYIVP (SEQ ID NO:13) | |

The *Ostrinia nubilalis* activity is due to a 60 kDa VIP and the *Spodoptera frugiperda* activity is due to a VIP of unknown size.

*Bacillus thuringiensis* strain AB88 has been deposited in the Agricultural Research Service, Patent Culture Collection (NRRL), Northern Regional Research Center, 1815 North University Street, Peoria, Ill. 61604, U.S.A. and given the Accession No. NRRL B-21225.

Example 4

Isolation and Biological Activity of *Bacillus thuringiensis* AB424

A *B. thuringiensis* strain, designated AB424, was isolated from a moss covered pine cone sample by standard methods known in the art. A subculture of AB424 was grown and prepared for bioassay.

Biological activity was evaluated as described in Example 1. The results are as follows:

TABLE 13

| Insect species tested | Percent mortality |
| --- | --- |
| Ostrinia nubilalis | 100 |
| Agrotis ipsilon | 100 |
| Diabrotica virgifera virgifera | 0 |

Strain AB424 has been deposited in the Agricultural Research Service, Patent Culture Collection (NRRL), Northern Regional Research Center, 1815 North University Street, Peoria, Ill. 61604, U.S.A., and given Accession No. NRRL B-21439.

Example 5

Cloning of the vip3A(a) and vip3A(b) Genes Which Encode Proteins Active Against Black Cutworm DNA from isolates AB88 and AB424 was digested with the restriction enzymes XbaI and EcoRI respectively, ligated into pBluescript vector previously linearized with the same enzymes and dephosphorylated, and transformed into E. coli DH5α strain. Recombinant clones were blotted onto nitrocellulose filters which were subsequently probed with a 33-base long oligonucleotide corresponding to the 11-N terminal amino acids of the 80 kDa protein active against Agrotis ipsilon (black cutworm). Four out of 400 recombinant clones were positive. Insect bioassays of the positive recombinants exhibited toxicity to black cutworm larvae comparable to that of AB88 or AB424 supernantants.

The nucleotide sequence of pCIB7104, a positive recombinant clone from AB88, and of pCIB7107, a positive recombinant clone from AB424, was determined by the dideoxy termination method of Sanger et al., Proc. Natl. Acad. Sci. U.S.A., 74: 5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

The clone pCIB7104 contains the vip3A(a) gene whose coding region is disclosed in SEQ ID NO:1 and the encoded protein sequence is disclosed in SEQ ID NO:2. A synthetic version of the coding region designed to be highly expressed in maize is given in SEQ ID NO:7. Any number of synthetic genes can be designed based on the amino acid sequence given in SEQ ID NO:2.

The clone pCIB7107 contains the VIP3A(b) gene whose coding region is disclosed in SEQ ID NO:3 and the encoded protein is disclosed in SEQ ID NO:4. Both pCIB7104 and pCIB7107 have been deposited with the Agricultural Research Service Patent Culture Collection (NRRL) and given Accession Nos. NRRL B-21422 and B-21423, respectively.

Example 6

Identification of Novel vip3-like Genes by Hybridization

To identify Bacillus containing genes related to the vip3A (a) gene from isolate AB88, a collection of Bacillus isolates was screened by hybridization. Cultures of 463 Bacillus strains were grown in microtiter wells until sporulation. A 96-pin colony stampel was used to transfer the cultures to 150 mm plates containing L-agar. Inoculated plates were kept at 30° C. for 10 hours, then at 4° C. overnight. Colonies were blotted onto nylon filters and probed with a 1.2 Kb HindIII VIP3A(a) derived fragment. Hybridization was performed overnight at 62° C. using hybridization conditions of Maniatis et al. Molecular Cloning: A Laboratory Manual (1982). Filters were washed with 2×SSC/0.1% SDS at 62° C. and exposed to X-ray film.

Of the 463 Bacillus strains screened, 60 contain vip3-like genes that could be detected by hybridization.

Example 7

Presence of vip3-like genes and VIP3-like proteins in Bacillus isolates

Bacillus isolates other than AB88 have demonstrated insecticidal activity against Lepidopteran larvae when spent culture supernatants were tested. Some isolates which were active against black cutworm were analyzed for the presence of vip3-like genes and for the production of VIP3-like proteins.

Figure 3:
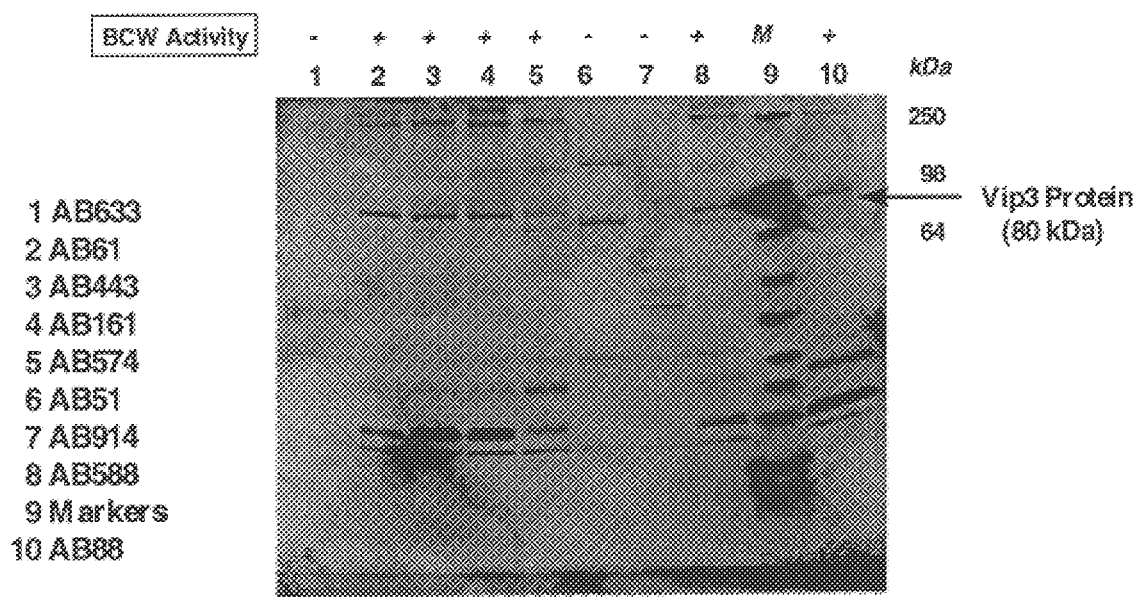
FIG. 3: Presence of VIP3 proteins in Bacillus isolates as identified by Western assay.
Figure 4:
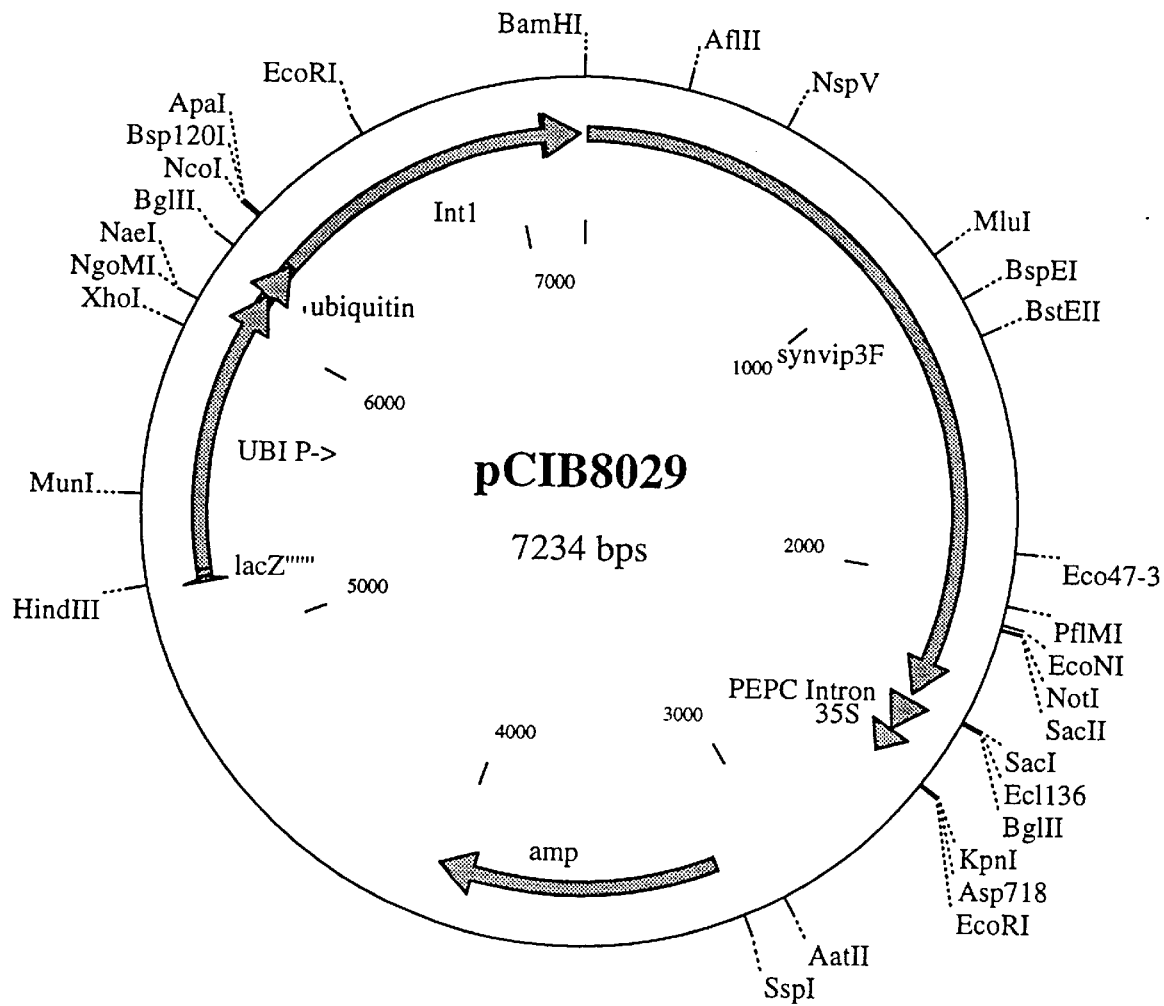
FIG. 4: Plasmid pCIB8029 containing a maize ubiquitin promoter in an expression cassette.
Figure 5:
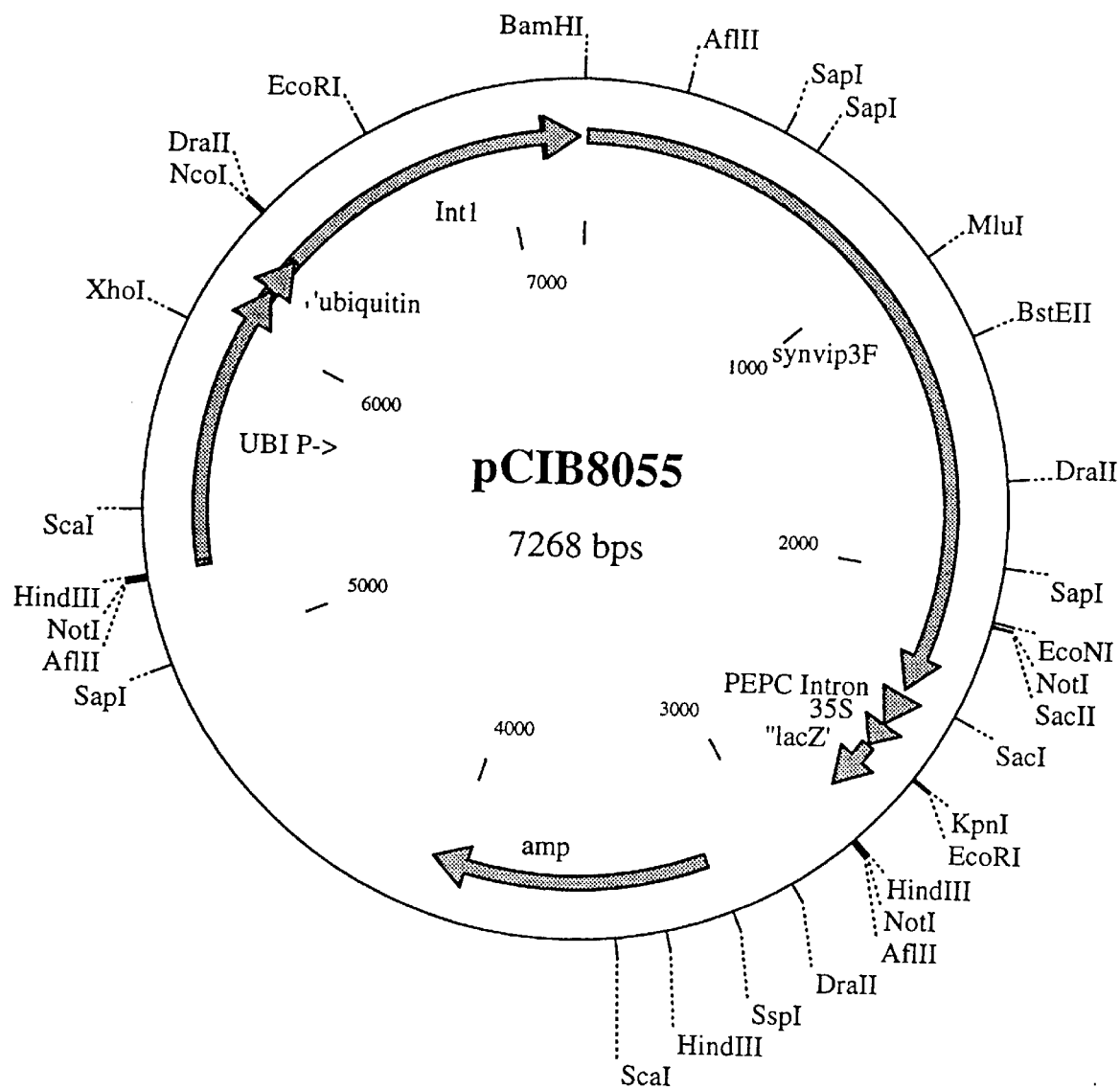
FIG. 5: Plasmid pCIB8055 containing a maize ubiquitin promoter in an expression cassette.
Figure 6:
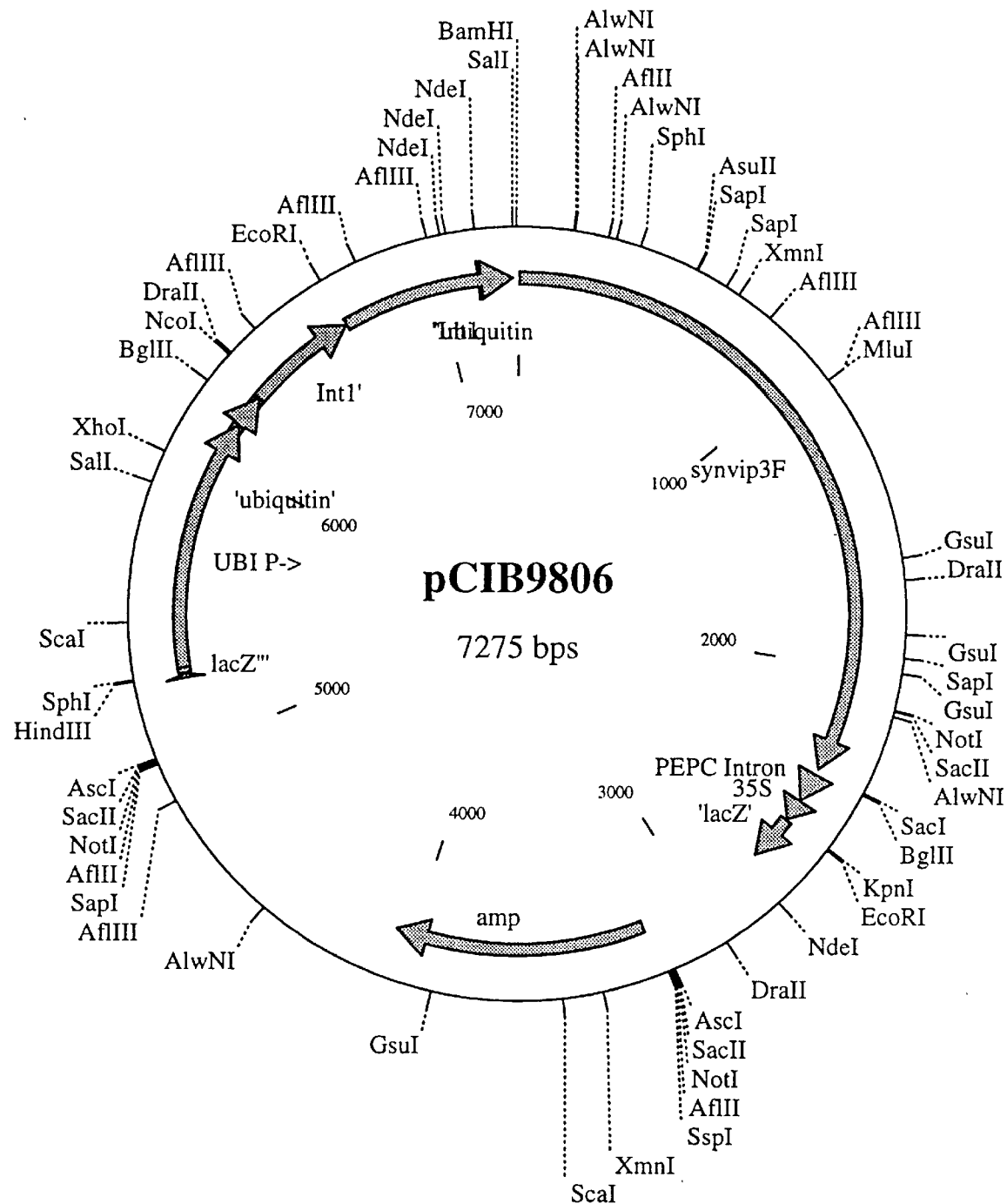
FIG. 6: Plasmid pCIB9806 containing a maize ubiquitin promoter in an expression cassette.
Figure 7:
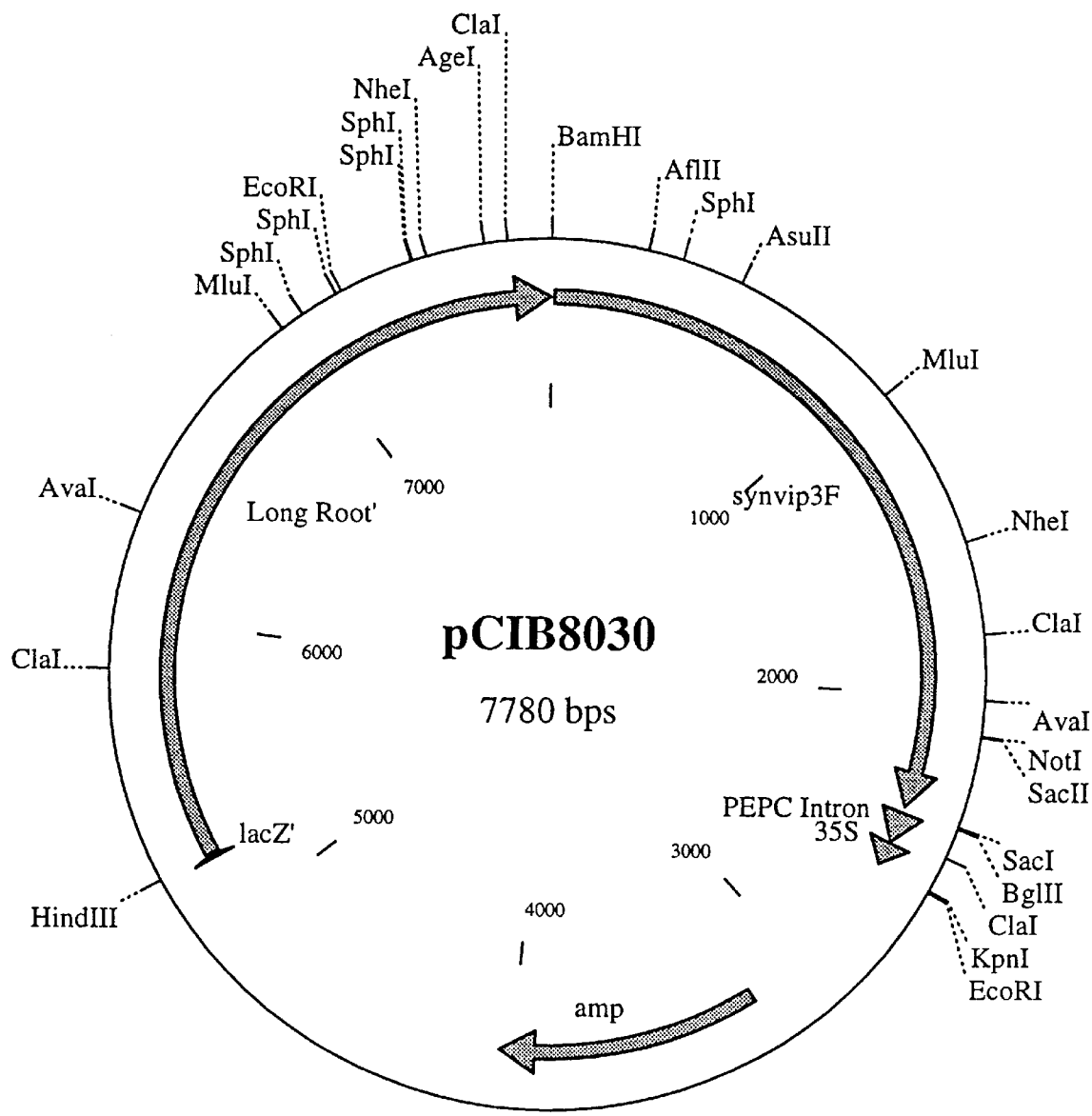
FIG. 7: Plasmid pCIB8030 containing a promoter from a maize methalothionein-like gene in an expression cassette.
Figure 8:
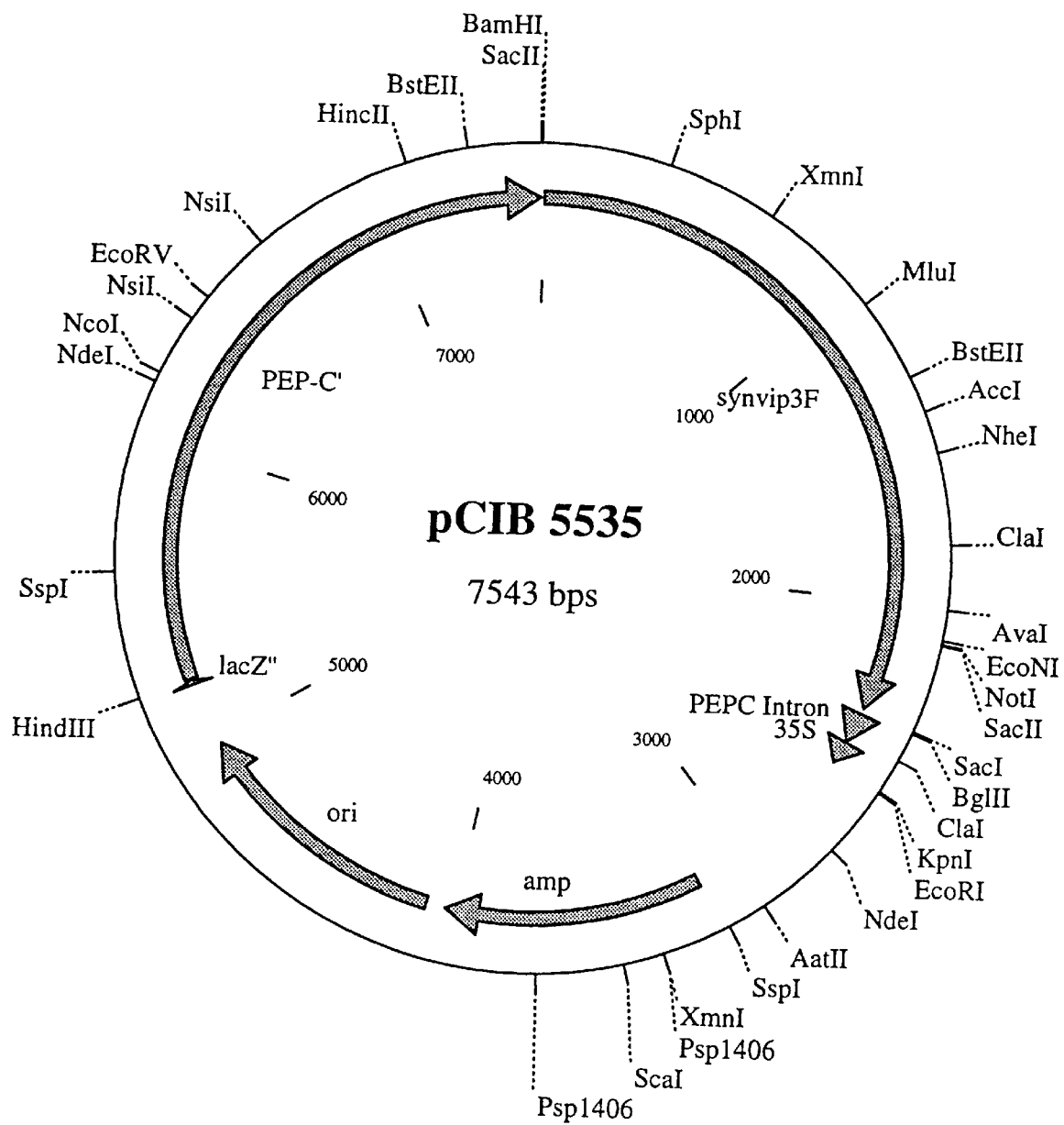
FIG. 8: Plasmid pCTB5535 containing a promoter from a maize PEPC gene in an expression cassette.
Figure 9:
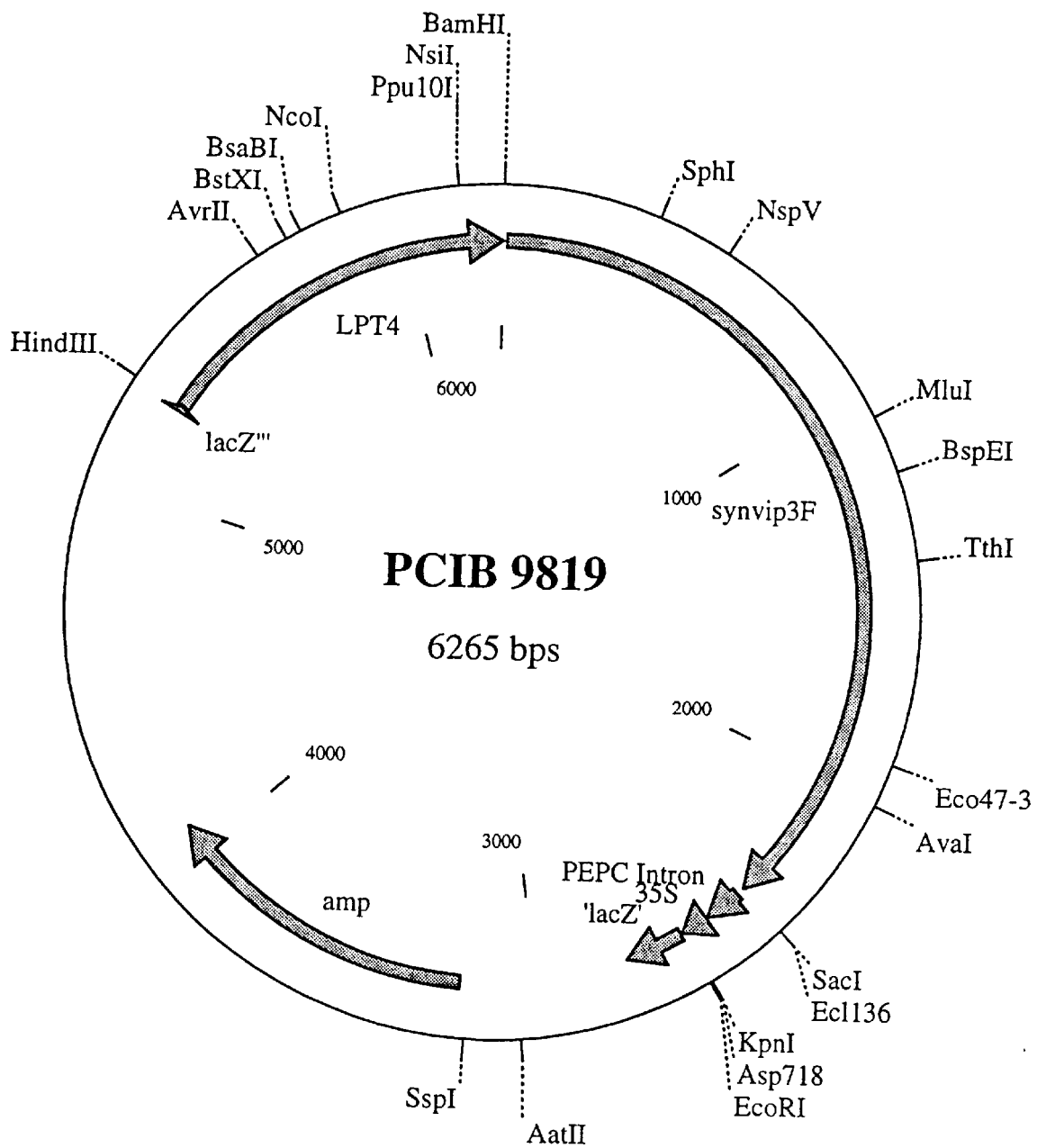
FIG. 9: Plasmid pCIB9819 containing a promoter from a barley non-specific lipid transfer protein LTP4 gene in an expression cassette.

A standard PCR analysis was used to determine whether the black cutworm-active Bacillus isolates contained a vip3-like gene. Using the PCR primer pair GW110 (5'-CGA TTA ATG TTG GCC TC-3'; SEQ ID NO:17) and GW 111 (5'-CAT TAG CAT CTC CGG ACA CAG-3'; SEQ ID NO:18) it was determined that all of the black cutworm active isolates produced a 728 bp vip3 gene product which was equal to the size produced by the type strain, AB88 (FIG. 3). One Bacillus isolate, AB51, which was not active against black cutworm, produced the same size vip3 product. None of the other non-black cutworm active Bacillus isolates produced a vip3 PCR product.

Analysis of VIP3 protein production was done using a standard western blot procedure. Antibodies raised against the VIP3A(a) protein described in the above example were used to detect immunoreactive proteins. Aliquots of cell free culture supernatants from sporulated cultures were run on SDS-PAGE gels using standard methods. Standard western blotting procedures were then carried out to determine the presence of VIP3-like proteins. All of the Bacillus isolates which had a 728 bp PCR product and were active against black cutworm produced an 80 kDa protein which was immunoreactive to the VIP3A(a) antibody (FIG. 3). The AB51 isolate which had the correct size vip3 PCR product but was not active against black cutworm produced an imnmunoreactive protein which was truncated suggesting this may be the reason no biological activity against black cutworm was observed.

Example 8

Characterization of Bacillus thuringiensis Strain AB51 Containing a vip3-like Gene A B. thuringiensis strain, designated AB51, was shown to contain proteins of the VIP3 class by western analysis using rabbit polyclonal anti-Vip3A(a) antibodies. The vip3-like gene was cloned into pKS which created pCIB7112. This gene was given the designation vip3A(c). The DNA sequence for vip3A(c) is disclosed in SEQ ID NO:5 and the encoded protein sequence is disclosed in SEQ ID NO:6. The VIP3A(c) protein is 746 amino acids long, 43 amino acids shorter than its VIP3A(a) and VIP3A(b) homologues.

Example 9

Characterization of Bacillus thuringiensis Strain Containing a Cryptic vip3-like Gene A B. thuringiensis strain, designated M2194, was shown to contain vip3-like gene(s) by colony hybridization as described in Example 6. The M2194 vip3-like gene is considered cryptic since no expression can be detected throughout the bacterial growth phases either by immunoblot analysis using polyclonal antibodies raised against the VIP3A(a) protein isolated from AB88 or by bioassay as described in Example 1.

The M2194 vip3-like gene was cloned into pKS, which created pCIB7108. *E. coli* containing pCIB7108 which comprises the M2194 vip3 gene was active against black cutworm demonstrating that the gene encodes a functional protein with insecticidal activity. The plasmid pCIB7108 has been deposited with the Agricultural Research Service Patent Culture Collection (NRRL) and given Accession No. NRRL B-21438.

Example 10

Development of Antibodies to VIP3A(a) Protein

Antiserum against purified Vip3A(a) insecticidal protein was produced in rabbits and goats. For rabbits, nitrocellulose-bound protein (50 $\mu$g) was dissolved in DMSO, emulsified with Freund's complete adjuvant (Difco) and injected subcutaneously twice a month for three months. For goats, active soluble pure Vip3A protein (300 $\mu$g) was injected intramuscularly twice a month for three month. They were bled 10 days after the second and third injection and the serum was recovered from the blood sample (Harlow, E. and Lane, D. *Antibodies: A Manual Laboratory,* Cold Spring Harbor Lab. Press, N.Y., 1988). The antiserums were then fractionated by affinity chromatography utilizing staphylococcal protein A, and the resulting IgG fraction was further purified by filtering through a column containing immobilized-*E. coli* lysate (Yu, C. G. et al. Appl. Environ. Microbiol. 63:532–536 (1997)).

The rabbit and goat antiserums were characterized analyzing the Vip3A(a) protein by western blot. Proteins were separated by SDS/PAGE and transferred to nitrocellulose. Nitrocellulose blots were blocked in 20 mM Tris-HCl, pH 7.5/0.15M NaCl/0.02% $NaN_3$/5% nonfat dry milk. Blots were developed by using either rabbit raised or goat-raised anti-Vip3A(a) antibodies at a concentration of 200 ng/ml or 100 ng/ml respectively. Alkaline phosphatase-conjugated goat antirabbit IgG or rabbit antigoat antiserum were used as secondary antibodies at a concentration of 1 $\mu$g/ml (Kirkegaard & Perry Laboratories, Inc.). Bromochloroindolyl-phosphate and nitroblue tetrazolium were used as substrate for the alkaline phosphatase reaction. Both anti-Vip3A(a) antibodies, the rabbit and the goat raised, are polyclonal. The anti-Vip3A(a) antibodies obtained from goat have a higher titer than the ones obtained from rabbits. In the experimental approach, anti-Vip3A(a) antibodies from rabbit should be used at a dilution 1/500 from the original serum (200 ng/ml). By comparison, the anti-Vip3A(a) antibodies obtained from goat can be diluted up to 1/2000 (100 ng/ml) from the original serum. While the rabbit raised antibodies only recognize the N-terminal portion of the Vip3A(a) protein, the antibodies obtained from goats react with epitopes present throughout the full length of the Vip3A(a) protein.

Example 11

Construction of Plant Expression Cassettes

Plant expression cassettes consist of promoters that can drive the expression of a coding sequence either constitutively or in a tissue-specific manner, the coding sequences to be expressed and the termination sequences which allow the polyadenylation of the mRNA and its proper translation.

The promoters selected in the DNA constructs of the present invention includes constitutive promoters such as the one from the maize ubiquitin gene (Christensen et al. Plant Mol. Biol. 12:619–632,1989) (pCIB8029, FIG. 4; pCIB8055, FIG. 5; pCIB9806, FIG. 6), and tissue specific promoters such as those from the maize methalothionein-like gene (de Framond, A. FEBS 290:103–106,1991) (pCIB8030, FIG. 7; pCIB8056, pCIB9805) which provides a root-preferred expression, from the maize PEPC gene (Hudspeth, R. L. and Grula, J. W. Plant Mol. Biol. 12:579–589, 1989) (pCIB5535, FIG. 8; pCIB9807) which provides a green-tissue specific expression, and from the barley non-specific lipid transfer protein LTP4 (pCIB9819, FIG. 9)(Molina, A. and Garcia-Olmedo, F. Plant J. 4:983–991, 1993) which provides a stem-preferred expression. All constructs used in the present invention contain the terminator sequence derived from the 35S CaMV and the intron 9 derived from the maize PEPC gene for enhancing gene expression purposes. The plasmids pCIB8029, pCIB8055, and pCIB9806 contain the intron#1of the maize ubiquitin gene placed between the maize ubiquitin promoter and the vip3A(a) gene. The construct comprising the encoding sequence of the vip3A(a) gene, the intron#9 and the 35S terminator sequence was engineered into the recipient plasmid bearing the different promoters as double digests BamHI-EcoRI.

The plant expression cassettes were used as such in the plant transformation experiments, or they were linearised by using restriction enzymes that cut in the $Amp^R$ gene of the backbone plasmid. In some experiments, fragments comprising the promoter, gene of interest, intron and terminator were isolated from the rest of the plasmid backbone by restriction digestion and fragment purification. In these cases fragment purification proceeded as follows: 500 $\mu$g of DNA is digested with the appropriate enzyme and separated on a 0.8% agarose gel. The fragment of interest is identified, cut out from the gel and purified using a Durapore Millipore filter (0.45 micron). The filtrate containing the fragment is precipitated with sodium acetate and ethanol. The fragment is resuspended in TE and used in transformation experiments.

Example 12

Insecticidal activity of maize plants expressing VIP3A(a)

Maize plants expressing VIP3A(a) protein were tested for insecticidal effects on the insect species listed in the table below by the following procedure. One to four 4 cm sections were cut from leaves of transgenic and control maize plants. Each leaf piece was placed on a moistened filter disc in a 50×9 mm petri dish. Five neonates of the species being tested were placed on each leaf piece giving a total of 5–20 larvae tested for each plant. The Petri dishes were incubated at 30° C. in the dark. Mortality was scored after 48–72 hours. Results are shown in Table 16.

TABLE 14

| Insect species tested | Percent mortality | |
|---|---|---|
| | VIP3A(a) | Control |
| Maize Pests | | |
| Black cutworm (Agrotis ipsilon) | 100 | 0 |
| Fall armyworm (Spodoptera frugiperda) | 100 | 0 |
| Sugarcane borer (Diatrea saccharalis) | 100 | 0 |
| Southwestern corn borer (Diatraea grandiosella) | 100 | 0 |
| Corn earworm (Helicoverpa zea) | 100 | 10 |
| Mediterranean corn borer (Sesamia nonagroides) | 100 | 15 |
| Other Lepidopteran Pests | | |
| Beet armyworm (S. exigua) | 100 | 0 |
| Yellow striped armyworm (S. ornithogalli) | 100 | 0 |
| Cabbage looper (Trichoplusia ni) | 100 | 20 |

Example 13

Expression of vip3A(a) in Maize Plants

Transformation of maize elite Ciba inbred lines CG00526 and 2154 with the Vip3 gene was achieved using particle bombardment of Type I callus tissue. For transformation using Type I embryogenic callus, the callus was obtained from zygotic embryos using standard culture techniques and subcultured 1–2 days prior to bombardment. Callus tissue was prepared for bombardment by placing ~20, 3–5 mm diameter pieces arranged in a ring shape onto culture medium containing 12% sucrose. Callus tissue was placed onto this media for four hours prior to bombardment. DNA used for transformation of maize callus was either circular plasmid DNA, linear plasmid DNA, or purified DNA fragments containing the Vip3 gene under control of various plant promoters. In experiments where a selectable agent was used, the gene allowed resistance to phosphinothricin or allowed for growth in the presence of mannose. Plasmids or DNA fragments isolated by filtration were precipitated onto 0.3 μm gold particles according to published procedures from BioRad Laboratories, Hercules, Calif. Gold particles were delivered using a burst pressure of 650 psi of helium. Each target plate was shot twice with the DNA coated particles. Sixteen to twenty hours after bombardment the CG00526 callus was transferred to standard culture maintenance media. Seven days post-bombardment the tissue was transferred to media containing the selection agent, Basta at a concentration of 100 mg/L. Basta is a commercial formulation of glufosinate ammonium produced by Hoechst. Callus of 2154 was kept on 12% sucrose for 1–7 days after bombardment and transferred to standard culture media containing 20–30 mg/L Basta at day 7. The 2154 and CG00526 callus was subcultured in the presence of 30 or 100 mg/L Basta, respectively, for eight weeks. Tissue surviving selection was subcultured onto lower levels of Basta (5–40 mg/L) for a period of approximately five to ten weeks to allow for tissue bulk-up and then transferred to a standard regeneration media with no selection for the production of plants. Commonly, 12% of the callus pieces bombarded produced transformed callus that survived Basta selection. Individual transformed calli would typically be regenerated to produce 20–30 plants.

Events were generated from experiments where no selection was used. In these experiments the callus was grown for a period of 9–10 weeks on maintenance media prior to transferring to regeneration media. Event 1337 is an example of a transformed VIP3 event derived from a transformation experiment with no selectable or scorable marker by screening plants for insecticidal activity.

Transformed calli were also generated from experiments where mannose selection was used. In these transformations the phosphomannose isomerase gene under control of the maize ubiquitin promoter of pCIB9818 was bombarded with the Vip3 gene. Mannose at 0.5–1.5% was included in the maintenance media for a period of twelve weeks and not included in the regeneration media.

Transgenic plants were evaluated for VIP3A(a) protein expression by insect bioassay and ELISA assay. Leaf pieces were removed from 2–4 leaf stage plants for evaluation using both black cutworm and fall army worm bioassays. Bioassays were done using ten newly hatched larvae placed in dishes with leaf pieces. Percent mortality was calculated at 72 hours. Tissues from transgenic plants were also assayed by ELISA using standard protocols to quantitate Vip3 protein levels in different plant tissues. Plant tissue was extracted and Table 17 provides representative events generated and their corresponding of insect bioassay results.

Transgenic maize plants were transformed with various plasmids containing the Vip3 gene under control of various promoters such as the maize PEP-carboxylase promoter (PEPC), the maize ubiquitin promoter (Ubi), and the maize metallothionein-like promoter (MTL). The selectable marker gene was the PAT gene under control of the maize ubiquitin promoter in pUBIAC. Representative events listed in Table 17 show the events produced with different plasmids or DNA fragments derived from plasmids. DNA fragments were generated using restriction enyzme digestions and size fractionated using electrophoresis in 0.8% agarose gels. The DNA fragments were excised from the gels, frozen, crushed and purified by filtration through 0.45 micron DuraPore Millipore filters followed by ethanol precipitation. Transformed maize events were generated with circular plasmid DNA of pCIB5535 containing the Vip3 gene under control of the maize PEPC promoter. Events were also transformed with linear plasmid DNA of pCIB5535 and pCIB8029 containing the Vip3 gene under control of the maize ubiquitin promoter. Additional events were produced by bombarding purified DNA restriction enzyme fragments containing just the Vip3 gene with promoter. Fragments corresponding to the Vip3 gene include: a 4906 bp EcoRI/HindIII fragment from pCIB5535 with the maize PEPC promoter; a 5142 bp KpnI/HindIII fragment from pCIB8030 with the MTL promoter; a 4597 bp KpnI/HindIII fragment of pCIB8029 with the maize ubiquitin promoter; a 4818 bp HindIII fragment of pCIB8055 with the maize ubiqutin promoter; a 5364 HindIII fragment of pCIB8056 with the MTL promoter; a 5964 AscI fragment of pCIB9805 with the MTL promoter; a 5418 bp AscI fragment of pCIB9806 with the maize ubiqutin promoter; and a 5727 bp AscI fragment of pCIB9807 with the maize PEPC promoter.

TABLE 15

| | | | Mortality (%) | |
|---|---|---|---|---|
| Event No. | Plasmid Used | Chimeric Gene | Fall Armyworm | Black Cutworm |
| 891 | pCIB5535 | PEPC:vip3A(a) | 100 | 100 |
| 906 | pCIB5535 and pCIB8029 | PEPC:vip3A(a) and Ubi:vip3A(a) | 100 | 100 |

TABLE 15-continued

| Event No. | Plasmid Used | Chimeric Gene | Mortality (%) Fall Armyworm | Black Cutworm |
|---|---|---|---|---|
| 946 | pCIB5535 and pCIB8030 | PEPC:vip3A(a) and MTL:vip3A(a) | 100 | 100 |

Example 14

Insecticidal activity of maize plants containing Vip3 and Bt δ-endotoxins

VIP3A(a) has little activity against European corn borer (ECB). To make plants with broad spectrum lepidopteran control, maize plants containing a vip3A(a) gene were crossed with maize plants containing a cry1B, which is active against ECB. Progeny from the crosses were bioassayed against ECB and fall armyworm (FAW) as described in Example 1. Results are shown in Table 18. Approximately 34% of the progeny were not active against either species, 15.4% were active only on ECB, 23.1% were active only on FAW and 27.9% were active against both species. Plants active against both species contained both VIP3A(a) and Cry1B protein. Similar results are obtained using other Bt δ-endotoxins, particularly Cry1Ab or Cry9C.

TABLE 16

| Cross | % ECB active | % FAW active | % ECB & FAW active | % not active |
|---|---|---|---|---|
| VIP3A(a) X Cry1B | 15.4 | 23.1 | 27.9 | 34.6 |

Example 15

VIP3A(a) Lyses the Midgut Epithelial Cells of Susceptible Insects

Feeding and gut clearance studies. The temporal sequence of symptoms following the ingestion of VIP3A(a)-containing diet by second-instar black cutworm (BCW) larvae, a susceptible insect, were recorded from the time of initial administration until larval death. Larvae exposed to control diet showed active feeding followed by uninterrupted gut parastalsis, In contrast, the addition of VIP3A(a) protein in the diet had a significant effect on feeding behavior. When added at concentrations as low as 4 ng per $cm^2$, the larvae fed on and off during periods of 10–20 min. The presence of blue color in their guts indicated feeding but the clearance of the gut content was dramatically affected as judged by the deceased number of frass. With 4 ng of VIP3A(a) per $cm^2$ added to the diet, larval development was significantly impaired after a 48 h incubation period but no mortality was observed. At concentrations of 40 ng of Vip3A(a) per $cm^2$, the larvae suffered gut paralysis upon ingestion of minute amounts of diet and no frass could be seen indicating an almost complete lack of gut clearance. Under this condition, ca. 50% mortality was recorded after 48 hr. When concentrations higher than 40 ng of VIP3A(a) per cm were used, the larvae were moribund after only a few bites, with no frass and mortality rates approaching 100%. When similar experiments were conducted with fall armyworm, also a susceptible insect, similar behavioral patterns were observed. In contrast, European corn borer did not alter its feeding behavior when VIP3A(a) protein was added to the diet even at concentrations as high as 400 ng of VIP3A(a) per $cm^2$.

Histological observations of the effects of the Vip3A(a) protein. Histopathological observations on the effects of the VIP3A(a) protein on BCW were conducted on second and third instar larvae which had been fed a diet containing VIP3A(a). Analysis of BCW gut cross-sections showed extensive damage to the midgut epithelium indicating that the midgut tissue is a primary site of action of the Vip3A(a) protein. No damage was discernible in the foregut and hindgut. Midgut epithelial cells from untreated larvae were closely associated with one another showing no evidence of damage. Sections from larvae that had been fed for 24 h with diet containing Vip3A(a) showed that distal ends of the epithelium columnar cells had become distended and bulbous. Although the goblet cells exhibited some morphological alterations, they did not show signs of damage at this stage. Degeneration of the epithelium columnar cells continued such that, after 48 h of ingesting Vip3A(a)-containing diet, the lumen was filled with debris of disrupted cells. The goblet cells also exhibited signs of damage after 48 h, but both types of cells were still attached to the basement membrane. Black cutworm larvae were dead at 72 h and desquamation of the epithelial layer was complete. While a similar histopathology was observed for fall armyworm, European corn borer did not exhibit any tissue damage under similar experimental conditions.

In vivo immunolocalization of the Vip3A(a) protein. Third instar larvae of black cutworm and European corn borer fed on artificial diet supplemented with 100–200 ng of VIP3A(a) per $cm^2$ were used for immunocytochemical characterization of the VIP3A(a) binding to midgut sections. The bound VIP3A(a) was visualized using rabbit anti-VIP3A(a) antibodies previously purified through protein A sepharose and E. coli immobilized columns (Yu, C. G. et al. Appl. Environ. Microbiol. 63:532–536, 1997). VIP3A(a) binding was detected in midgut epithelium of black cutworm, while showing no binding to European corn borer midguts. Midgut sections from black cutworm larvae fed with control diet showed no VIP3A(a) binding. The VIP3A (a) binding seems to be specifically associated to the apical microvilli and it is mostly associated to the columnar cells, with no detectable signal in the goblet cells.

Example 16

VIP3A(a) and VIP3A(b) Induce Apoptosis in Insect Cells

VIP3A(a) and VIP3A(b) were shown to be a apoptosis inducing protein arose by the characterization of its insecticidal effects towards an insect cell line (Sf-9) derived from Spodoptera frugiperda, an insect susceptible to VIP3A(a). VIP3A(a) showed insecticidal activity towards the insect cell line when kept present throughout the experiment. When SF-9 insect cells are transiently exposed to VIP3A(a) and VIP3A(b), their cell viability was significantly reduced even with exposure times as short as 5 min. Once the incubation time exceeded 10 min, the effects of the VIP3A (a) and VIP3A(b) on insect cell viability over a period of 6 hours were maximal showing a reduction of 90% in cell viability. The cytological changes occurring in SF-9 cells transiently exposed to VIP3A(a) were monitored by microscopy. Small protrusions appeared on the surface of the treated cells some time between 10 and 15 min after their exposure to the VIP3A(a) protein. At this stage, the mitochondria of the cells remained functionally intact as revealed by staining with rhodamine 123, a dye that accumulates in mitochondria with active membrane potential (Johnson, L. V. et al Proc. Natl. Acad. Sci. U.S.A. 77:990–994, 1980). These protrusions eventually disappeared and the cells entered a phase of profuse vacuolization lasting an additional 30 to 60 min. During the final stages, the insect cells are seen to swell before disintegration. For an individual cell, the entire process required 1 to 2 hours. All these cellular events are consistent with previous studies on cells undergoing apoptosis particularly considering that programmed cell death during metamorphosis of certain insects is accompanied by cellular vacuolization and swelling (Schwartz, L. M. et al Proc. Natl. Acad. Sci. U.S.A. 90:980–984 (1993)).

Recent studies have shown that the distribution of phospholipids in the plasma membrane is affected in very early stages of animal cells undergoing apoptosis (Martin, S. J., et al. J. Exp. Med.: 182, 1545–1556, 1995) particularly the externalization of the phosphatidylserine (PS). This process can be visualized by using Annexin V, an anticoagulant protein with high affinity for phosphatidylserine (PS). When VIP3A(a)-treated SF-9 cells were incubated with Annexin V, an externalization of PS was revealed in insect cell membranes as early as 5–10 min after the exposure to VIP3A(a) probably marking the onset of apoptosis.

One of the key molecular events that is the hallmark of apoptosis is endonucleolysis resulting in a double strand DNA break freeing oligonucleosome-sized fragments of 200 base pair and multiples. We examined the occurrence of endonucleolysis in SF-9 cells treated with VIP3A(a) using an in situ detection method and analysing the DNA by agarose gel electrophoresis. Based on the ability of the Klenow enzyme to incorporated modified nucleotides using the DNA ends generated by DNA fragmentation, SF-9 insect cells showed signs of endonucleolysis as early as 30 min upon their exposure to the VIP3A(a) protein. This stage will coincide with the appearance of membrane-bound subcellular apoptotic bodies visualized in the microscopical observations. These early indications of endonucleolytic activity were confirmed by the detection of DNA fragments in agarose gels characteristic of a chromatin ladder slightly latter in the process. These results corroborated the indications obtained from cytological observations, that the SF-9 cells initiate an apoptotic-type of programmed cell death upon their exposure to the VIP3A(a) protein.

The VIP3A(a) and VIP3A(b) proteins were discovered on the basis of their insecticidal properties against some lepidopteran insects. Therefore, we were interested in knowing whether the VIP3A(a) protein would induce an apoptotic pathway in gut cells of susceptible insects upon its ingestion and thus, it could exert its insecticidal properties by triggering an active process of cell death. Histological and histochemical studies have shown that the VIP3A(a) protein specifically targets the columnar cells of the midgut epithelium of susceptible insects provoking cell changes characterized by membrane protrusions and extensive vacuolization leading to cell death. These cytological changes induced by VIP3A(a) in insect gut cells resemble those described above for SF-9 cells. We then examined whether midgut epithelium cells of susceptible insects undergo endonucleolysis upon ingesting diet containing VIP3A(a) by in situ detection (Cuvillier, O., et al Nature 381:800–803 (1996)) of DNA fragmentation. When sections of midgut tissue from black cutworm larvae fed with diet either containing VIP3A (a) or control diet, nuclei staining indicative of DNA fragmentation was only detectable in the columnar cells of the midgut epithelium exposed to the VIP3A(a) protein. This result indicates that the VIP3A(a) protein induces an endonucleolysis process in the midgut epithelium cells concurrently with the cytological changes reported previously. It is our conclusion that the VIP3A(a) protein likely exerts its insecticidal properties by activating an apoptosis-type of programmed cell death of the midgut epithelium cells of susceptible insects.

Example 17

Isolation of the Receptor for VIP3A(a) from black cutworm

Black cutworm is sensitive to VIP3A(a) and therefore this insect was used for the isolation of the VIP3A(a) receptor. Midgut of third instar black cutworm larvae were collected by dissection and immediately frozen in liquid nitrogen. One gram of midgut tissue was used to isolate mRNA by following the protocol described in the two-hybrid cDNA library construction kit provided by Clontech (1997). Ten micrograms of poly $A^+$ RNA were used as starting material. In first strand synthesis, both random and lock-docking oligo$(dT)_{25}$d(A/C/G) primers are used in separate synthesis with MML reverse transcriptase. The second strand cDNA was achieved by an optimal ratio of DNA polymerase to Rnase H activity in the second-strand enzyme cocktail. The newly synthesized double stranded cDNA is then ligated to EcoRI-NotI-SalI adaptors. The cDNAs were ligated into pGAD10 (Vijaychander, S. et al. CLONTECHniques IX-3:8–10, 1994) which provides the activation domain. The vip3A(a) gene was engineered into the polylinker site of the plasmid pGBT9 in frame with the GAL4-DNA binding domain (Bartel, P. L. et al. Cellular Interactions in Development: A Practical Approach, pp. 153–179, Oxford University Press, 1993). The recombinant pGBT9-vip3A(a) was transformed into the yeast strain GGY1::171 (Gill, G. and Ptashne, M. Cell51:121–126, 1987) by electroporation (Estruch, J. J. et al BioTechniques 16:610–612, 1994). The transformed yeast was selected in minimal media without tryptophan (Bartel, P. L. et al. Cellular Interactions in Development: A Practical Approach, pp. 153–179, Oxford University Press, 1993). The expression of the VIP3A(a) protein in the recombinant yeast was confirmed by western analysis. The yeast strain GGY1::171- VIP3A(a) was transformed with the black cutworm cDNA library represented in pGAD10. GGY1::171 possess the HIS3 marker under the control of GAL4 recognition sites. The HIS3 gene allows a positive growth selection for clones that are transformed by two interacting hybrid constructs. After plating more than 200,000 recombinant clones, only one was able to grow in minimal media without histidine. The plasmid DNA of the positive yeast colony was isolated by the yeast lysis buffer method (Kaiser, P. and Auer, B. BioTechniques 14:552 (1993)) and electroporated into E. coli . The insert containing the cDNA was subcloned into the EcoRI site of the pBluescript (Stratagene) and sequenced by the dideoxy termination method of Sanger et al., Proc. Natl. Acad. Sci. U.S.A., 74: 5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

Example 18

Insect Cells Transformed with the Gene for the Receptor Exhibit Apoptosis when Exposed to the VIP3A(a) protein The receptor in black cutworm midgut cells for the VIP3A(a) protein was cloned into the XhoI-BamHI site of the Smart 2 cosmid vector (Speek, M. et al Gene 64: 173–177 (1988)), and the recombinant construct was used to transform the Schneider 2 (S2) Drosophila cell line using the calcium phosphate co-precipitation method (Clem, R. J. and Miller. L. K. Mol. Cel. Biol. 14: 5212–5222 (1994)). Smart 2 carries the selectable marker tet tetracycline) for bacterial transformation and the neo (neomycin) for Drosophila cell transformation. The neo selectable marker is expressed under the control of the Drosophila hsp70 promoter. The transformed S2 cells were selected in S2 Drosophila medium supplemented with 10% of Fetal Seroalbumin and with G418 (1 mg/ml) at 30° C. (see GIBCO catalogue 1997). Several stably transformed S2 cell lines were established after 45 days of selection in the medium described above.

The sensitivity of the S2 transformed cells to the VIP3A (a) was tested by adding VIP3A(a) protein (at a final concentration of 1,7 micrograms per ml) to the media containing the transformed S2 cells that have been previously heat shocked at 42° C. 30 min. The induction of apoptosis in transformed S2 cells was confirmed by both microscopical observations and by the TACS Kit, and in situ Apoptosis Detection kit (for detailed description, see Trevigen catalogue 1996).

Example 19

Isolating Homologues to the Receptor from Other Insects

The cells of the midgut epithelium of black cutworm larvae possess a receptor that is recognized by the VIP3A(a) protein. Receptors from other insects known to be susceptible to VIP3A(a) are isolated by identifying the DNA sequences in Southern analysis. DNA is prepared, enzyme restricted, run in agarose gels and blotted onto nitrocellulose and/or nylon filters. These filters are probed with the cDNA encoding the receptor from black cutworm using low stringency conditions of hybridization and washing. Genes with a similarity to the black cutworm receptor to VIP3A(a) lower than 50% were identified. The Southern analysis can also be probed against partial sequences of the cDNA which encode specific domains such as death domain or EGF-like motifs with the intention of isolating genes that contain similar domains even though they are functionally different to the black cutworm receptor to VIP3A(a).

The isolation of homologues to the black cutworm receptor to VIP3A(a) is be accomplished by the two hybrid system described in Fields, S. and Song, O.-K. Nature 340:245–246 (1989). Isolated mRNA is obtained from an organisms of interest, synthesize cDNAs and clone them into pGAD10 or equivalent plasmids. The cDNA library is co-transformed with the pGB9-bearing the vip3A(a) gene (or homologues of this gene) and rescued putative receptors in yeast by means of activating a marker based upon protein-protein interaction between the VIP3A(a) protein (or homologues) and the putative receptor.

Homologues to the black cutworm receptor to VIP3A(a) are isolated by expressing cDNAs libraries isolated from organisms of interests, cloned into appropriate expression vectors and transformed into host cells such as yeast or insect cells which are known not to have the ability to bind and/or be sensitive to VIP3A(a). The transformed cells are screened based on their gained property of binding VIP3A (a) or undergoing apoptotic responses when incubated with VIP3A(a). In this case, the protein VIP3A(a) is used as probe and its binding will be monitored either by antibodies against VIP3A(a) or by labels such as biotin attached to VIP3A(a).

Example 20

Screening for Novel Compounds that Induce Apoptosis in Insect Cells

Model cell lines for different orders of insects (some examples include Sf-9 cells for lepidopteran, Colorado potato beetle for coleopterans, S2 from Drosophila for dipterans) is used to screen for novel compounds whose mode of action is induction of apoptosis. The cells are grown in multi-well plates which are used for a high-throughput assay screening for thousands of compounds (both of large and small molecular weight). The compound(s) are added as single component or as mixtures. Compound(s) inducing apoptosis are identified as follows: 1) membrane protrusions are visible in the cell membrane, 2) a reorganization of the phosphatidylserine containing membrane lipids is detectable by using specific proteins with high affinity for phosphatidylserine such as Annexin-V linked to a visual marker, 3) cytoplasmic blebbing is visible in the cell cytoplasm, 4) active mitochondria can be visualized by using vital dyes such as rhodamine 123 that accumulate in mitochondria, 5) DNA fragmentation is detected either by DNA analysis in agarose gels, by ELISA detection of nucleosomal release or by in vivo detection of DNA nicking. All these cytological and molecular features are indicative of apoptosis.

The black cutworm receptor to VIP3A(a) is transformed into S2 cell line. Therefore, isogenic S2 lines are available with and without the said receptor. These cell lines are used to screen compounds that provide a differential response due to the presence of the said receptor. Transformed S2 cells undergoing apoptosis upon exposure to certain compounds are identified as indicated above. The differential response of the transformed versus the non-transformed cell is indicative that the action of the compound is mediated by the cloned receptor. Similar approaches are undertaken with insect cells transformed with receptors homologue to the black cutworm receptor to VIP3A(a).

All publications and patent applictions mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A microorganism comprising a recombinant DNA sequence which encodes a protein of the VIP3 class, wherein said DNA sequence is selected from the group consisting of SEQ ID NO:1, SEQ ID NO:3 and SEQ ID NO:5.

2. The microorganism of claim 1 wherein the DNA sequence is SEQ ID NO:1.

3. The microorganism of claim 1 wherein said microorganism is selected from the group consisting of bacteria, baculovirus, algae and fungi.

4. The microorganism of claim 3 wherein said microorganism is selected from the group consisting of Bacillus, Pseudomonas, Clavibacter, and Rhizobium.

5. The microorganism of claim 1 further comprising a second DNA sequence which encodes a second insecticidal protein.

6. The microorganism of claim 5 wherein said second DNA sequence encodes a δ-endotoxin or a vegetative insecticidal protein.

7. The microorganism of claim 6 wherein said second DNA sequence is a δ-endotoxin.

8. An entomocidal composition comprising microorganisms according to claim 1.

9. A recombinant DNA sequence which encodes a protein of the VIP3 class, wherein said DNA sequence is selected from the group consisting of SEQ ID NO:1, SEQ ID NO:3 and SEQ ID NO:5.

10. The recombinant DNA sequence of claim 9 wherein said DNA sequence is SEQ ID No:1.

11. The recombinant DNA sequence of claim 9 wherein the DNA sequence is a synthetic sequence which has been designed for optimum expression in a plant.

12. The recombinant DNA sequence of claim 11 wherein the plant is a maize plant.

13. An expression cassette comprising a heterologous promoter operably linked to the DNA sequence of claim 9.

14. The expression cassette of claim 13 wherein said promoter functions in plants is selected from the group consisting of inducible, constitutive, tissue-preferred and tissue-specific promoters.

15. The expression cassette of claim 13 wherein the promoter is selected from the group consisting of the ubiquitin, PEP carboxylase, LPT and MTL promoters.

16. A recombinant DNA sequence which encodes a protein of the VIP3 class wherein said sequence has a complement which hybridizes to a coding sequence selected from the group consisting of SEQ ID NO:1, SEQ ID NO:3 and SEQ ID NO:5 under hybridization conditions of 68° C. followed by washing at 68° C. in 2×SSC containing 0.1% SDS.

17. The recombinant DNA sequence of claim 16 wherein said DNA sequence has a complement which hybridizes to SEQ ID NO:1 under hybridization conditions of 68° C. followed by washing at 68° C. in 2×SSC containing 0.1% SDS.

18. The recombinant DNA sequence of claim 16 wherein said DNA sequence has a complement which hybridizes to SEQ ID NO:3 under hybridization conditions of 68° C. followed by washing at 68° C. in 2×SSC containing 0.1% SDS.

19. The recombinant DNA sequence of claim 16 wherein said DNA sequence has a complement which hybridizes to SEQ ID NO:5 under hybridization conditions of 68° C. followed by washing at 68° C. in 2×SSC containing 0.1% SDS.

20. The recombinant DNA sequence of claim 16 wherein the DNA sequence is a synthetic sequence which has been designed for optimum expression in a plant.

21. The recombinant DNA sequence of claim 20 wherein the plant is a maize plant.

22. An expression cassette comprising a heterologous promoter operably linked to the DNA sequence of claim 16.

23. The expression cassette of claim 22 wherein said promoter functions in plants is selected from the group consisting of inducible, constitutive, tissue-preferred and tissue-specific promoters.

24. The expression cassette of claim 22 wherein the promoter is selected from the group consisting of the ubiquitin, PEP carboxylase, LPT and MTL promoters.

25. A microorganism comprising a recombinant DNA sequence which encodes a protein of the VIP3 class wherein said sequence has a complement which hybridizes to a coding sequence selected from the group consisting of SEQ ID NO:1, SEQ ID NO:3 band SEQ ID NO:5 under hybridization conditions, of 68° C. followed by washing at 68° C. in 2×SSC containing 0.1% SDS.

26. The microorganism of claim 25 wherein said microorganism is selected from the group consisting of bacteria, baculovirus, algae and fungi.

27. The microorganism of claim 26 wherein said microorganism is selected from the group consisting of Bacillus, Pseudomonas, Clavibacter, and Rhizobium.

28. The microorganism of claim 25 further comprising a second DNA sequence which encodes a second insecticidal protein.

29. The microorganism of claim 28 wherein said second DNA sequence encodes a δ-endotoxin or a vegetative insecticidal protein.

30. The microorganism of claim 29 wherein said second DNA sequence is a δ-endotoxin.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 2378 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: CDS
        ( B ) LOCATION: 9..2375
        ( D ) OTHER INFORMATION: /note= "Native DNA sequence encoding VIP3A(a) protein from AB88 as contained in pCIB7104"

( x i ) SEQUENCE DESCRIPTION: SEQ ID NO:1:

```
AGATGAAC ATG AAC AAG AAT AAT ACT AAA TTA AGC ACA AGA GCC TTA CCA        50
         Met Asn Lys Asn Asn Thr Lys Leu Ser Thr Arg Ala Leu Pro
          1               5                  10

AGT TTT ATT GAT TAT TTT AAT GGC ATT TAT GGA TTT GCC ACT GGT ATC         98
Ser Phe Ile Asp Tyr Phe Asn Gly Ile Tyr Gly Phe Ala Thr Gly Ile
 15              20              25                  30

AAA GAC ATT ATG AAC ATG ATT TTT AAA ACG GAT ACA GGT GGT GAT CTA        146
Lys Asp Ile Met Asn Met Ile Phe Lys Thr Asp Thr Gly Gly Asp Leu
             35              40                  45

ACC CTA GAC GAA ATT TTA AAG AAT CAG CAG TTA CTA AAT GAT ATT TCT        194
Thr Leu Asp Glu Ile Leu Lys Asn Gln Gln Leu Leu Asn Asp Ile Ser
         50              55                  60

GGT AAA TTG GAT GGG GTG AAT GGA AGC TTA AAT GAT CTT ATC GCA CAG        242
Gly Lys Leu Asp Gly Val Asn Gly Ser Leu Asn Asp Leu Ile Ala Gln
         65                  70              75

GGA AAC TTA AAT ACA GAA TTA TCT AAG GAA ATA TTA AAA ATT GCA AAT        290
Gly Asn Leu Asn Thr Glu Leu Ser Lys Glu Ile Leu Lys Ile Ala Asn
         80              85                  90

GAA CAA AAT CAA GTT TTA AAT GAT GTT AAT AAC AAA CTC GAT GCG ATA        338
Glu Gln Asn Gln Val Leu Asn Asp Val Asn Asn Lys Leu Asp Ala Ile
 95              100                 105                 110

AAT ACG ATG CTT CGG GTA TAT CTA CCT AAA ATT ACC TCT ATG TTG AGT        386
Asn Thr Met Leu Arg Val Tyr Leu Pro Lys Ile Thr Ser Met Leu Ser
             115                 120                 125

GAT GTA ATG AAA CAA AAT TAT GCG CTA AGT CTG CAA ATA GAA TAC TTA        434
Asp Val Met Lys Gln Asn Tyr Ala Leu Ser Leu Gln Ile Glu Tyr Leu
             130                 135                 140

AGT AAA CAA TTG CAA GAG ATT TCT GAT AAG TTG GAT ATT ATT AAT GTA        482
Ser Lys Gln Leu Gln Glu Ile Ser Asp Lys Leu Asp Ile Ile Asn Val
             145                 150                 155

AAT GTA CTT ATT AAC TCT ACA CTT ACT GAA ATT ACA CCT GCG TAT CAA        530
Asn Val Leu Ile Asn Ser Thr Leu Thr Glu Ile Thr Pro Ala Tyr Gln
         160                 165                 170

AGG ATT AAA TAT GTG AAC GAA AAA TTT GAG GAA TTA ACT TTT GCT ACA        578
Arg Ile Lys Tyr Val Asn Glu Lys Phe Glu Glu Leu Thr Phe Ala Thr
 175                 180                 185                 190

GAA ACT AGT TCA AAA GTA AAA AAG GAT GGC TCT CCT GCA GAT ATT CTT        626
Glu Thr Ser Ser Lys Val Lys Lys Asp Gly Ser Pro Ala Asp Ile Leu
             195                 200                 205
```

| | | | | | | | | | | | | | | | | |
|---|---|---|---|---|---|---|---|---|---|---|---|---|---|---|---|---|
| GAT | GAG | TTA | ACT | GAG | TTA | ACT | GAA | CTA | GCG | AAA | AGT | GTA | ACA | AAA | AAT | 674 |
| Asp | Glu | Leu | Thr | Glu | Leu | Thr | Glu | Leu | Ala | Lys | Ser | Val | Thr | Lys | Asn | |
| | | | 210 | | | | 215 | | | | | 220 | | | | |
| GAT | GTG | GAT | GGT | TTT | GAA | TTT | TAC | CTT | AAT | ACA | TTC | CAC | GAT | GTA | ATG | 722 |
| Asp | Val | Asp | Gly | Phe | Glu | Phe | Tyr | Leu | Asn | Thr | Phe | His | Asp | Val | Met | |
| | | 225 | | | | | 230 | | | | | 235 | | | | |
| GTA | GGA | AAT | AAT | TTA | TTC | GGG | CGT | TCA | GCT | TTA | AAA | ACT | GCA | TCG | GAA | 770 |
| Val | Gly | Asn | Asn | Leu | Phe | Gly | Arg | Ser | Ala | Leu | Lys | Thr | Ala | Ser | Glu | |
| 240 | | | | | 245 | | | | | 250 | | | | | | |
| TTA | ATT | ACT | AAA | GAA | AAT | GTG | AAA | ACA | AGT | GGC | AGT | GAG | GTC | GGA | AAT | 818 |
| Leu | Ile | Thr | Lys | Glu | Asn | Val | Lys | Thr | Ser | Gly | Ser | Glu | Val | Gly | Asn | |
| 255 | | | | | 260 | | | | | 265 | | | | | 270 | |
| GTT | TAT | AAC | TTC | TTA | ATT | GTA | TTA | ACA | GCT | CTG | CAA | GCC | CAA | GCT | TTT | 866 |
| Val | Tyr | Asn | Phe | Leu | Ile | Val | Leu | Thr | Ala | Leu | Gln | Ala | Gln | Ala | Phe | |
| | | | | 275 | | | | | 280 | | | | | 285 | | |
| CTT | ACT | TTA | ACA | ACA | TGC | CGA | AAA | TTA | TTA | GGC | TTA | GCA | GAT | ATT | GAT | 914 |
| Leu | Thr | Leu | Thr | Thr | Cys | Arg | Lys | Leu | Leu | Gly | Leu | Ala | Asp | Ile | Asp | |
| | | | 290 | | | | 295 | | | | | 300 | | | | |
| TAT | ACT | TCT | ATT | ATG | AAT | GAA | CAT | TTA | AAT | AAG | GAA | AAA | GAG | GAA | TTT | 962 |
| Tyr | Thr | Ser | Ile | Met | Asn | Glu | His | Leu | Asn | Lys | Glu | Lys | Glu | Glu | Phe | |
| | | 305 | | | | | 310 | | | | | 315 | | | | |
| AGA | GTA | AAC | ATC | CTC | CCT | ACA | CTT | TCT | AAT | ACT | TTT | TCT | AAT | CCT | AAT | 1010 |
| Arg | Val | Asn | Ile | Leu | Pro | Thr | Leu | Ser | Asn | Thr | Phe | Ser | Asn | Pro | Asn | |
| 320 | | | | | 325 | | | | | 330 | | | | | | |
| TAT | GCA | AAA | GTT | AAA | GGA | AGT | GAT | GAA | GAT | GCA | AAG | ATG | ATT | GTG | GAA | 1058 |
| Tyr | Ala | Lys | Val | Lys | Gly | Ser | Asp | Glu | Asp | Ala | Lys | Met | Ile | Val | Glu | |
| 335 | | | | | 340 | | | | | 345 | | | | | 350 | |
| GCT | AAA | CCA | GGA | CAT | GCA | TTG | ATT | GGG | TTT | GAA | ATT | AGT | AAT | GAT | TCA | 1106 |
| Ala | Lys | Pro | Gly | His | Ala | Leu | Ile | Gly | Phe | Glu | Ile | Ser | Asn | Asp | Ser | |
| | | | | 355 | | | | | 360 | | | | | 365 | | |
| ATT | ACA | GTA | TTA | AAA | GTA | TAT | GAG | GCT | AAG | CTA | AAA | CAA | AAT | TAT | CAA | 1154 |
| Ile | Thr | Val | Leu | Lys | Val | Tyr | Glu | Ala | Lys | Leu | Lys | Gln | Asn | Tyr | Gln | |
| | | | 370 | | | | 375 | | | | | 380 | | | | |
| GTC | GAT | AAG | GAT | TCC | TTA | TCG | GAA | GTT | ATT | TAT | GGT | GAT | ATG | GAT | AAA | 1202 |
| Val | Asp | Lys | Asp | Ser | Leu | Ser | Glu | Val | Ile | Tyr | Gly | Asp | Met | Asp | Lys | |
| | | 385 | | | | | 390 | | | | | 395 | | | | |
| TTA | TTG | TGC | CCA | GAT | CAA | TCT | GAA | CAA | ATC | TAT | TAT | ACA | AAT | AAC | ATA | 1250 |
| Leu | Leu | Cys | Pro | Asp | Gln | Ser | Glu | Gln | Ile | Tyr | Tyr | Thr | Asn | Asn | Ile | |
| 400 | | | | | 405 | | | | | 410 | | | | | | |
| GTA | TTT | CCA | AAT | GAA | TAT | GTA | ATT | ACT | AAA | ATT | GAT | TTC | ACT | AAA | AAA | 1298 |
| Val | Phe | Pro | Asn | Glu | Tyr | Val | Ile | Thr | Lys | Ile | Asp | Phe | Thr | Lys | Lys | |
| 415 | | | | | 420 | | | | | 425 | | | | | 430 | |
| ATG | AAA | ACT | TTA | AGA | TAT | GAG | GTA | ACA | GCG | AAT | TTT | TAT | GAT | TCT | TCT | 1346 |
| Met | Lys | Thr | Leu | Arg | Tyr | Glu | Val | Thr | Ala | Asn | Phe | Tyr | Asp | Ser | Ser | |
| | | | | 435 | | | | | 440 | | | | | 445 | | |
| ACA | GGA | GAA | ATT | GAC | TTA | AAT | AAG | AAA | AAA | GTA | GAA | TCA | AGT | GAA | GCG | 1394 |
| Thr | Gly | Glu | Ile | Asp | Leu | Asn | Lys | Lys | Lys | Val | Glu | Ser | Ser | Glu | Ala | |
| | | | | 450 | | | | | 455 | | | | | 460 | | |
| GAG | TAT | AGA | ACG | TTA | AGT | GCT | AAT | GAT | GAT | GGG | GTG | TAT | ATG | CCG | TTA | 1442 |
| Glu | Tyr | Arg | Thr | Leu | Ser | Ala | Asn | Asp | Asp | Gly | Val | Tyr | Met | Pro | Leu | |
| | | 465 | | | | | 470 | | | | | 475 | | | | |
| GGT | GTC | ATC | AGT | GAA | ACA | TTT | TTG | ACT | CCG | ATT | AAT | GGG | TTT | GGC | CTC | 1490 |
| Gly | Val | Ile | Ser | Glu | Thr | Phe | Leu | Thr | Pro | Ile | Asn | Gly | Phe | Gly | Leu | |
| | | 480 | | | | | 485 | | | | | 490 | | | | |
| CAA | GCT | GAT | GAA | AAT | TCA | AGA | TTA | ATT | ACT | TTA | ACA | TGT | AAA | TCA | TAT | 1538 |
| Gln | Ala | Asp | Glu | Asn | Ser | Arg | Leu | Ile | Thr | Leu | Thr | Cys | Lys | Ser | Tyr | |
| 495 | | | | | 500 | | | | | 505 | | | | | 510 | |
| TTA | AGA | GAA | CTA | CTG | CTA | GCA | ACA | GAC | TTA | AGC | AAT | AAA | GAA | ACT | AAA | 1586 |
| Leu | Arg | Glu | Leu | Leu | Leu | Ala | Thr | Asp | Leu | Ser | Asn | Lys | Glu | Thr | Lys | |
| | | | | 515 | | | | | 520 | | | | | 525 | | |

```
TTG  ATC  GTC  CCG  CCA  AGT  GGT  TTT  ATT  AGC  AAT  ATT  GTA  GAG  AAC  GGG    1634
Leu  Ile  Val  Pro  Pro  Ser  Gly  Phe  Ile  Ser  Asn  Ile  Val  Glu  Asn  Gly
               530                 535                 540

TCC  ATA  GAA  GAG  GAC  AAT  TTA  GAG  CCG  TGG  AAA  GCA  AAT  AAT  AAG  AAT    1682
Ser  Ile  Glu  Glu  Asp  Asn  Leu  Glu  Pro  Trp  Lys  Ala  Asn  Asn  Lys  Asn
               545                 550                 555

GCG  TAT  GTA  GAT  CAT  ACA  GGC  GGA  GTG  AAT  GGA  ACT  AAA  GCT  TTA  TAT    1730
Ala  Tyr  Val  Asp  His  Thr  Gly  Gly  Val  Asn  Gly  Thr  Lys  Ala  Leu  Tyr
          560                 565                 570

GTT  CAT  AAG  GAC  GGA  GGA  ATT  TCA  CAA  TTT  ATT  GGA  GAT  AAG  TTA  AAA    1778
Val  His  Lys  Asp  Gly  Gly  Ile  Ser  Gln  Phe  Ile  Gly  Asp  Lys  Leu  Lys
575                      580                 585                      590

CCG  AAA  ACT  GAG  TAT  GTA  ATC  CAA  TAT  ACT  GTT  AAA  GGA  AAA  CCT  TCT    1826
Pro  Lys  Thr  Glu  Tyr  Val  Ile  Gln  Tyr  Thr  Val  Lys  Gly  Lys  Pro  Ser
                    595                 600                      605

ATT  CAT  TTA  AAA  GAT  GAA  AAT  ACT  GGA  TAT  ATT  CAT  TAT  GAA  GAT  ACA    1874
Ile  His  Leu  Lys  Asp  Glu  Asn  Thr  Gly  Tyr  Ile  His  Tyr  Glu  Asp  Thr
               610                 615                 620

AAT  AAT  AAT  TTA  GAA  GAT  TAT  CAA  ACT  ATT  AAT  AAA  CGT  TTT  ACT  ACA    1922
Asn  Asn  Asn  Leu  Glu  Asp  Tyr  Gln  Thr  Ile  Asn  Lys  Arg  Phe  Thr  Thr
          625                 630                 635

GGA  ACT  GAT  TTA  AAG  GGA  GTG  TAT  TTA  ATT  TTA  AAA  AGT  CAA  AAT  GGA    1970
Gly  Thr  Asp  Leu  Lys  Gly  Val  Tyr  Leu  Ile  Leu  Lys  Ser  Gln  Asn  Gly
640                      645                 650

GAT  GAA  GCT  TGG  GGA  GAT  AAC  TTT  ATT  ATT  TTG  GAA  ATT  AGT  CCT  TCT    2018
Asp  Glu  Ala  Trp  Gly  Asp  Asn  Phe  Ile  Ile  Leu  Glu  Ile  Ser  Pro  Ser
655                      660                 665                      670

GAA  AAG  TTA  TTA  AGT  CCA  GAA  TTA  ATT  AAT  ACA  AAT  AAT  TGG  ACG  AGT    2066
Glu  Lys  Leu  Leu  Ser  Pro  Glu  Leu  Ile  Asn  Thr  Asn  Asn  Trp  Thr  Ser
               675                 680                 685

ACG  GGA  TCA  ACT  AAT  ATT  AGC  GGT  AAT  ACA  CTC  ACT  CTT  TAT  CAG  GGA    2114
Thr  Gly  Ser  Thr  Asn  Ile  Ser  Gly  Asn  Thr  Leu  Thr  Leu  Tyr  Gln  Gly
               690                 695                 700

GGA  CGA  GGG  ATT  CTA  AAA  CAA  AAC  CTT  CAA  TTA  GAT  AGT  TTT  TCA  ACT    2162
Gly  Arg  Gly  Ile  Leu  Lys  Gln  Asn  Leu  Gln  Leu  Asp  Ser  Phe  Ser  Thr
               705                 710                 715

TAT  AGA  GTG  TAT  TTT  TCT  GTG  TCC  GGA  GAT  GCT  AAT  GTA  AGG  ATT  AGA    2210
Tyr  Arg  Val  Tyr  Phe  Ser  Val  Ser  Gly  Asp  Ala  Asn  Val  Arg  Ile  Arg
     720                 725                      730

AAT  TCT  AGG  GAA  GTG  TTA  TTT  GAA  AAA  AGA  TAT  ATG  AGC  GGT  GCT  AAA    2258
Asn  Ser  Arg  Glu  Val  Leu  Phe  Glu  Lys  Arg  Tyr  Met  Ser  Gly  Ala  Lys
735                      740                 745                      750

GAT  GTT  TCT  GAA  ATG  TTC  ACT  ACA  AAA  TTT  GAG  AAA  GAT  AAC  TTT  TAT    2306
Asp  Val  Ser  Glu  Met  Phe  Thr  Thr  Lys  Phe  Glu  Lys  Asp  Asn  Phe  Tyr
                    755                 760                      765

ATA  GAG  CTT  TCT  CAA  GGG  AAT  AAT  TTA  TAT  GGT  GGT  CCT  ATT  GTA  CAT    2354
Ile  Glu  Leu  Ser  Gln  Gly  Asn  Asn  Leu  Tyr  Gly  Gly  Pro  Ile  Val  His
               770                 775                 780

TTT  TAC  GAT  GTC  TCT  ATT  AAG  TAA                                            2378
Phe  Tyr  Asp  Val  Ser  Ile  Lys
               785
```

( 2 ) INFORMATION FOR SEQ ID NO:2:

( i ) SEQUENCE CHARACTERISTICS:
    ( A ) LENGTH: 789 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
|Met|Asn|Lys|Asn|Asn|Thr|Lys|Leu|Ser|Thr|Arg|Ala|Leu|Pro|Ser|Phe|
|1| | | |5| | | |10| | | | |15| |
|Ile|Asp|Tyr|Phe|Asn|Gly|Ile|Tyr|Gly|Phe|Ala|Thr|Gly|Ile|Lys|Asp|
| | | |20| | | |25| | | |30| | | | |
|Ile|Met|Asn|Met|Ile|Phe|Lys|Thr|Asp|Thr|Gly|Gly|Asp|Leu|Thr|Leu|
| | |35| | | |40| | | | |45| | | | |
|Asp|Glu|Ile|Leu|Lys|Asn|Gln|Gln|Leu|Leu|Asn|Asp|Ile|Ser|Gly|Lys|
| |50| | | |55| | | | |60| | | | | |
|Leu|Asp|Gly|Val|Asn|Gly|Ser|Leu|Asn|Asp|Leu|Ile|Ala|Gln|Gly|Asn|
|65| | | |70| | | |75| | | | | | |80|
|Leu|Asn|Thr|Glu|Leu|Ser|Lys|Glu|Ile|Leu|Lys|Ile|Ala|Asn|Glu|Gln|
| | | |85| | | |90| | | | | |95| | |
|Asn|Gln|Val|Leu|Asn|Asp|Val|Asn|Asn|Lys|Leu|Asp|Ala|Ile|Asn|Thr|
| | |100| | | |105| | | | |110| | | | |
|Met|Leu|Arg|Val|Tyr|Leu|Pro|Lys|Ile|Thr|Ser|Met|Leu|Ser|Asp|Val|
| | |115| | | |120| | | |125| | | | | |
|Met|Lys|Gln|Asn|Tyr|Ala|Leu|Ser|Leu|Gln|Ile|Glu|Tyr|Leu|Ser|Lys|
| |130| | | |135| | | |140| | | | | | |
|Gln|Leu|Gln|Glu|Ile|Ser|Asp|Lys|Leu|Asp|Ile|Ile|Asn|Val|Asn|Val|
|145| | | |150| | | |155| | | | | |160| |
|Leu|Ile|Asn|Ser|Thr|Leu|Thr|Glu|Ile|Thr|Pro|Ala|Tyr|Gln|Arg|Ile|
| | | |165| | | |170| | | | |175| | | |
|Lys|Tyr|Val|Asn|Glu|Lys|Phe|Glu|Glu|Leu|Thr|Phe|Ala|Thr|Glu|Thr|
| | |180| | | |185| | | | |190| | | | |
|Ser|Ser|Lys|Val|Lys|Lys|Asp|Gly|Ser|Pro|Ala|Asp|Ile|Leu|Asp|Glu|
| |195| | | |200| | | | |205| | | | | |
|Leu|Thr|Glu|Leu|Thr|Glu|Leu|Ala|Lys|Ser|Val|Thr|Lys|Asn|Asp|Val|
|210| | | |215| | | |220| | | | | | | |
|Asp|Gly|Phe|Glu|Phe|Tyr|Leu|Asn|Thr|Phe|His|Asp|Val|Met|Val|Gly|
|225| | | |230| | | |235| | | | | |240| |
|Asn|Asn|Leu|Phe|Gly|Arg|Ser|Ala|Leu|Lys|Thr|Ala|Ser|Glu|Leu|Ile|
| | |245| | | |250| | | | |255| | | | |
|Thr|Lys|Glu|Asn|Val|Lys|Thr|Ser|Gly|Ser|Glu|Val|Gly|Asn|Val|Tyr|
| |260| | | |265| | | |270| | | | | | |
|Asn|Phe|Leu|Ile|Val|Leu|Thr|Ala|Leu|Gln|Ala|Gln|Ala|Phe|Leu|Thr|
| |275| | | |280| | | |285| | | | | | |
|Leu|Thr|Thr|Cys|Arg|Lys|Leu|Leu|Gly|Leu|Ala|Asp|Ile|Asp|Tyr|Thr|
|290| | | |295| | | |300| | | | | | | |
|Ser|Ile|Met|Asn|Glu|His|Leu|Asn|Lys|Glu|Lys|Glu|Glu|Phe|Arg|Val|
|305| | | |310| | | |315| | | | | |320| |
|Asn|Ile|Leu|Pro|Thr|Leu|Ser|Asn|Thr|Phe|Ser|Asn|Pro|Asn|Tyr|Ala|
| | |325| | | |330| | | | |335| | | | |
|Lys|Val|Lys|Gly|Ser|Asp|Glu|Asp|Ala|Lys|Met|Ile|Val|Glu|Ala|Lys|
| |340| | | |345| | | |350| | | | | | |
|Pro|Gly|His|Ala|Leu|Ile|Gly|Phe|Glu|Ile|Ser|Asn|Asp|Ser|Ile|Thr|
| |355| | | |360| | | |365| | | | | | |
|Val|Leu|Lys|Val|Tyr|Glu|Ala|Lys|Leu|Lys|Gln|Asn|Tyr|Gln|Val|Asp|
|370| | | |375| | | |380| | | | | | | |
|Lys|Asp|Ser|Leu|Ser|Glu|Val|Ile|Tyr|Gly|Asp|Met|Asp|Lys|Leu|Leu|
|385| | | |390| | | |395| | | | | | |400|
|Cys|Pro|Asp|Gln|Ser|Glu|Gln|Ile|Tyr|Tyr|Thr|Asn|Asn|Ile|Val|Phe|
| | |405| | | |410| | | | |415| | | | |
|Pro|Asn|Glu|Tyr|Val|Ile|Thr|Lys|Ile|Asp|Phe|Thr|Lys|Lys|Met|Lys|

|     |     |     |     |     | 420 |     |     |     |     | 425 |     |     |     |     | 430 |     |     |
|-----|-----|-----|-----|-----|-----|-----|-----|-----|-----|-----|-----|-----|-----|-----|-----|-----|-----|
| Thr | Leu | Arg | Tyr | Glu | Val | Thr | Ala | Asn | Phe | Tyr | Asp | Ser | Ser | Thr | Gly |
|     |     | 435 |     |     |     |     | 440 |     |     |     | 445 |     |     |     |     |
| Glu | Ile | Asp | Leu | Asn | Lys | Lys | Val | Glu | Ser | Ser | Glu | Ala | Glu | Tyr |
| 450 |     |     |     |     | 455 |     |     |     |     | 460 |     |     |     |     |
| Arg | Thr | Leu | Ser | Ala | Asn | Asp | Asp | Gly | Val | Tyr | Met | Pro | Leu | Gly | Val |
| 465 |     |     |     | 470 |     |     |     |     | 475 |     |     |     |     | 480 |
| Ile | Ser | Glu | Thr | Phe | Leu | Thr | Pro | Ile | Asn | Gly | Phe | Gly | Leu | Gln | Ala |
|     |     |     |     | 485 |     |     |     | 490 |     |     |     |     | 495 |     |
| Asp | Glu | Asn | Ser | Arg | Leu | Ile | Thr | Leu | Thr | Cys | Lys | Ser | Tyr | Leu | Arg |
|     |     |     | 500 |     |     |     |     | 505 |     |     |     | 510 |     |     |
| Glu | Leu | Leu | Leu | Ala | Thr | Asp | Leu | Ser | Asn | Lys | Glu | Thr | Lys | Leu | Ile |
|     |     | 515 |     |     |     |     | 520 |     |     |     | 525 |     |     |     |
| Val | Pro | Pro | Ser | Gly | Phe | Ile | Ser | Asn | Ile | Val | Glu | Asn | Gly | Ser | Ile |
|     | 530 |     |     |     |     | 535 |     |     |     | 540 |     |     |     |     |
| Glu | Glu | Asp | Asn | Leu | Glu | Pro | Trp | Lys | Ala | Asn | Asn | Lys | Asn | Ala | Tyr |
| 545 |     |     |     |     | 550 |     |     |     | 555 |     |     |     |     | 560 |
| Val | Asp | His | Thr | Gly | Gly | Val | Asn | Gly | Thr | Lys | Ala | Leu | Tyr | Val | His |
|     |     |     |     | 565 |     |     |     |     | 570 |     |     |     | 575 |     |
| Lys | Asp | Gly | Gly | Ile | Ser | Gln | Phe | Ile | Gly | Asp | Lys | Leu | Lys | Pro | Lys |
|     |     |     | 580 |     |     |     |     | 585 |     |     |     |     | 590 |     |
| Thr | Glu | Tyr | Val | Ile | Gln | Tyr | Thr | Val | Lys | Gly | Lys | Pro | Ser | Ile | His |
|     |     | 595 |     |     |     |     | 600 |     |     |     |     | 605 |     |     |
| Leu | Lys | Asp | Glu | Asn | Thr | Gly | Tyr | Ile | His | Tyr | Glu | Asp | Thr | Asn | Asn |
|     | 610 |     |     |     |     | 615 |     |     |     |     | 620 |     |     |     |
| Asn | Leu | Glu | Asp | Tyr | Gln | Thr | Ile | Asn | Lys | Arg | Phe | Thr | Thr | Gly | Thr |
| 625 |     |     |     |     | 630 |     |     |     |     | 635 |     |     |     |     | 640 |
| Asp | Leu | Lys | Gly | Val | Tyr | Leu | Ile | Leu | Lys | Ser | Gln | Asn | Gly | Asp | Glu |
|     |     |     |     | 645 |     |     |     |     | 650 |     |     |     |     | 655 |
| Ala | Trp | Gly | Asp | Asn | Phe | Ile | Ile | Leu | Glu | Ile | Ser | Pro | Ser | Glu | Lys |
|     |     |     | 660 |     |     |     |     | 665 |     |     |     | 670 |     |     |
| Leu | Leu | Ser | Pro | Glu | Leu | Ile | Asn | Thr | Asn | Asn | Trp | Thr | Ser | Thr | Gly |
|     |     | 675 |     |     |     |     | 680 |     |     |     | 685 |     |     |     |
| Ser | Thr | Asn | Ile | Ser | Gly | Asn | Thr | Leu | Thr | Leu | Tyr | Gln | Gly | Gly | Arg |
|     | 690 |     |     |     |     | 695 |     |     |     | 700 |     |     |     |     |
| Gly | Ile | Leu | Lys | Gln | Asn | Leu | Gln | Leu | Asp | Ser | Phe | Ser | Thr | Tyr | Arg |
| 705 |     |     |     |     | 710 |     |     |     | 715 |     |     |     |     | 720 |
| Val | Tyr | Phe | Ser | Val | Ser | Gly | Asp | Ala | Asn | Val | Arg | Ile | Arg | Asn | Ser |
|     |     |     |     | 725 |     |     |     | 730 |     |     |     |     | 735 |     |
| Arg | Glu | Val | Leu | Phe | Glu | Lys | Arg | Tyr | Met | Ser | Gly | Ala | Lys | Asp | Val |
|     |     |     | 740 |     |     |     |     | 745 |     |     |     | 750 |     |     |
| Ser | Glu | Met | Phe | Thr | Thr | Lys | Phe | Glu | Lys | Asp | Asn | Phe | Tyr | Ile | Glu |
|     |     | 755 |     |     |     |     | 760 |     |     |     | 765 |     |     |     |
| Leu | Ser | Gln | Gly | Asn | Asn | Leu | Tyr | Gly | Gly | Pro | Ile | Val | His | Phe | Tyr |
|     | 770 |     |     |     |     | 775 |     |     |     | 780 |     |     |     |     |
| Asp | Val | Ser | Ile | Lys |
| 785 |     |     |     |     |

( 2 ) INFORMATION FOR SEQ ID NO:3:

( i ) SEQUENCE CHARACTERISTICS:
        ( A ) LENGTH: 2612 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i x ) FEATURE:
    ( A ) NAME/KEY: CDS
    ( B ) LOCATION: 118..2484
    ( D ) OTHER INFORMATION: /note= "Native DNA sequence encoding VIP3A(b) from AB424"

( x i ) SEQUENCE DESCRIPTION: SEQ ID NO:3:

```
ATTGAAATTG ATAAAAGTT ATGAGTGTTT AATAATCAGT AATTACCAAT AAAGAATTAA         60

GAATACAAGT TTACAAGAAA TAAGTGTTAC AAAAAATAGC TGAAAAGGAA GATGAAC          117

ATG AAC AAG AAT AAT ACT AAA TTA AGC ACA AGA GCC TTA CCA AGT TTT         165
Met Asn Lys Asn Asn Thr Lys Leu Ser Thr Arg Ala Leu Pro Ser Phe
790             795             800             805

ATT GAT TAT TTC AAT GGC ATT TAT GGA TTT GCC ACT GGT ATC AAA GAC         213
Ile Asp Tyr Phe Asn Gly Ile Tyr Gly Phe Ala Thr Gly Ile Lys Asp
                810             815             820

ATT ATG AAC ATG ATT TTT AAA ACG GAT ACA GGT GGT GAT CTA ACC CTA         261
Ile Met Asn Met Ile Phe Lys Thr Asp Thr Gly Gly Asp Leu Thr Leu
            825             830             835

GAC GAA ATT TTA AAG AAT CAG CAG CTA CTA AAT GAT ATT TCT GGT AAA         309
Asp Glu Ile Leu Lys Asn Gln Gln Leu Leu Asn Asp Ile Ser Gly Lys
        840             845             850

TTG GAT GGG GTG AAT GGA AGC TTA AAT GAT CTT ATC GCA CAG GGA AAC         357
Leu Asp Gly Val Asn Gly Ser Leu Asn Asp Leu Ile Ala Gln Gly Asn
    855             860             865

TTA AAT ACA GAA TTA TCT AAG GAA ATA TTA AAA ATT GCA AAT GAA CAA         405
Leu Asn Thr Glu Leu Ser Lys Glu Ile Leu Lys Ile Ala Asn Glu Gln
870             875             880             885

AAT CAA GTT TTA AAT GAT GTT AAT AAC AAA CTC GAT GCG ATA AAT ACG         453
Asn Gln Val Leu Asn Asp Val Asn Asn Lys Leu Asp Ala Ile Asn Thr
                890             895             900

ATG CTT CGG GTA TAT CTA CCT AAA ATT ACC TCT ATG TTG AGT GAT GTA         501
Met Leu Arg Val Tyr Leu Pro Lys Ile Thr Ser Met Leu Ser Asp Val
            905             910             915

ATG AAA CAA AAT TAT GCG CTA AGT CTG CAA ATA GAA TAC TTA AGT AAA         549
Met Lys Gln Asn Tyr Ala Leu Ser Leu Gln Ile Glu Tyr Leu Ser Lys
        920             925             930

CAA TTG CAA GAG ATT TCT GAT AAG TTG GAT ATT ATT AAT GTA AAT GTA         597
Gln Leu Gln Glu Ile Ser Asp Lys Leu Asp Ile Ile Asn Val Asn Val
    935             940             945

CTT ATT AAC TCT ACA CTT ACT GAA ATT ACA CCT GCG TAT CAA AGG ATT         645
Leu Ile Asn Ser Thr Leu Thr Glu Ile Thr Pro Ala Tyr Gln Arg Ile
950             955             960             965

AAA TAT GTG AAC GAA AAA TTT GAG GAA TTA ACT TTT GCT ACA GAA ACT         693
Lys Tyr Val Asn Glu Lys Phe Glu Glu Leu Thr Phe Ala Thr Glu Thr
                970             975             980

AGT TCA AAA GTA AAA AAG GAT GGC TCT CCT GCA GAT ATT CGT GAT GAG         741
Ser Ser Lys Val Lys Lys Asp Gly Ser Pro Ala Asp Ile Arg Asp Glu
            985             990             995

TTA ACT GAG TTA ACT GAA CTA GCG AAA AGT GTA ACA AAA AAT GAT GTG         789
Leu Thr Glu Leu Thr Glu Leu Ala Lys Ser Val Thr Lys Asn Asp Val
        1000            1005            1010

GAT GGT TTT GAA TTT TAC CTT AAT ACA TTC CAC GAT GTA ATG GTA GGA         837
Asp Gly Phe Glu Phe Tyr Leu Asn Thr Phe His Asp Val Met Val Gly
    1015            1020            1025

AAT AAT TTA TTC GGG CGT TCA GCT TTA AAA ACT GCA TCG GAA TTA ATT         885
Asn Asn Leu Phe Gly Arg Ser Ala Leu Lys Thr Ala Ser Glu Leu Ile
1030            1035            1040            1045
```

| | | | | | | | | | | | | | | | | |
|---|---|---|---|---|---|---|---|---|---|---|---|---|---|---|---|---|
| ACT | AAA | GAA | AAT | GTG | AAA | ACA | AGT | GGC | AGT | GAG | GTC | GGA | AAT | GTT | TAT | 933 |
| Thr | Lys | Glu | Asn | Val | Lys | Thr | Ser | Gly | Ser | Glu | Val | Gly | Asn | Val | Tyr | |
| | | | | 1050 | | | | 1055 | | | | | 1060 | | | |
| AAC | TTC | CTA | ATT | GTA | TTA | ACA | GCT | CTG | CAA | GCA | AAA | GCT | TTT | CTT | ACT | 981 |
| Asn | Phe | Leu | Ile | Val | Leu | Thr | Ala | Leu | Gln | Ala | Lys | Ala | Phe | Leu | Thr | |
| | | | 1065 | | | | 1070 | | | | 1075 | | | | | |
| TTA | ACA | CCA | TGC | CGA | AAA | TTA | TTA | GGC | TTA | GCA | GAT | ATT | GAT | TAT | ACT | 1029 |
| Leu | Thr | Pro | Cys | Arg | Lys | Leu | Leu | Gly | Leu | Ala | Asp | Ile | Asp | Tyr | Thr | |
| | | 1080 | | | | | 1085 | | | | | 1090 | | | | |
| TCT | ATT | ATG | AAT | GAA | CAT | TTA | AAT | AAG | GAA | AAA | GAG | GAA | TTT | AGA | GTA | 1077 |
| Ser | Ile | Met | Asn | Glu | His | Leu | Asn | Lys | Glu | Lys | Glu | Glu | Phe | Arg | Val | |
| | 1095 | | | | | 1100 | | | | | 1105 | | | | | |
| AAC | ATC | CTC | CCT | ACA | CTT | TCT | AAT | ACT | TTT | TCT | AAT | CCT | AAT | TAT | GCA | 1125 |
| Asn | Ile | Leu | Pro | Thr | Leu | Ser | Asn | Thr | Phe | Ser | Asn | Pro | Asn | Tyr | Ala | |
| 1110 | | | | | 1115 | | | | | 1120 | | | | | 1125 | |
| AAA | GTT | AAA | GGA | AGT | GAT | GAA | GAT | GCA | AAG | ATG | ATT | GTG | GAA | GCT | AAA | 1173 |
| Lys | Val | Lys | Gly | Ser | Asp | Glu | Asp | Ala | Lys | Met | Ile | Val | Glu | Ala | Lys | |
| | | | | 1130 | | | | 1135 | | | | | 1140 | | | |
| CCA | GGA | CAT | GCA | TTG | ATT | GGG | TTT | GAA | ATT | AGT | AAT | GAT | TCA | ATT | ACA | 1221 |
| Pro | Gly | His | Ala | Leu | Ile | Gly | Phe | Glu | Ile | Ser | Asn | Asp | Ser | Ile | Thr | |
| | | | 1145 | | | | 1150 | | | | | 1155 | | | | |
| GTA | TTA | AAA | GTA | TAT | GAG | GCT | AAG | CTA | AAA | CAA | AAT | TAT | CAA | GTC | GAT | 1269 |
| Val | Leu | Lys | Val | Tyr | Glu | Ala | Lys | Leu | Lys | Gln | Asn | Tyr | Gln | Val | Asp | |
| | | 1160 | | | | | 1165 | | | | | 1170 | | | | |
| AAG | GAT | TCC | TTA | TCG | GAA | GTT | ATT | TAT | GGC | GAT | ATG | GAT | AAA | TTA | TTG | 1317 |
| Lys | Asp | Ser | Leu | Ser | Glu | Val | Ile | Tyr | Gly | Asp | Met | Asp | Lys | Leu | Leu | |
| | 1175 | | | | | 1180 | | | | | 1185 | | | | | |
| TGC | CCA | GAT | CAA | TCT | GGA | CAA | ATC | TAT | TAT | ACA | AAT | AAC | ATA | GTA | TTT | 1365 |
| Cys | Pro | Asp | Gln | Ser | Gly | Gln | Ile | Tyr | Tyr | Thr | Asn | Asn | Ile | Val | Phe | |
| 1190 | | | | | 1195 | | | | | 1200 | | | | | 1205 | |
| CCA | AAT | GAA | TAT | GTA | ATT | ACT | AAA | ATT | GAT | TTC | ACT | AAA | AAA | ATG | AAA | 1413 |
| Pro | Asn | Glu | Tyr | Val | Ile | Thr | Lys | Ile | Asp | Phe | Thr | Lys | Lys | Met | Lys | |
| | | | | 1210 | | | | 1215 | | | | | 1220 | | | |
| ACT | TTA | AGA | TAT | GAG | GTA | ACA | GCG | AAT | TTT | TAT | GAT | TCT | TCT | ACA | GGA | 1461 |
| Thr | Leu | Arg | Tyr | Glu | Val | Thr | Ala | Asn | Phe | Tyr | Asp | Ser | Ser | Thr | Gly | |
| | | | 1225 | | | | 1230 | | | | | 1235 | | | | |
| GAA | ATT | GAC | TTA | AAT | AAG | AAA | AAA | GTA | GAA | TCA | AGT | GAA | GCG | GAG | TAT | 1509 |
| Glu | Ile | Asp | Leu | Asn | Lys | Lys | Lys | Val | Glu | Ser | Ser | Glu | Ala | Glu | Tyr | |
| | | 1240 | | | | | 1245 | | | | | 1250 | | | | |
| AGA | ACG | TTA | AGT | GCT | AAT | GAT | GAT | GGG | GTG | TAT | ATG | CCG | TTA | GGT | GTC | 1557 |
| Arg | Thr | Leu | Ser | Ala | Asn | Asp | Asp | Gly | Val | Tyr | Met | Pro | Leu | Gly | Val | |
| | 1255 | | | | | 1260 | | | | | 1265 | | | | | |
| ATC | AGT | GAA | ACA | TTT | TTG | ACT | CCG | ATT | AAT | GGG | TTT | GGC | CTC | CAA | GCT | 1605 |
| Ile | Ser | Glu | Thr | Phe | Leu | Thr | Pro | Ile | Asn | Gly | Phe | Gly | Leu | Gln | Ala | |
| 1270 | | | | | 1275 | | | | | 1280 | | | | | 1285 | |
| GAT | GAA | AAT | TCA | AGA | TTA | ATT | ACT | TTA | ACA | TGT | AAA | TCA | TAT | TTA | AGA | 1653 |
| Asp | Glu | Asn | Ser | Arg | Leu | Ile | Thr | Leu | Thr | Cys | Lys | Ser | Tyr | Leu | Arg | |
| | | | | 1290 | | | | 1295 | | | | | 1300 | | | |
| GAA | CTA | CTG | CTA | GCA | ACA | GAC | TTA | AGC | AAT | AAA | GAA | ACT | AAA | TTG | ATC | 1701 |
| Glu | Leu | Leu | Leu | Ala | Thr | Asp | Leu | Ser | Asn | Lys | Glu | Thr | Lys | Leu | Ile | |
| | | | 1305 | | | | 1310 | | | | | 1315 | | | | |
| GTC | CCG | CCA | AGT | GGT | TTT | ATT | AGC | AAT | ATT | GTA | GAG | AAC | GGG | TCC | ATA | 1749 |
| Val | Pro | Pro | Ser | Gly | Phe | Ile | Ser | Asn | Ile | Val | Glu | Asn | Gly | Ser | Ile | |
| | | 1320 | | | | | 1325 | | | | | 1330 | | | | |
| GAA | GAG | GAC | AAT | TTA | GAG | CCG | TGG | AAA | GCA | AAT | AAT | AAG | AAT | GCG | TAT | 1797 |
| Glu | Glu | Asp | Asn | Leu | Glu | Pro | Trp | Lys | Ala | Asn | Asn | Lys | Asn | Ala | Tyr | |
| | 1335 | | | | | 1340 | | | | | 1345 | | | | | |
| GTA | GAT | CAT | ACA | GGC | GGA | GTG | AAT | GGA | ACT | AAA | GCT | TTA | TAT | GTT | CAT | 1845 |
| Val | Asp | His | Thr | Gly | Gly | Val | Asn | Gly | Thr | Lys | Ala | Leu | Tyr | Val | His | |
| 1350 | | | | | 1355 | | | | | 1360 | | | | | 1365 | |

| | | | | | | | | | | | | | | | | |
|---|---|---|---|---|---|---|---|---|---|---|---|---|---|---|---|---|
| AAG | GAC | GGA | GGA | ATT | TCA | CAA | TTT | ATT | GGA | GAT | AAG | TTA | AAA | CCG | AAA | 1893 |
| Lys | Asp | Gly | Gly | Ile | Ser | Gln | Phe | Ile | Gly | Asp | Lys | Leu | Lys | Pro | Lys | |
| | | | | 1370 | | | | 1375 | | | | | | 1380 | | |
| ACT | GAG | TAT | GTA | ATC | CAA | TAT | ACT | GTT | AAA | GGA | AAA | CCT | TCT | ATT | CAT | 1941 |
| Thr | Glu | Tyr | Val | Ile | Gln | Tyr | Thr | Val | Lys | Gly | Lys | Pro | Ser | Ile | His | |
| | | | 1385 | | | | | 1390 | | | | | 1395 | | | |
| TTA | AAA | GAT | GAA | AAT | ACT | GGA | TAT | ATT | CAT | TAT | GAA | GAT | ACA | AAT | AAT | 1989 |
| Leu | Lys | Asp | Glu | Asn | Thr | Gly | Tyr | Ile | His | Tyr | Glu | Asp | Thr | Asn | Asn | |
| | | 1400 | | | | | 1405 | | | | | 1410 | | | | |
| AAT | TTA | GAA | GAT | TAT | CAA | ACT | ATT | AAT | AAA | CGT | TTT | ACT | ACA | GGA | ACT | 2037 |
| Asn | Leu | Glu | Asp | Tyr | Gln | Thr | Ile | Asn | Lys | Arg | Phe | Thr | Thr | Gly | Thr | |
| | 1415 | | | | | 1420 | | | | | 1425 | | | | | |
| GAT | TTA | AAG | GGA | GTG | TAT | TTA | ATT | TTA | AAA | AGT | CAA | AAT | GGA | GAT | GAA | 2085 |
| Asp | Leu | Lys | Gly | Val | Tyr | Leu | Ile | Leu | Lys | Ser | Gln | Asn | Gly | Asp | Glu | |
| 1430 | | | | 1435 | | | | | 1440 | | | | | | 1445 | |
| GCT | TGG | GGA | GAT | AAC | TTT | ATT | ATT | TTG | GAA | ATT | AGT | CCT | TCT | GAA | AAG | 2133 |
| Ala | Trp | Gly | Asp | Asn | Phe | Ile | Ile | Leu | Glu | Ile | Ser | Pro | Ser | Glu | Lys | |
| | | | | 1450 | | | | | 1455 | | | | | 1460 | | |
| TTA | TTA | AGT | CCA | GAA | TTA | ATT | AAT | ACA | AAT | AAT | TGG | ACG | AGT | ACG | GGA | 2181 |
| Leu | Leu | Ser | Pro | Glu | Leu | Ile | Asn | Thr | Asn | Asn | Trp | Thr | Ser | Thr | Gly | |
| | | | 1465 | | | | | 1470 | | | | | 1475 | | | |
| TCA | ACT | AAT | ATT | AGC | GGT | AAT | ACA | CTC | ACT | CTT | TAT | CAG | GGA | GGA | CGA | 2229 |
| Ser | Thr | Asn | Ile | Ser | Gly | Asn | Thr | Leu | Thr | Leu | Tyr | Gln | Gly | Gly | Arg | |
| | | | 1480 | | | | | 1485 | | | | | 1490 | | | |
| GGG | ATT | CTA | AAA | CAA | AAC | CTT | CAA | TTA | GAT | AGT | TTT | TCA | ACT | TAT | AGA | 2277 |
| Gly | Ile | Leu | Lys | Gln | Asn | Leu | Gln | Leu | Asp | Ser | Phe | Ser | Thr | Tyr | Arg | |
| | 1495 | | | | | 1500 | | | | | 1505 | | | | | |
| GTG | TAT | TTC | TCT | GTG | TCC | GGA | GAT | GCT | AAT | GTA | AGG | ATT | AGA | AAT | TCT | 2325 |
| Val | Tyr | Phe | Ser | Val | Ser | Gly | Asp | Ala | Asn | Val | Arg | Ile | Arg | Asn | Ser | |
| 1510 | | | | | 1515 | | | | | 1520 | | | | | 1525 | |
| AGG | GAA | GTG | TTA | TTT | GAA | AAA | AGA | TAT | ATG | AGC | GGT | GCT | AAA | GAT | GTT | 2373 |
| Arg | Glu | Val | Leu | Phe | Glu | Lys | Arg | Tyr | Met | Ser | Gly | Ala | Lys | Asp | Val | |
| | | | | 1530 | | | | | 1535 | | | | | 1540 | | |
| TCT | GAA | ATG | TTC | ACT | ACA | AAA | TTT | GAG | AAA | GAT | AAC | TTC | TAT | ATA | GAG | 2421 |
| Ser | Glu | Met | Phe | Thr | Thr | Lys | Phe | Glu | Lys | Asp | Asn | Phe | Tyr | Ile | Glu | |
| | | | 1545 | | | | | 1550 | | | | | 1555 | | | |
| CTT | TCT | CAA | GGG | AAT | AAT | TTA | TAT | GGT | GGT | CCT | ATT | GTA | CAT | TTT | TAC | 2469 |
| Leu | Ser | Gln | Gly | Asn | Asn | Leu | Tyr | Gly | Gly | Pro | Ile | Val | His | Phe | Tyr | |
| | | 1560 | | | | | 1565 | | | | | 1570 | | | | |
| GAT | GTC | TCT | ATT | AAG | TAAGATCGGG | ATCTAATATT | AACAGTTTTT | AGAAGCTAAT | 2524 |
| Asp | Val | Ser | Ile | Lys | | | | | |
| | 1575 | | | | | | | | |

TCTTGTATAA TGTCCTTGAT TATGGAAAAA CACAATTTTG TTTGCTAAGA TGTATATATA 2584

GCTCACTCAT TAAAAGGCAA TCAAGCTT 2612

( 2 ) INFORMATION FOR SEQ ID NO:4:

( i ) SEQUENCE CHARACTERISTICS:
        ( A ) LENGTH: 789 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Asn | Lys | Asn | Asn | Thr | Lys | Leu | Ser | Thr | Arg | Ala | Leu | Pro | Ser | Phe |
| 1 | | | | 5 | | | | | 10 | | | | | 15 | |
| Ile | Asp | Tyr | Phe | Asn | Gly | Ile | Tyr | Gly | Phe | Ala | Thr | Gly | Ile | Lys | Asp |
| | | | 20 | | | | | 25 | | | | | 30 | | |
| Ile | Met | Asn | Met | Ile | Phe | Lys | Thr | Asp | Thr | Gly | Gly | Asp | Leu | Thr | Leu |
| | | 35 | | | | | 40 | | | | | 45 | | | |

Asp Glu Ile Leu Lys Asn Gln Gln Leu Leu Asn Asp Ile Ser Gly Lys
          50                      55                      60

Leu Asp Gly Val Asn Gly Ser Leu Asn Asp Leu Ile Ala Gln Gly Asn
 65              70                      75                      80

Leu Asn Thr Glu Leu Ser Lys Glu Ile Leu Lys Ile Ala Asn Glu Gln
                 85                      90                      95

Asn Gln Val Leu Asn Asp Val Asn Asn Lys Leu Asp Ala Ile Asn Thr
            100                     105                     110

Met Leu Arg Val Tyr Leu Pro Lys Ile Thr Ser Met Leu Ser Asp Val
            115                     120                     125

Met Lys Gln Asn Tyr Ala Leu Ser Leu Gln Ile Glu Tyr Leu Ser Lys
    130                     135                     140

Gln Leu Gln Glu Ile Ser Asp Lys Leu Asp Ile Ile Asn Val Asn Val
145                     150                     155                     160

Leu Ile Asn Ser Thr Leu Thr Glu Ile Thr Pro Ala Tyr Gln Arg Ile
                165                     170                     175

Lys Tyr Val Asn Glu Lys Phe Glu Glu Leu Thr Phe Ala Thr Glu Thr
            180                     185                     190

Ser Ser Lys Val Lys Lys Asp Gly Ser Pro Ala Asp Ile Arg Asp Glu
        195                     200                     205

Leu Thr Glu Leu Thr Glu Leu Ala Lys Ser Val Thr Lys Asn Asp Val
    210                     215                     220

Asp Gly Phe Glu Phe Tyr Leu Asn Thr Phe His Asp Val Met Val Gly
225                     230                     235                     240

Asn Asn Leu Phe Gly Arg Ser Ala Leu Lys Thr Ala Ser Glu Leu Ile
                245                     250                     255

Thr Lys Glu Asn Val Lys Thr Ser Gly Ser Glu Val Gly Asn Val Tyr
            260                     265                     270

Asn Phe Leu Ile Val Leu Thr Ala Leu Gln Ala Lys Ala Phe Leu Thr
            275                     280                     285

Leu Thr Pro Cys Arg Lys Leu Leu Gly Leu Ala Asp Ile Asp Tyr Thr
    290                     295                     300

Ser Ile Met Asn Glu His Leu Asn Lys Glu Lys Glu Glu Phe Arg Val
305                     310                     315                     320

Asn Ile Leu Pro Thr Leu Ser Asn Thr Phe Ser Asn Pro Asn Tyr Ala
                325                     330                     335

Lys Val Lys Gly Ser Asp Glu Asp Ala Lys Met Ile Val Glu Ala Lys
            340                     345                     350

Pro Gly His Ala Leu Ile Gly Phe Glu Ile Ser Asn Asp Ser Ile Thr
        355                     360                     365

Val Leu Lys Val Tyr Glu Ala Lys Leu Lys Gln Asn Tyr Gln Val Asp
    370                     375                     380

Lys Asp Ser Leu Ser Glu Val Ile Tyr Gly Asp Met Asp Lys Leu Leu
385                     390                     395                     400

Cys Pro Asp Gln Ser Gly Gln Ile Tyr Tyr Thr Asn Asn Ile Val Phe
                405                     410                     415

Pro Asn Glu Tyr Val Ile Thr Lys Ile Asp Phe Thr Lys Lys Met Lys
            420                     425                     430

Thr Leu Arg Tyr Glu Val Thr Ala Asn Phe Tyr Asp Ser Ser Thr Gly
        435                     440                     445

Glu Ile Asp Leu Asn Lys Lys Lys Val Glu Ser Ser Glu Ala Glu Tyr
    450                     455                     460

Arg Thr Leu Ser Ala Asn Asp Asp Gly Val Tyr Met Pro Leu Gly Val

|       |       |       |       | 465   |       |       |       |       | 470   |       |       |       |       | 475   |       |       |       |       | 480   |
|-------|-------|-------|-------|-------|-------|-------|-------|-------|-------|-------|-------|-------|-------|-------|-------|-------|-------|-------|-------|

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Ser Ile
530                 535                 540

Glu Glu Asp Asn Leu Glu Pro Trp Lys Ala Asn Asn Lys Asn Ala Tyr
545                 550                 555                 560

Val Asp His Thr Gly Gly Val Asn Gly Thr Lys Ala Leu Tyr Val His
                565                 570                 575

Lys Asp Gly Gly Ile Ser Gln Phe Ile Gly Asp Lys Leu Lys Pro Lys
            580                 585                 590

Thr Glu Tyr Val Ile Gln Tyr Thr Val Lys Gly Lys Pro Ser Ile His
            595                 600                 605

Leu Lys Asp Glu Asn Thr Gly Tyr Ile His Tyr Glu Asp Thr Asn Asn
    610                 615                 620

Asn Leu Glu Asp Tyr Gln Thr Ile Asn Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Ile Ile Leu Glu Ile Ser Pro Ser Glu Lys
            660                 665                 670

Leu Leu Ser Pro Glu Leu Ile Asn Thr Asn Asn Trp Thr Ser Thr Gly
        675                 680                 685

Ser Thr Asn Ile Ser Gly Asn Thr Leu Thr Leu Tyr Gln Gly Gly Arg
    690                 695                 700

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
                725                 730                 735

Arg Glu Val Leu Phe Glu Lys Arg Tyr Met Ser Gly Ala Lys Asp Val
            740                 745                 750

Ser Glu Met Phe Thr Thr Lys Phe Glu Lys Asp Asn Phe Tyr Ile Glu
        755                 760                 765

Leu Ser Gln Gly Asn Asn Leu Tyr Gly Gly Pro Ile Val His Phe Tyr
    770                 775                 780

Asp Val Ser Ile Lys
785

(2) INFORMATION FOR SEQ ID NO:5:

(i) SEQUENCE CHARACTERISTICS:
        (A) LENGTH: 2364 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 56..2292
        (D) OTHER INFORMATION: /product="VIP3A(c) protein"

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| AATACAATTT | | ACGAGGGATA | | AGTGTTACAA | | AGAATAGCTG | | AGGAGGGAGA | | TGAAC | ATG Met 1 | | | | | 58 |

| AAC | AAG | AAT | AAT | GCT | AAA | TTA | AGC | ACA | AGA | GCC | TTA | CCA | AGT | TTT | ATT | 106 |
|---|---|---|---|---|---|---|---|---|---|---|---|---|---|---|---|---|
| Asn | Lys | Asn | Asn 5 | Ala | Lys | Leu | Ser | Thr 10 | Arg | Ala | Leu | Pro | Ser 15 | Phe | Ile | |

| GAT | TAT | TTC | AAT | GGC | ATT | TAT | GGA | TTT | GCC | ACT | GGT | ATC | AAA | GAC | ATT | 154 |
|---|---|---|---|---|---|---|---|---|---|---|---|---|---|---|---|---|
| Asp | Tyr | Phe 20 | Asn | Gly | Ile | Tyr | Gly 25 | Phe | Ala | Thr | Gly | Ile 30 | Lys | Asp | Ile | |

| ATG | AAC | ATG | ATT | TTT | AAA | ACG | GAT | ACA | GGT | GGT | GAT | CTA | GCC | CTA | GAC | 202 |
|---|---|---|---|---|---|---|---|---|---|---|---|---|---|---|---|---|
| Met | Asn 35 | Met | Ile | Phe | Lys | Thr 40 | Asp | Thr | Gly | Gly | Asp 45 | Leu | Ala | Leu | Asp | |

| GAA | ATT | TTA | GAG | AAT | CAG | CAG | CTA | CTA | AAT | GAT | ATT | TCT | GGT | AAA | TTG | 250 |
|---|---|---|---|---|---|---|---|---|---|---|---|---|---|---|---|---|
| Glu 50 | Ile | Leu | Glu | Asn | Gln 55 | Gln | Leu | Leu | Asn | Asp 60 | Ile | Ser | Gly | Lys | Leu 65 | |

| GAT | GGG | GTG | AAT | GGA | AGC | TTA | AAT | GAT | CTT | ATC | GCA | CAG | GGA | AAC | TTA | 298 |
|---|---|---|---|---|---|---|---|---|---|---|---|---|---|---|---|---|
| Asp | Gly | Val | Asn | Gly 70 | Ser | Leu | Asn | Asp | Leu 75 | Ile | Ala | Gln | Gly | Asn 80 | Leu | |

| AAT | ACA | GAA | TTA | TCT | AAG | GAA | ATA | TTA | AAA | ATT | GCA | AAT | GAA | CAA | AAT | 346 |
|---|---|---|---|---|---|---|---|---|---|---|---|---|---|---|---|---|
| Asn | Thr | Glu | Leu 85 | Ser | Lys | Glu | Ile | Leu 90 | Lys | Ile | Ala | Asn | Glu 95 | Gln | Asn | |

| CAA | GTT | TTA | AAT | GAT | GTT | AAT | AAC | AAA | CTC | GAT | GCG | ATA | AAT | ACG | ATG | 394 |
|---|---|---|---|---|---|---|---|---|---|---|---|---|---|---|---|---|
| Gln | Val | Leu 100 | Asn | Asp | Val | Asn | Asn 105 | Lys | Leu | Asp | Ala | Ile 110 | Asn | Thr | Met | |

| CTT | CGG | GTA | TAT | CTA | CCT | AAA | ATT | ACC | TCT | ATG | TTG | AGT | GAT | GTA | ATG | 442 |
|---|---|---|---|---|---|---|---|---|---|---|---|---|---|---|---|---|
| Leu | Arg 115 | Val | Tyr | Leu | Pro | Lys 120 | Ile | Thr | Ser | Met | Leu 125 | Ser | Asp | Val | Met | |

| AAA | CAA | AAT | TAT | GCG | CTA | AGT | CTG | CAA | ATA | GAA | TAC | TTA | AGT | AAA | CAA | 490 |
|---|---|---|---|---|---|---|---|---|---|---|---|---|---|---|---|---|
| Lys 130 | Gln | Asn | Tyr | Ala | Leu 135 | Ser | Leu | Gln | Ile | Glu 140 | Tyr | Leu | Ser | Lys | Gln 145 | |

| TTG | CAA | GAG | ATT | TCT | GAT | AAG | TTG | GAT | ATT | ATT | AAT | GTA | AAT | GTA | CTT | 538 |
|---|---|---|---|---|---|---|---|---|---|---|---|---|---|---|---|---|
| Leu | Gln | Glu | Ile | Ser 150 | Asp | Lys | Leu | Asp | Ile 155 | Ile | Asn | Val | Asn | Val 160 | Leu | |

| ATT | AAC | TCT | ACA | CTT | ACT | GAA | ATT | ACA | CCT | GCG | TAT | CAA | AGG | ATT | AAA | 586 |
|---|---|---|---|---|---|---|---|---|---|---|---|---|---|---|---|---|
| Ile | Asn | Ser | Thr 165 | Leu | Thr | Glu | Ile | Thr 170 | Pro | Ala | Tyr | Gln | Arg 175 | Ile | Lys | |

| TAT | GTG | AAC | GAA | AAA | TTT | GAG | GAA | TTA | ACT | TTT | GCT | ACA | GAA | ACT | AGT | 634 |
|---|---|---|---|---|---|---|---|---|---|---|---|---|---|---|---|---|
| Tyr | Val | Asn 180 | Glu | Lys | Phe | Glu | Glu 185 | Leu | Thr | Phe | Ala | Thr 190 | Glu | Thr | Ser | |

| TCA | AAA | GTA | AAA | AAG | GAT | GGC | TCT | CCT | GCA | GAT | ATT | CGT | GAT | GAG | TTA | 682 |
|---|---|---|---|---|---|---|---|---|---|---|---|---|---|---|---|---|
| Ser | Lys 195 | Val | Lys | Lys | Asp | Gly 200 | Ser | Pro | Ala | Asp | Ile 205 | Arg | Asp | Glu | Leu | |

| AGT | GAG | TTA | ACT | GAA | CTA | GCG | AAA | AGT | GTA | ACA | CAA | AAT | GAT | GTG | GAT | 730 |
|---|---|---|---|---|---|---|---|---|---|---|---|---|---|---|---|---|
| Ser 210 | Glu | Leu | Thr | Glu | Leu 215 | Ala | Lys | Ser | Val | Thr 220 | Gln | Asn | Asp | Val | Asp 225 | |

| GGT | TTT | GAA | TTT | TAC | CTT | AAT | ACA | TTC | CAC | GAT | GTA | ATG | GTA | GGA | AAT | 778 |
|---|---|---|---|---|---|---|---|---|---|---|---|---|---|---|---|---|
| Gly | Phe | Glu | Phe | Tyr 230 | Leu | Asn | Thr | Phe | His 235 | Asp | Val | Met | Val | Gly 240 | Asn | |

| AAT | TTA | TTC | GGG | CGT | TCA | GCT | TTA | AAA | ACT | GCA | TCG | GAA | TTA | ATT | ACT | 826 |
|---|---|---|---|---|---|---|---|---|---|---|---|---|---|---|---|---|
| Asn | Leu | Phe | Gly 245 | Arg | Ser | Ala | Leu | Lys 250 | Thr | Ala | Ser | Glu | Leu 255 | Ile | Thr | |

| AAA | GAA | AAT | GTG | AAA | ACA | AGT | GGC | AGT | GAG | GTC | GGA | AAT | GTT | TAT | AAC | 874 |
|---|---|---|---|---|---|---|---|---|---|---|---|---|---|---|---|---|
| Lys | Glu | Asn 260 | Val | Lys | Thr | Ser | Gly 265 | Ser | Glu | Val | Gly | Asn 270 | Val | Tyr | Asn | |

| TTC | CTA | ATT | GTA | TTA | ACA | GCT | CTG | CAA | GCA | CAA | GCT | TTT | CTT | ACT | TTA | 922 |
|---|---|---|---|---|---|---|---|---|---|---|---|---|---|---|---|---|
| Phe | Leu 275 | Ile | Val | Leu | Thr | Ala 280 | Leu | Gln | Ala | Gln | Ala 285 | Phe | Leu | Thr | Leu | |

| ACA | CCA | TGC | CGA | AAA | TTA | TTA | GGC | TTA | GCA | GAT | ATT | GAT | TAT | ACT | TCT | 970 |
|---|---|---|---|---|---|---|---|---|---|---|---|---|---|---|---|---|
| Thr | Pro | Cys | Arg | Lys | Leu | Leu | Gly | Leu | Ala | Asp | Ile | Asp | Tyr | Thr | Ser | |

```
                   290                          295                           300                          305

ATT ATG AAT GAA CAT TTA AAT AAG GAA AAA GAG GAA TTT AGA GTA AAC       1018
Ile Met Asn Glu His Leu Asn Lys Glu Lys Glu Glu Phe Arg Val Asn
                    310                 315                     320

ATC CTC CCT ACA CTT TCT AAT ACT TTT TCT AAT CCT AAT TAT GCA AAA       1066
Ile Leu Pro Thr Leu Ser Asn Thr Phe Ser Asn Pro Asn Tyr Ala Lys
            325                 330                 335

GTT AAA GGA AGT GAT GAA GAT GCA AAG ATG ATT GTG GAA GCT AAA CCA       1114
Val Lys Gly Ser Asp Glu Asp Ala Lys Met Ile Val Glu Ala Lys Pro
                340                 345                 350

GGA CAT GCA TTG ATT GGG TTT GAA ATT AGT AAT GAT TCA ATT ACA GTA       1162
Gly His Ala Leu Ile Gly Phe Glu Ile Ser Asn Asp Ser Ile Thr Val
        355                 360                 365

TTA AAA GTA TAT GAG GCT AAG CTA AAA CAA AAT TAT CAA GTC GAT AAG       1210
Leu Lys Val Tyr Glu Ala Lys Leu Lys Gln Asn Tyr Gln Val Asp Lys
370                 375                 380                 385

GAT TCC TTA TCG GAA GTT ATT TAT GGC GAT ATG GAT AAA TTA TTG TGC       1258
Asp Ser Leu Ser Glu Val Ile Tyr Gly Asp Met Asp Lys Leu Leu Cys
                    390                 395                 400

CCA GAT CAA TCT GGA CAA ATC TAT TAT ACA AAT AAC ATA GTA TTT CCA       1306
Pro Asp Gln Ser Gly Gln Ile Tyr Tyr Thr Asn Asn Ile Val Phe Pro
                405                 410                 415

AAT GAA TAT GTA ATT ACT AAA ATT GAT TTC ACT AAA AAA ATG AAA ACT       1354
Asn Glu Tyr Val Ile Thr Lys Ile Asp Phe Thr Lys Lys Met Lys Thr
            420                 425                 430

TTA AGA TAT GAG GTA ACA GCG AAT TTT TAT GAT TCT TCT ACA GGA GAA       1402
Leu Arg Tyr Glu Val Thr Ala Asn Phe Tyr Asp Ser Ser Thr Gly Glu
        435                 440                 445

ATT GAC TTA AAT AAG AAA AAA GTA GAA TCA AGT GAA GCG GAG TAT AGA       1450
Ile Asp Leu Asn Lys Lys Lys Val Glu Ser Ser Glu Ala Glu Tyr Arg
450                 455                 460                 465

ACG TTA AGT GCT AAT GAT GAT GGG GTG TAT ATG CCG TTA GGT GTC ATC       1498
Thr Leu Ser Ala Asn Asp Asp Gly Val Tyr Met Pro Leu Gly Val Ile
                    470                 475                 480

AGT GAA ACA TTT TTG ACT CCG ATT AAT GGG TTT GGC CTC CAA GCT GAT       1546
Ser Glu Thr Phe Leu Thr Pro Ile Asn Gly Phe Gly Leu Gln Ala Asp
                485                 490                 495

GAA AAT TCA AGA TTA ATT ACT TTA ACA TGT AAA TCA TAT TTA AGA GAA       1594
Glu Asn Ser Arg Leu Ile Thr Leu Thr Cys Lys Ser Tyr Leu Arg Glu
            500                 505                 510

CTA CTG CTA GCA ACA GAC TTA AGC AAT AAA GAA ACT AAA TTG ATC GTC       1642
Leu Leu Leu Ala Thr Asp Leu Ser Asn Lys Glu Thr Lys Leu Ile Val
        515                 520                 525

CCG CCA AGT GGT TTT ATT AGC AAT ATT GTA GAG AAC GGG TCC ATA GAA       1690
Pro Pro Ser Gly Phe Ile Ser Asn Ile Val Glu Asn Gly Ser Ile Glu
530                 535                 540                 545

GAG GAC AAT TTA GAG CCG TGG AAA GCA AAT AAT AAG AAT GCG TAT GTA       1738
Glu Asp Asn Leu Glu Pro Trp Lys Ala Asn Asn Lys Asn Ala Tyr Val
                    550                 555                 560

GAT CAT ACA GGC GGA GTG AAT GGA ACT AAA GCT TTA TAT GTT CAT AAG       1786
Asp His Thr Gly Gly Val Asn Gly Thr Lys Ala Leu Tyr Val His Lys
                565                 570                 575

GAC GGA GGA ATT TCA CAA TTT ATT GGA GAT AAG TTA AAA CCG AAA ACT       1834
Asp Gly Gly Ile Ser Gln Phe Ile Gly Asp Lys Leu Lys Pro Lys Thr
            580                 585                 590

GAG TAT GTA ATC CAA TAT ACT GTT AAA GGA AAA CCT TCT ATT CAT TTA       1882
Glu Tyr Val Ile Gln Tyr Thr Val Lys Gly Lys Pro Ser Ile His Leu
        595                 600                 605

AAA GAT GAA AAT ACT GGA TAT ATT CAT TAT GAA GAT ACA AAT AAT AAT       1930
Lys Asp Glu Asn Thr Gly Tyr Ile His Tyr Glu Asp Thr Asn Asn Asn
```

```
610                         615                          620                          625
TTA  GAA  GAT  TAT  CAA  ACT  ATT  AAT  AAA  CGT  TTT  ACT  ACA  GGA  ACT  GAT      1978
Leu  Glu  Asp  Tyr  Gln  Thr  Ile  Asn  Lys  Arg  Phe  Thr  Thr  Gly  Thr  Asp
                    630                      635                          640

TTA  AAG  GGA  GTG  TAT  TTA  ATT  TTA  AAA  AGT  CAA  AAT  GGA  GAT  GAA  GCT      2026
Leu  Lys  Gly  Val  Tyr  Leu  Ile  Leu  Lys  Ser  Gln  Asn  Gly  Asp  Glu  Ala
               645                      650                          655

TGG  GGA  GAT  AAC  TTT  ATT  ATT  TTG  GAA  ATT  AGT  CCT  TCT  GAA  AAG  TTA      2074
Trp  Gly  Asp  Asn  Phe  Ile  Ile  Leu  Glu  Ile  Ser  Pro  Ser  Glu  Lys  Leu
               660                      665                     670

TTA  AGT  CCA  GAA  TTA  ATT  AAT  ACA  AAT  AAT  TGG  ACG  AGT  ACG  GGA  TCA      2122
Leu  Ser  Pro  Glu  Leu  Ile  Asn  Thr  Asn  Asn  Trp  Thr  Ser  Thr  Gly  Ser
          675                      680                          685

ACT  AAT  ATT  AGC  GGT  AAT  ACA  CTC  ACT  CTT  TAT  CAG  GGA  GGA  CGA  GGG      2170
Thr  Asn  Ile  Ser  Gly  Asn  Thr  Leu  Thr  Leu  Tyr  Gln  Gly  Gly  Arg  Gly
690                      695                          700                     705

ATT  CTA  AAA  CAA  AAC  CTT  CAA  TTA  GAT  AGT  TTT  TCA  ACT  TAT  AGA  GTG      2218
Ile  Leu  Lys  Gln  Asn  Leu  Gln  Leu  Asp  Ser  Phe  Ser  Thr  Tyr  Arg  Val
                    710                      715                          720

TAT  TTC  TCT  GTG  TCC  GGA  GAT  GCT  AAT  GTA  AGG  ATT  AGA  AAT  TCT  AGG      2266
Tyr  Phe  Ser  Val  Ser  Gly  Asp  Ala  Asn  Val  Arg  Ile  Arg  Asn  Ser  Arg
               725                      730                          735

GAA  GTG  TTA  TTT  GAA  AAA  AAG  GAT  ATA  TGA  GC  GGCGCTAAAG  ATGTTTCTGA         2318
Glu  Val  Leu  Phe  Glu  Lys  Lys  Asp  Ile
               740                      745

AATGTTCACT  ACAAAATTGA  AAGATAACTT  CTATATAGAG  CTTTCT                               2364
```

( 2 ) INFORMATION FOR SEQ ID NO:6:

( i ) SEQUENCE CHARACTERISTICS:
        ( A ) LENGTH: 746 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Asn  Lys  Asn  Asn  Ala  Lys  Leu  Ser  Thr  Arg  Ala  Leu  Pro  Ser  Phe
1                   5                        10                         15

Ile  Asp  Tyr  Phe  Asn  Gly  Ile  Tyr  Gly  Phe  Ala  Thr  Gly  Ile  Lys  Asp
               20                       25                          30

Ile  Met  Asn  Met  Ile  Phe  Lys  Thr  Asp  Thr  Gly  Gly  Asp  Leu  Ala  Leu
          35                       40                          45

Asp  Glu  Ile  Leu  Glu  Asn  Gln  Gln  Leu  Leu  Asn  Asp  Ile  Ser  Gly  Lys
     50                       55                       60

Leu  Asp  Gly  Val  Asn  Gly  Ser  Leu  Asn  Asp  Leu  Ile  Ala  Gln  Gly  Asn
65                       70                       75                        80

Leu  Asn  Thr  Glu  Leu  Ser  Lys  Glu  Ile  Leu  Lys  Ile  Ala  Asn  Glu  Gln
                    85                       90                          95

Asn  Gln  Val  Leu  Asn  Asp  Val  Asn  Asn  Lys  Leu  Asp  Ala  Ile  Asn  Thr
               100                      105                         110

Met  Leu  Arg  Val  Tyr  Leu  Pro  Lys  Ile  Thr  Ser  Met  Leu  Ser  Asp  Val
          115                      120                         125

Met  Lys  Gln  Asn  Tyr  Ala  Leu  Ser  Leu  Gln  Ile  Glu  Tyr  Leu  Ser  Lys
     130                      135                       140

Gln  Leu  Gln  Glu  Ile  Ser  Asp  Lys  Leu  Asp  Ile  Ile  Asn  Val  Asn  Val
145                      150                      155                        160

Leu  Ile  Asn  Ser  Thr  Leu  Thr  Glu  Ile  Thr  Pro  Ala  Tyr  Gln  Arg  Ile
                    165                      170                         175
```

-continued

| | | | | | | | | | | | | | | |
|---|---|---|---|---|---|---|---|---|---|---|---|---|---|---|
| Lys | Tyr | Val | Asn 180 | Glu | Lys | Phe | Glu | Glu 185 | Leu | Thr | Phe | Ala | Thr 190 | Glu | Thr |
| Ser | Ser | Lys 195 | Val | Lys | Lys | Asp | Gly 200 | Ser | Pro | Ala | Asp | Ile 205 | Arg | Asp | Glu |
| Leu | Ser 210 | Glu | Leu | Thr | Glu | Leu 215 | Ala | Lys | Ser | Val | Thr 220 | Gln | Asn | Asp | Val |
| Asp 225 | Gly | Phe | Glu | Phe | Tyr 230 | Leu | Asn | Thr | Phe | His 235 | Asp | Val | Met | Val | Gly 240 |
| Asn | Asn | Leu | Phe | Gly 245 | Arg | Ser | Ala | Leu | Lys 250 | Thr | Ala | Ser | Glu | Leu 255 | Ile |
| Thr | Lys | Glu | Asn 260 | Val | Lys | Thr | Ser | Gly 265 | Ser | Glu | Val | Gly | Asn 270 | Val | Tyr |
| Asn | Phe | Leu 275 | Ile | Val | Leu | Thr | Ala 280 | Leu | Gln | Ala | Gln | Ala 285 | Phe | Leu | Thr |
| Leu | Thr 290 | Pro | Cys | Arg | Lys | Leu 295 | Leu | Gly | Leu | Ala | Asp 300 | Ile | Asp | Tyr | Thr |
| Ser 305 | Ile | Met | Asn | Glu | His 310 | Leu | Asn | Lys | Glu | Lys 315 | Glu | Glu | Phe | Arg | Val 320 |
| Asn | Ile | Leu | Pro | Thr 325 | Leu | Ser | Asn | Thr | Phe 330 | Ser | Asn | Pro | Asn | Tyr 335 | Ala |
| Lys | Val | Lys | Gly 340 | Ser | Asp | Glu | Asp | Ala 345 | Lys | Met | Ile | Val | Glu 350 | Ala | Lys |
| Pro | Gly | His 355 | Ala | Leu | Ile | Gly | Phe 360 | Glu | Ile | Ser | Asn | Asp 365 | Ser | Ile | Thr |
| Val | Leu 370 | Lys | Val | Tyr | Glu | Ala 375 | Lys | Leu | Lys | Gln | Asn 380 | Tyr | Gln | Val | Asp |
| Lys 385 | Asp | Ser | Leu | Ser | Glu 390 | Val | Ile | Tyr | Gly | Asp 395 | Met | Asp | Lys | Leu | Leu 400 |
| Cys | Pro | Asp | Gln | Ser 405 | Gly | Gln | Ile | Tyr | Tyr 410 | Thr | Asn | Asn | Ile | Val 415 | Phe |
| Pro | Asn | Glu | Tyr 420 | Val | Ile | Thr | Lys | Ile 425 | Asp | Phe | Thr | Lys | Lys 430 | Met | Lys |
| Thr | Leu | Arg 435 | Tyr | Glu | Val | Thr | Ala 440 | Asn | Phe | Tyr | Asp | Ser 445 | Ser | Thr | Gly |
| Glu | Ile 450 | Asp | Leu | Asn | Lys | Lys 455 | Lys | Val | Glu | Ser | Ser 460 | Glu | Ala | Glu | Tyr |
| Arg 465 | Thr | Leu | Ser | Ala | Asn 470 | Asp | Asp | Gly | Val | Tyr 475 | Met | Pro | Leu | Gly | Val 480 |
| Ile | Ser | Glu | Thr | Phe 485 | Leu | Thr | Pro | Ile | Asn 490 | Gly | Phe | Gly | Leu | Gln 495 | Ala |
| Asp | Glu | Asn | Ser 500 | Arg | Leu | Ile | Thr | Leu 505 | Thr | Cys | Lys | Ser | Tyr 510 | Leu | Arg |
| Glu | Leu | Leu 515 | Leu | Ala | Thr | Asp | Leu 520 | Ser | Asn | Lys | Glu | Thr 525 | Lys | Leu | Ile |
| Val | Pro | Pro 530 | Ser | Gly | Phe | Ile | Ser 535 | Asn | Ile | Val | Glu | Asn 540 | Gly | Ser | Ile |
| Glu 545 | Glu | Asp | Asn | Leu | Glu 550 | Pro | Trp | Lys | Ala | Asn 555 | Asn | Lys | Asn | Ala | Tyr 560 |
| Val | Asp | His | Thr | Gly 565 | Gly | Val | Asn | Gly | Thr 570 | Lys | Ala | Leu | Tyr | Val 575 | His |
| Lys | Asp | Gly | Gly 580 | Ile | Ser | Gln | Phe | Ile 585 | Gly | Asp | Lys | Leu | Lys 590 | Pro | Lys |
| Thr | Glu | Tyr | Val | Ile | Gln | Tyr | Thr | Val | Lys | Gly | Lys | Pro | Ser | Ile | His |

|     | 595 |     |     |     |     | 600 |     |     |     |     | 605 |     |     |     |
| --- | --- | --- | --- | --- | --- | --- | --- | --- | --- | --- | --- | --- | --- | --- |
| Leu | Lys | Asp | Glu | Asn | Thr | Gly | Tyr | Ile | His | Tyr | Glu | Asp | Thr | Asn | Asn |
|     | 610 |     |     |     |     | 615 |     |     |     |     | 620 |     |     |     |
| Asn | Leu | Glu | Asp | Tyr | Gln | Thr | Ile | Asn | Lys | Arg | Phe | Thr | Thr | Gly | Thr |
| 625 |     |     |     |     | 630 |     |     |     |     | 635 |     |     |     |     | 640 |
| Asp | Leu | Lys | Gly | Val | Tyr | Leu | Ile | Leu | Lys | Ser | Gln | Asn | Gly | Asp | Glu |
|     |     |     |     | 645 |     |     |     |     | 650 |     |     |     |     | 655 |     |
| Ala | Trp | Gly | Asp | Asn | Phe | Ile | Ile | Leu | Glu | Ile | Ser | Pro | Ser | Glu | Lys |
|     |     |     | 660 |     |     |     |     | 665 |     |     |     |     | 670 |     |     |
| Leu | Leu | Ser | Pro | Glu | Leu | Ile | Asn | Thr | Asn | Asn | Trp | Thr | Ser | Thr | Gly |
|     |     | 675 |     |     |     |     | 680 |     |     |     |     | 685 |     |     |     |
| Ser | Thr | Asn | Ile | Ser | Gly | Asn | Thr | Leu | Thr | Leu | Tyr | Gln | Gly | Gly | Arg |
|     | 690 |     |     |     |     | 695 |     |     |     |     | 700 |     |     |     |     |
| Gly | Ile | Leu | Lys | Gln | Asn | Leu | Gln | Leu | Asp | Ser | Phe | Ser | Thr | Tyr | Arg |
| 705 |     |     |     |     | 710 |     |     |     |     | 715 |     |     |     |     | 720 |
| Val | Tyr | Phe | Ser | Val | Ser | Gly | Asp | Ala | Asn | Val | Arg | Ile | Arg | Asn | Ser |
|     |     |     |     | 725 |     |     |     |     | 730 |     |     |     |     | 735 |     |
| Arg | Glu | Val | Leu | Phe | Glu | Lys | Lys | Asp | Ile |     |     |     |     |     |     |
|     |     |     | 740 |     |     |     |     | 745 |     |     |     |     |     |     |     |

( 2 ) INFORMATION FOR SEQ ID NO:7:

( i ) SEQUENCE CHARACTERISTICS:
        ( A ) LENGTH: 2403 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: misc_feature
        ( B ) LOCATION: 11..2389
        ( D ) OTHER INFORMATION: /note= "maize optimized DNA
                sequence encoding VIP3A(a)"

( x i ) SEQUENCE DESCRIPTION: SEQ ID NO:7:

| | | | | | |
|---|---|---|---|---|---|
| GGATCCACCA | ATGAACATGA | ACAAGAACAA | CACCAAGCTG | AGCACCCGCG | CCCTGCCGAG | 60 |
| CTTCATCGAC | TACTTCAACG | GCATCTACGG | CTTCGCCACC | GGCATCAAGG | ACATCATGAA | 120 |
| CATGATCTTC | AAGACCGACA | CCGGCGGCGA | CCTGACCCTG | GACGAGATCC | TGAAGAACCA | 180 |
| GCAGCTGCTG | AACGACATCA | GCGGCAAGCT | GGACGGCGTG | AACGGCAGCC | TGAACGACCT | 240 |
| GATCGCCCAG | GGCAACCTGA | ACACCGAGCT | GAGCAAGGAG | ATCCTTAAGA | TCGCCAACGA | 300 |
| GCAGAACCAG | GTGCTGAACG | ACGTGAACAA | CAAGCTGGAC | GCCATCAACA | CCATGCTGCG | 360 |
| CGTGTACCTG | CCGAAGATCA | CCAGCATGCT | GAGCGACGTG | ATGAAGCAGA | ACTACGCCCT | 420 |
| GAGCCTGCAG | ATCGAGTACC | TGAGCAAGCA | GCTGCAGGAG | ATCAGCGACA | AGCTGGACAT | 480 |
| CATCAACGTG | AACGTCCTGA | TCAACAGCAC | CCTGACCGAG | ATCACCCCGG | CCTACCAGCG | 540 |
| CATCAAGTAC | GTGAACGAGA | AGTTCGAAGA | GCTGACCTTC | GCCACCGAGA | CCAGCAGCAA | 600 |
| GGTGAAGAAG | GACGGCAGCC | CGGCCGACAT | CCTGGACGAG | CTGACCGAGC | TGACCGAGCT | 660 |
| GGCCAAGAGC | GTGACCAAGA | ACGACGTGGA | CGGCTTCGAG | TTCTACCTGA | ACACCTTCCA | 720 |
| CGACGTGATG | GTGGGCAACA | ACCTGTTCGG | CCGCAGCGCC | CTGAAGACCG | CCAGCGAGCT | 780 |
| GATCACCAAG | GAGAACGTGA | AGACCAGCGG | CAGCGAGGTG | GGCAACGTGT | ACAACTTCCT | 840 |
| GATCGTGCTG | ACCGCCCTGC | AGGCCCAGGC | CTTCCTGACC | CTGACCACCT | GTCGCAAGCT | 900 |

| | | | | | |
|---|---|---|---|---|---|
|GCTGGGCCTG|GCCGACATCG|ACTACACCAG|CATCATGAAC|GAGCACTTGA|ACAAGGAGAA     960|
|GGAGGAGTTC|CGCGTGAACA|TCCTGCCGAC|CCTGAGCAAC|ACCTTCAGCA|ACCCGAACTA    1020|
|CGCCAAGGTG|AAGGGCAGCG|ACGAGGACGC|CAAGATGATC|GTGGAGGCTA|AGCCGGGCCA    1080|
|CGCGTTGATC|GGCTTCGAGA|TCAGCAACGA|CAGCATCACC|GTGCTGAAGG|TGTACGAGGC    1140|
|CAAGCTGAAG|CAGAACTACC|AGGTGGACAA|GGACAGCTTG|AGCGAGGTGA|TCTACGGCGA    1200|
|CATGGACAAG|CTGCTGTGTC|CGGACCAGAG|CGAGCAAATC|TACTACACCA|CAACATCGT     1260|
|GTTCCCGAAC|GAGTACGTGA|TCACCAAGAT|CGACTTCACC|AAGAAGATGA|AGACCCTGCG    1320|
|CTACGAGGTG|ACCGCCAACT|TCTACGACAG|CAGCACCGGC|GAGATCGACC|TGAACAAGAA    1380|
|GAAGGTGGAG|AGCAGCGAGG|CCGAGTACCG|CACCCTGAGC|GCGAACGACG|ACGGCGTCTA    1440|
|CATGCCACTG|GGCGTGATCA|GCGAGACCTT|CCTGACCCCG|ATCAACGGCT|TGGCCTGCA     1500|
|GGCCGACGAG|AACAGCCGCC|TGATCACCCT|GACCTGTAAG|AGCTACCTGC|GCGAGCTGCT    1560|
|GCTAGCCACC|GACCTGAGCA|ACAAGGAGAC|CAAGCTGATC|GTGCCACCGA|GCGGCTTCAT    1620|
|CAGCAACATC|GTGGAGAACG|GCAGCATCGA|GGAGGACAAC|CTGGAGCCGT|GGAAGGCCAA    1680|
|CAACAAGAAC|GCCTACGTGG|ACCACACCGG|CGGCGTGAAC|GGCACCAAGG|CCCTGTACGT    1740|
|GCACAAGGAC|GGCGGCATCA|GCCAGTTCAT|CGGCGACAAG|CTGAAGCCGA|AGACCGAGTA    1800|
|CGTGATCCAG|TACACCGTGA|AGGGCAAGCC|ATCGATTCAC|CTGAAGGACG|AGAACACCGG    1860|
|CTACATCCAC|TACGAGGACA|CCAACAACAA|CCTGGAGGAC|TACCAGACCA|TCAACAAGCG    1920|
|CTTCACCACC|GGCACCGACC|TGAAGGGCGT|GTACCTGATC|CTGAAGAGCC|AGAACGGCGA    1980|
|CGAGGCCTGG|GGCGACAACT|TCATCATCCT|GGAGATCAGC|CCGAGCGAGA|AGCTGCTGAG    2040|
|CCCGGAGCTG|ATCAACACCA|ACAACTGGAC|CAGCACCGGC|AGCACCAACA|TCAGCGGCAA    2100|
|CACCCTGACC|CTGTACCAGG|GCGGCCGCGG|CATCCTGAAG|CAGAACCTGC|AGCTGGACAG    2160|
|CTTCAGCACC|TACCGCGTGT|ACTTCAGCGT|GAGCGGCGAC|GCCAACGTGC|GCATCCGCAA    2220|
|CAGCCGCGAG|GTGCTGTTCG|AGAAGAGGTA|CATGAGCGGC|GCCAAGGACG|TGAGCGAGAT    2280|
|GTTCACCACC|AAGTTCGAGA|AGGACAACTT|CTACATCGAG|CTGAGCCAGG|GCAACAACCT    2340|
|GTACGGCGGC|CCGATCGTGC|ACTTCTACGA|CGTGAGCATC|AAGTTAACGT|AGAGCTCAGA    2400|
|TCT| | | | |    2403|

( 2 ) INFORMATION FOR SEQ ID NO:8:

( i ) SEQUENCE CHARACTERISTICS:
        ( A ) LENGTH: 1638 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..1191
        ( D ) OTHER INFORMATION: /product="Translation of cDNA
            encoding VIP3A(a) receptor"

( x i ) SEQUENCE DESCRIPTION: SEQ ID NO:8:

```
T  AGT  GGA  TCC  CCC  GGG  CTG  CAG  GAA  TTC  GCG  GCC  GCG  TCG  ACC  ATG        46
   Ser  Gly  Ser  Pro  Gly  Leu  Gln  Glu  Phe  Ala  Ala  Ala  Ser  Thr  Met
    1              5                        10                       15

TAC  TCT  AGA  ATA  TTT  TTC  CTC  CTT  GTG  ATA  GTG  TGT  GCT  GTT  AAG  GCT       94
Tyr  Ser  Arg  Ile  Phe  Phe  Leu  Leu  Val  Ile  Val  Cys  Ala  Val  Lys  Ala
```

-continued

|  |  |  |  | 20 |  |  |  | 25 |  |  |  | 30 |  |  |  |  |
|---|---|---|---|---|---|---|---|---|---|---|---|---|---|---|---|---|
| TCT | CTG | TTT | ACT | GTA | AAT | GTG | TAT | GAT | GAT | AAC | CCC | GAA | ACT | GAA | ATT | 142 |
| Ser | Leu | Phe | Thr | Val | Asn | Val | Tyr | Asp | Asp | Asn | Pro | Glu | Thr | Glu | Ile | |
|  |  |  | 35 |  |  |  | 40 |  |  |  |  | 45 |  |  |  | |
| GCG | AGT | AGT | CTA | AAA | GGC | TGT | AAC | CCC | CAA | GAG | TGT | GAC | CAG | CGG | TGT | 190 |
| Ala | Ser | Ser | Leu | Lys | Gly | Cys | Asn | Pro | Gln | Glu | Cys | Asp | Gln | Arg | Cys | |
|  |  | 50 |  |  |  | 55 |  |  |  |  | 60 |  |  |  |  | |
| CGT | AGA | CTG | AAG | TTT | CCC | GGT | GGC | GCC | TGT | GTC | AAT | GGT | CGC | TGC | AAG | 238 |
| Arg | Arg | Leu | Lys | Phe | Pro | Gly | Gly | Ala | Cys | Val | Asn | Gly | Arg | Cys | Lys | |
|  | 65 |  |  |  |  | 70 |  |  |  |  | 75 |  |  |  |  | |
| TGT | GAC | AAC | TTC | CTC | AGT | GTA | AAA | GAT | GAC | GTG | TCT | GTT | GAA | GAG | CCT | 286 |
| Cys | Asp | Asn | Phe | Leu | Ser | Val | Lys | Asp | Asp | Val | Ser | Val | Glu | Glu | Pro | |
| 80 |  |  |  |  | 85 |  |  |  |  | 90 |  |  |  |  | 95 | |
| GCG | ATT | CTC | AAA | GAT | TTG | GTG | TCA | TTA | GAA | GCT | GAA | CAG | GCA | GCG | AAA | 334 |
| Ala | Ile | Leu | Lys | Asp | Leu | Val | Ser | Leu | Glu | Ala | Glu | Gln | Ala | Ala | Lys | |
|  |  |  |  | 100 |  |  |  |  | 105 |  |  |  |  | 110 |  | |
| AGT | AGA | TGC | AGA | AAC | AGA | GTG | TGT | GAC | GCG | GTG | TGC | CGT | GCC | CTA | CAC | 382 |
| Ser | Arg | Cys | Arg | Asn | Arg | Val | Cys | Asp | Ala | Val | Cys | Arg | Ala | Leu | His | |
|  |  |  | 115 |  |  |  |  | 120 |  |  |  |  | 125 |  |  | |
| AAC | ACC | AGT | GGT | GCC | TGT | GTT | GAT | GGA | CAA | TGC | AAG | TGT | ACT | AAT | AAG | 430 |
| Asn | Thr | Ser | Gly | Ala | Cys | Val | Asp | Gly | Gln | Cys | Lys | Cys | Thr | Asn | Lys | |
|  |  | 130 |  |  |  |  | 135 |  |  |  |  | 140 |  |  |  | |
| ATC | AGT | GCA | GGA | GAT | ATT | GTG | TCT | GAT | CCT | GCT | GAA | TCG | CTA | CGC | ACT | 478 |
| Ile | Ser | Ala | Gly | Asp | Ile | Val | Ser | Asp | Pro | Ala | Glu | Ser | Leu | Arg | Thr | |
|  | 145 |  |  |  |  | 150 |  |  |  |  | 155 |  |  |  |  | |
| TGT | AAC | CCT | ATA | AGG | TGT | GAC | GAA | CAA | TGT | AGA | AGA | AAT | GGC | CAT | GAA | 526 |
| Cys | Asn | Pro | Ile | Arg | Cys | Asp | Glu | Gln | Cys | Arg | Arg | Asn | Gly | His | Glu | |
| 160 |  |  |  |  | 165 |  |  |  |  | 170 |  |  |  |  | 175 | |
| TTT | GGT | GTT | TGC | TTC | AAA | GGA | CAA | TGC | AAG | TGT | GAT | TAC | TTC | CTC | AAG | 574 |
| Phe | Gly | Val | Cys | Phe | Lys | Gly | Gln | Cys | Lys | Cys | Asp | Tyr | Phe | Leu | Lys | |
|  |  |  |  | 180 |  |  |  |  | 185 |  |  |  |  | 190 |  | |
| GAA | GAA | GTC | GAT | GAA | CCT | GAA | GTT | ACA | AGC | CTT | CCA | AAA | AAC | TGC | AAC | 622 |
| Glu | Glu | Val | Asp | Glu | Pro | Glu | Val | Thr | Ser | Leu | Pro | Lys | Asn | Cys | Asn | |
|  |  |  | 195 |  |  |  |  | 200 |  |  |  |  | 205 |  |  | |
| CCC | CAA | GAG | TGT | GAC | CAG | CGT | TGT | CGT | AGA | CTG | AAG | TTC | CCC | GGT | GGC | 670 |
| Pro | Gln | Glu | Cys | Asp | Gln | Arg | Cys | Arg | Arg | Leu | Lys | Phe | Pro | Gly | Gly | |
|  |  | 210 |  |  |  |  | 215 |  |  |  |  | 220 |  |  |  | |
| GCC | TGT | GTC | AAC | GGG | CGC | TGC | AAG | TGT | GAC | AAC | TTC | TTC | AGT | GCA | GGA | 718 |
| Ala | Cys | Val | Asn | Gly | Arg | Cys | Lys | Cys | Asp | Asn | Phe | Phe | Ser | Ala | Gly | |
|  | 225 |  |  |  |  | 230 |  |  |  |  | 235 |  |  |  |  | |
| GAT | ATT | GTG | TCT | GAT | CCT | GCC | GAA | TCG | CTA | CGC | TCT | TGT | AAC | CCT | ATA | 766 |
| Asp | Ile | Val | Ser | Asp | Pro | Ala | Glu | Ser | Leu | Arg | Ser | Cys | Asn | Pro | Ile | |
| 240 |  |  |  |  | 245 |  |  |  |  | 250 |  |  |  |  | 255 | |
| AGG | TGT | GAC | GAA | CAA | TGT | AGA | AGA | AAT | GGC | CAT | GAA | TTT | GGT | GTT | TGC | 814 |
| Arg | Cys | Asp | Glu | Gln | Cys | Arg | Arg | Asn | Gly | His | Glu | Phe | Gly | Val | Cys | |
|  |  |  |  | 260 |  |  |  |  | 265 |  |  |  |  | 270 |  | |
| TTC | AAA | GGA | CAA | TGC | AAG | TGT | GAT | TAC | TTC | CTC | AAC | TCA | GAA | GTA | GAC | 862 |
| Phe | Lys | Gly | Gln | Cys | Lys | Cys | Asp | Tyr | Phe | Leu | Asn | Ser | Glu | Val | Asp | |
|  |  |  | 275 |  |  |  |  | 280 |  |  |  |  | 285 |  |  | |
| GCT | GTT | AAT | GAG | TTT | CCT | CAA | GCG | GGC | TCA | AAA | CGC | TAC | TGC | AAC | TTA | 910 |
| Ala | Val | Asn | Glu | Phe | Pro | Gln | Ala | Gly | Ser | Lys | Arg | Tyr | Cys | Asn | Leu | |
|  |  | 290 |  |  |  |  | 295 |  |  |  |  | 300 |  |  |  | |
| ACG | CAA | TGC | AAC | CAG | ACG | TGC | GCC | AAT | CGT | TTC | TAT | GAT | AGT | GCT | AGA | 958 |
| Thr | Gln | Cys | Asn | Gln | Thr | Cys | Ala | Asn | Arg | Phe | Tyr | Asp | Ser | Ala | Arg | |
|  | 305 |  |  |  |  | 310 |  |  |  |  | 315 |  |  |  |  | |
| GTG | ATC | CAC | GGC | TGG | TGC | AAA | TGC | TAC | AGT | AAG | ATG | GAA | AGA | CAG | GAT | 1006 |
| Val | Ile | His | Gly | Trp | Cys | Lys | Cys | Tyr | Ser | Lys | Met | Glu | Arg | Gln | Asp | |
| 320 |  |  |  |  | 325 |  |  |  |  | 330 |  |  |  |  | 335 | |
| GCA | TCT | CCA | TTA | AAC | GAT | GTG | ACT | GAG | GAT | GAA | AAT | GAA | GTT | TCT | AAC | 1054 |
| Ala | Ser | Pro | Leu | Asn | Asp | Val | Thr | Glu | Asp | Glu | Asn | Glu | Val | Ser | Asn | |

-continued

```
                  340                           345                           350
GAT ATC CTG AGG ACT GTT GCA GAG GAG CTG TCT GAT GTG TCA CCT AGG         1102
Asp Ile Leu Arg Thr Val Ala Glu Glu Leu Ser Asp Val Ser Pro Arg
            355                           360                       365

GCC TGC AAA TCA GCG AGC TGC AAT CAA GCA TGT CGC GCC TTC TAC TTT         1150
Ala Cys Lys Ser Ala Ser Cys Asn Gln Ala Cys Arg Ala Phe Tyr Phe
            370                           375                       380

AAA GGA GGG TGG TGT CGC TTT GGA CGA TGC CAA TGC TTC TA                  1191
Lys Gly Gly Trp Cys Arg Phe Gly Arg Cys Gln Cys Phe
            385                           390                   395

AAATTAGTAT GATATATGAA TTTTGTATTA TTCGGTTAAT TGTGTTATGT TTAAAAAACA       1251

TAATGTCTTC ATTTTAGAAA AAAGTACCTT CACTAAAGCG CAACAATTAA CTAGTAGTTA       1311

ATTATTAACT AGTAGTTAAA TTATTGATGA TTATGATTAT CTTAGTAGTA GTTAATTATA       1371

ATCATCAACT ATTAACTAGT AGTTAATTAT TAACTAGTAG TTAAATTATT GATGATTATG       1431

ATTATCTTAG TAGTAGTTAA TTATTGTTTC TTATAATAAT CTAGTATGTT GGTAGGTACT       1491

TAATAATAAC GCTTCTGACA AAAATTTAA AATTAAATAA TTCTATCAAA CATAAATAAT        1551

AACTGAAATA AAAATTTATA AGAGAAAAAA AAAAGTCGA CGCGGCCGCG AATTCGATAT        1611

CAAGCTTATC GATACCGTCG ACCTCGA                                           1638
```

( 2 ) INFORMATION FOR SEQ ID NO:9:

( i ) SEQUENCE CHARACTERISTICS:
  ( A ) LENGTH: 396 amino acids
  ( B ) TYPE: amino acid
  ( D ) TOPOLOGY: linear ( i i ) MOLECULE TYPE: protein ( x i ) SEQUENCE DESCRIPTION: SEQ ID NO:9:

```
Ser Gly Ser Pro Gly Leu Gln Glu Phe Ala Ala Ala Ser Thr Met Tyr
 1               5                  10                      15

Ser Arg Ile Phe Phe Leu Leu Val Ile Val Cys Ala Val Lys Ala Ser
                20                  25                  30

Leu Phe Thr Val Asn Val Tyr Asp Asp Asn Pro Glu Thr Glu Ile Ala
            35                  40                  45

Ser Ser Leu Lys Gly Cys Asn Pro Gln Glu Cys Asp Gln Arg Cys Arg
 50                  55                  60

Arg Leu Lys Phe Pro Gly Gly Ala Cys Val Asn Gly Arg Cys Lys Cys
 65                  70                  75                  80

Asp Asn Phe Leu Ser Val Lys Asp Asp Val Ser Val Glu Glu Pro Ala
                85                  90                  95

Ile Leu Lys Asp Leu Val Ser Leu Glu Ala Glu Gln Ala Ala Lys Ser
            100                 105                 110

Arg Cys Arg Asn Arg Val Cys Asp Ala Val Cys Arg Ala Leu His Asn
            115                 120                 125

Thr Ser Gly Ala Cys Val Asp Gly Gln Cys Lys Cys Thr Asn Lys Ile
130                 135                 140

Ser Ala Gly Asp Ile Val Ser Asp Pro Ala Glu Ser Leu Arg Thr Cys
145                 150                 155                 160

Asn Pro Ile Arg Cys Asp Glu Gln Cys Arg Arg Asn Gly His Glu Phe
                165                 170                 175

Gly Val Cys Phe Lys Gly Gln Cys Lys Cys Asp Tyr Phe Leu Lys Glu
            180                 185                 190

Glu Val Asp Glu Pro Glu Val Thr Ser Leu Pro Lys Asn Cys Asn Pro
            195                 200                 205
```

| | | | | | | | | | | | | | |
|---|---|---|---|---|---|---|---|---|---|---|---|---|---|
| Gln | Glu | Cys | Asp | Gln | Arg | Cys | Arg | Arg | Leu | Lys | Phe | Pro | Gly Gly Ala |
| | 210 | | | | 215 | | | | | | 220 | | |
| Cys | Val | Asn | Gly | Arg | Cys | Lys | Cys | Asp | Asn | Phe | Phe | Ser | Ala Gly Asp |
| 225 | | | | | 230 | | | | | 235 | | | 240 |
| Ile | Val | Ser | Asp | Pro | Ala | Glu | Ser | Leu | Arg | Ser | Cys | Asn | Pro Ile Arg |
| | | | | 245 | | | | | 250 | | | | 255 |
| Cys | Asp | Glu | Gln | Cys | Arg | Arg | Asn | Gly | His | Glu | Phe | Gly | Val Cys Phe |
| | | | 260 | | | | | 265 | | | | 270 | |
| Lys | Gly | Gln | Cys | Lys | Cys | Asp | Tyr | Phe | Leu | Asn | Ser | Glu | Val Asp Ala |
| | | 275 | | | | | 280 | | | | | 285 | |
| Val | Asn | Glu | Phe | Pro | Gln | Ala | Gly | Ser | Lys | Arg | Tyr | Cys | Asn Leu Thr |
| | 290 | | | | | 295 | | | | | 300 | | |
| Gln | Cys | Asn | Gln | Thr | Cys | Ala | Asn | Arg | Phe | Tyr | Asp | Ser | Ala Arg Val |
| 305 | | | | | 310 | | | | | 315 | | | 320 |
| Ile | His | Gly | Trp | Cys | Lys | Cys | Tyr | Ser | Lys | Met | Glu | Arg | Gln Asp Ala |
| | | | | 325 | | | | | 330 | | | | 335 |
| Ser | Pro | Leu | Asn | Asp | Val | Thr | Glu | Asp | Glu | Asn | Glu | Val | Ser Asn Asp |
| | | | 340 | | | | | 345 | | | | 350 | |
| Ile | Leu | Arg | Thr | Val | Ala | Glu | Glu | Leu | Ser | Asp | Val | Ser | Pro Arg Ala |
| | | 355 | | | | | 360 | | | | | 365 | |
| Cys | Lys | Ser | Ala | Ser | Cys | Asn | Gln | Ala | Cys | Arg | Ala | Phe | Tyr Phe Lys |
| | 370 | | | | | 375 | | | | | 380 | | |
| Gly | Gly | Trp | Cys | Arg | Phe | Gly | Arg | Cys | Gln | Cys | Phe | | |
| 385 | | | | | 390 | | | | | 395 | | | |

( 2 ) INFORMATION FOR SEQ ID NO:10:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Bacillus thuringiensis
        ( B ) STRAIN: AB88

( i x ) FEATURE:
        ( A ) NAME/KEY: Peptide
        ( B ) LOCATION: 1..14
        ( D ) OTHER INFORMATION: /note= "N-terminal amino acid
            sequence of protein known as anion exchange fraction 23
            ( s m a l l e r )"

( x i ) SEQUENCE DESCRIPTION: SEQ ID NO:10:

Xaa Glu Pro Phe Val Ser Ala Xaa Xaa Xaa Gln Xaa Xaa Xaa
    1                 5                           1 0

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: Bacillus thuringiensis ( x i ) SEQUENCE DESCRIPTION: SEQ ID NO:11:

Xaa  Glu  Tyr  Glu  Asn  Val  Glu  Pro  Phe  Val  Ser  Ala  Xaa
1                 5                              10

( 2 ) INFORMATION FOR SEQ ID NO:12:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: Bacillus thurigiensis ( x i ) SEQUENCE DESCRIPTION: SEQ ID NO:12:

Met  Asn  Lys  Asn  Asn  Thr  Lys  Leu  Pro  Thr  Arg  Ala  Leu  Pro
1                 5                              10

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Bacillus thuringiensis
        ( B ) STRAIN: AB88

( i x ) FEATURE:
        ( A ) NAME/KEY: Peptide
        ( B ) LOCATION: 1..15
        ( D ) OTHER INFORMATION: /note= "N-terminal amino acid
            sequence of 35 kDa VIP active against Agrotis ipsilon"

( x i ) SEQUENCE DESCRIPTION: SEQ ID NO:13:

Ala  Leu  Ser  Glu  Asn  Thr  Gly  Lys  Asp  Gly  Gly  Tyr  Ile  Val  Pro
1                 5                              10                             15

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: Bacillus thuringiensis ( x i ) SEQUENCE DESCRIPTION: SEQ ID NO:14:

Met  Asp  Asn  Asn  Pro  Asn  Ile  Asn  Glu
1                 5

( 2 ) INFORMATION FOR SEQ ID NO:15:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( i x ) FEATURE:
    ( A ) NAME/KEY: Peptide
    ( B ) LOCATION: 1..9
    ( D ) OTHER INFORMATION: /note= "N-terminal sequence of 80
        kDa delta- endotoxin"

( x i ) SEQUENCE DESCRIPTION: SEQ ID NO:15:

Met Asp Asn Asn Pro Asn Ile Asn Glu
1               5

( 2 ) INFORMATION FOR SEQ ID NO:16:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
    ( A ) ORGANISM: Bacillus thuringiensis ( i x ) FEATURE:
    ( A ) NAME/KEY: Peptide
    ( B ) LOCATION: 1..11
    ( D ) OTHER INFORMATION: /note= "N-terminal sequence from 60
        kDa delta- endotoxin"

( x i ) SEQUENCE DESCRIPTION: SEQ ID NO:16:

Met Asn Val Leu Asn Ser Gly Arg Thr Thr Ile
1               5                   10

( 2 ) INFORMATION FOR SEQ ID NO:17:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer sequence"

( i i i ) HYPOTHETICAL: NO ( x i ) SEQUENCE DESCRIPTION: SEQ ID NO:17:

CGATTAATGT TGGCCTC                                        17

( 2 ) INFORMATION FOR SEQ ID NO:18:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer sequence"

( i i i ) HYPOTHETICAL: NO ( x i ) SEQUENCE DESCRIPTION: SEQ ID NO:18:

CATTAGCATC TCCGGACACA G                                    21

( 2 ) INFORMATION FOR SEQ ID NO:19:

( i ) SEQUENCE CHARACTERISTICS:
( A ) LENGTH: 2370 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA encoding VIP3A(b)"

( i i i ) HYPOTHETICAL: NO ( x i ) SEQUENCE DESCRIPTION: SEQ ID NO:19:

```
ATGAACAAGA ACAACACCAA GCTGAGCACC CGCGCCCTGC CGAGCTTCAT CGACTACTTC     60
AACGGCATCT ACGGCTTCGC CACCGGCATC AAGGACATCA TGAACATGAT CTTCAAGACC    120
GACACCGGCG GCGACCTGAC CCTGGACGAG ATCCTGAAGA ACCAGCAGCT GCTGAACGAC    180
ATCAGCGGCA AGCTGGACGG CGTGAACGGC AGCCTGAACG ACCTGATCGC CCAGGGCAAC    240
CTGAACACCG AGCTGAGCAA GGAGATCCTT AAGATCGCCA ACGAGCAGAA CCAGGTGCTG    300
AACGACGTGA ACAACAAGCT GGACGCCATC AACACCATGC TGCGCGTGTA CCTGCCGAAG    360
ATCACCAGCA TGCTGAGCGA CGTGATGAAG CAGAACTACG CCCTGAGCCT GCAGATCGAG    420
TACCTGAGCA AGCAGCTGCA GGAGATCAGC GACAAGCTGG ACATCATCAA CGTGAACGTC    480
CTGATCAACA GCACCCTGAC CGAGATCACC CCGGCCTACC AGCGCATCAA GTACGTGAAC    540
GAGAAGTTCG AAGAGCTGAC CTTCGCCACC GAGACCAGCA GCAAGGTGAA GAAGGACGGC    600
AGCCCGGCCG ACATCCTGGA CGAGCTGACC GAGCTGACCG AGCTGGCGAA GAGCGTGACC    660
AAGAACGACG TGGACGGCTT CGAGTTCTAC CTGAACACCT TCCACGACGT GATGGTGGGC    720
AACAACCTGT TCGGCCGCAG CGCCCTGAAG ACCGCCAGCG AGCTGATCAC CAAGGAGAAC    780
GTGAAGACCA GCGGCAGCGA GGTGGGCAAC GTGTACAACT TCCTGATCGT GCTGACCGCC    840
CTGCAGGCCA AGGCCTTCCT GACCCTGACC CCCTGTCGCA AGCTGCTGGG CCTGGCCGAC    900
ATCGACTACA CCAGCATCAT GAACGAGCAC TTGAACAAGG AGAAGGAGGA GTTCCGCGTG    960
AACATCCTGC CGACCCTGAG CAACACCTTC AGCAACCCGA ACTACGCCAA GGTGAAGGGC   1020
AGCGACGAGG ACGCCAAGAT GATCGTGGAG GCTAAGCCGG GCCACGCGTT GATCGGCTTC   1080
GAGATCAGCA ACGACAGCAT CACCGTGCTG AAGGTGTACG AGGCCAAGCT GAAGCAGAAC   1140
TACCAGGTGG ACAAGGACAG CTTGAGCGAG GTGATCTACG GCGACATGGA CAAGCTGCTG   1200
TGTCCGGACC AGAGCGGGCA AATCTACTAC ACCAACAACA TCGTGTTCCC GAACGAGTAC   1260
GTGATCACCA AGATCGACTT CACCAAGAAG ATGAAGACCC TGCGCTACGA GGTGACCGCC   1320
AACTTCTACG ACAGCAGCAC CGGCGAGATC GACCTGAACA AGAAGAAGGT GGAGAGCAGC   1380
GAGGCCGAGT ACCGCACCCT GAGCGCGAAC GACGACGGCG TCTACATGCC ACTGGGCGTG   1440
ATCAGCGAGA CCTTCCTGAC CCCGATCAAC GGCTTTGGCC TGCAGGCCGA CGAGAACAGC   1500
CGCCTGATCA CCCTGACCTG TAAGAGCTAC CTGCGCGAGC TGCTGCTAGC CACCGACCTG   1560
AGCAACAAGG AGACCAAGCT GATCGTGCCA CCGAGCGGCT TCATCAGCAA CATCGTGGAG   1620
AACGGCAGCA TCGAGGAGGA CAACCTGGAG CCGTGGAAGG CCAACAACAA GAACGCCTAC   1680
GTGGACCACA CCGGCGGCGT GAACGGCACC AAGGCCCTGT ACGTGCACAA GGACGGCGGC   1740
ATCAGCCAGT TCATCGGCGA CAAGCTGAAG CCGAAGACCG AGTACGTGAT CCAGTACACC   1800
GTGAAGGGCA AGCCATCGAT TCACCTGAAG GACGAGAACA CCGGCTACAT CCACTACGAG   1860
GACACCAACA ACAACCTGGA GGACTACCAG ACCATCAACA AGCGCTTCAC CACCGGCACC   1920
```

| | | | | | |
|---|---|---|---|---|---|
| GACCTGAAGG | GCGTGTACCT | GATCCTGAAG | AGCCAGAACG | GCGACGAGGC | CTGGGGCGAC | 1980
| AACTTCATCA | TCCTGGAGAT | CAGCCCGAGC | GAGAAGCTGC | TGAGCCCGGA | GCTGATCAAC | 2040
| ACCAACAACT | GGACCAGCAC | CGGCAGCACC | AACATCAGCG | GCAACACCCT | GACCCTGTAC | 2100
| CAGGGCGGCC | GCGGCATCCT | GAAGCAGAAC | CTGCAGCTGG | ACAGCTTCAG | CACCTACCGC | 2160
| GTGTACTTCA | GCGTGAGCGG | CGACGCCAAC | GTGCGCATCC | GCAACTCCCG | CGAGGTGCTG | 2220
| TTCAAGAAGA | GGTACATGAG | CGGCGCCAAG | GACGTGAGCG | AGATGTTCAC | CACCAAGTTC | 2280
| GAGAAGGACA | ACTTCTACAT | CGAGCTGAGC | CAGGGCAACA | ACCTGTACGG | CGGCCCGATC | 2340
| GTGCACTTCT | ACGACGTGAG | CATCAAGTAG | | | | 2370

( 2 ) INFORMATION FOR SEQ ID NO:20:

( i ) SEQUENCE CHARACTERISTICS:
        ( A ) LENGTH: 2241 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA encoding
            VIP3A(c)"

( i i i ) HYPOTHETICAL: NO ( x i ) SEQUENCE DESCRIPTION: SEQ ID NO:20:

| | | | | | |
|---|---|---|---|---|---|
| ATGAACAAGA | ACAACGCCAA | GCTGAGCACC | CGCGCCCTGC | CGAGCTTCAT | CGACTACTTC | 60
| AACGGCATCT | ACGGCTTCGC | CACCGGCATC | AAGGACATCA | TGAACATGAT | CTTCAAGACC | 120
| GACACCGGCG | GCGACCTGGC | CCTGGACGAG | ATCCTGGAGA | ACCAGCAGCT | GCTGAACGAC | 180
| ATCAGCGGCA | AGCTGGACGG | CGTGAACGGC | AGCCTGAACG | ACCTGATCGC | CCAGGGCAAC | 240
| CTGAACACCG | AGCTGAGCAA | GGAGATCCTT | AAGATCGCCA | ACGAGCAGAA | CCAGGTGCTG | 300
| AACGACGTGA | ACAACAAGCT | GGACGCCATC | AACACCATGC | TGCGCGTGTA | CCTGCCGAAG | 360
| ATCACCAGCA | TGCTGAGCGA | CGTGATGAAG | CAGAACTACG | CCCTGAGCCT | GCAGATCGAG | 420
| TACCTGAGCA | AGCAGCTGCA | GGAGATCAGC | GACAAGCTGG | ACATCATCAA | CGTGAACGTC | 480
| CTGATCAACA | GCACCCTGAC | CGAGATCACC | CCGGCCTACC | AGCGCATCAA | GTACGTGAAC | 540
| GAGAAGTTCG | AAGAGCTGAC | CTTCGCCACC | GAGACCAGCA | GCAAGGTGAA | GAAGGACGGC | 600
| AGCCCGGCCG | ACATCCGGGA | CGAGCTGAGC | GAGCTGACCG | AGCTGGCGAA | GAGCGTGACC | 660
| CAGAACGACG | TGGACGGCTT | CGAGTTCTAC | CTGAACACCT | TCCACGACGT | GATGGTGGGC | 720
| AACAACCTGT | TCGGCCGCAG | CGCCCTGAAG | ACCGCCAGCG | AGCTGATCAC | CAAGGAGAAC | 780
| GTGAAGACCA | GCGGCAGCGA | GGTGGGCAAC | GTGTACAACT | TCCTGATCGT | GCTGACCGCC | 840
| CTGCAGGCCC | AGGCCTTCCT | GACCCTGACC | CCCTGTCGCA | AGCTGCTGGG | CCTGGCCGAC | 900
| ATCGACTACA | CCAGCATCAT | GAACGAGCAC | TTGAACAAGG | AGAAGGAGGA | GTTCCGCGTG | 960
| AACATCCTGC | CGACCCTGAG | CAACACCTTC | AGCAACCCGA | ACTACGCCAA | GGTGAAGGGC | 1020
| AGCGACGAGG | ACGCCAAGAT | GATCGTGGAG | GCTAAGCCGG | GCCACGCGTT | GATCGGCTTC | 1080
| GAGATCAGCA | ACGACAGCAT | CACCGTGCTG | AAGGTGTACG | AGGCCAAGCT | GAAGCAGAAC | 1140
| TACCAGGTGG | ACAAGGACAG | CTTGAGCGAG | GTGATCTACG | GCGACATGGA | CAAGCTGCTG | 1200
| TGTCCGGACC | AGAGCGGGCA | AATCTACTAC | ACCAACAACA | TCGTGTTCCC | GAACGAGTAC | 1260
| GTGATCACCA | AGATCGACTT | CACCAAGAAG | ATGAAGACCC | TGCGCTACGA | GGTGACCGCC | 1320
| AACTTCTACG | ACAGCAGCAC | CGGCGAGATC | GACCTGAACA | AGAAGAAGGT | GGAGAGCAGC | 1380

-continued

| | | | | | | | |
|---|---|---|---|---|---|---|---|
| GAGGCCGAGT | ACCGCACCCT | GAGCGCGAAC | GACGACGGCG | TCTACATGCC | ACTGGGCGTG | | 1440 |
| ATCAGCGAGA | CCTTCCTGAC | CCCGATCAAC | GGCTTTGGCC | TGCAGGCCGA | CGAGAACAGC | | 1500 |
| CGCCTGATCA | CCCTGACCTG | TAAGAGCTAC | CTGCGCGAGC | TGCTGCTAGC | CACCGACCTG | | 1560 |
| AGCAACAAGG | AGACCAAGCT | GATCGTGCCA | CCGAGCGGCT | TCATCAGCAA | CATCGTGGAG | | 1620 |
| AACGGCAGCA | TCGAGGAGGA | CAACCTGGAG | CCGTGGAAGG | CCAACAACAA | GAACGCCTAC | | 1680 |
| GTGGACCACA | CCGGCGGCGT | GAACGGCACC | AAGGCCCTGT | ACGTGCACAA | GGACGGCGGC | | 1740 |
| ATCAGCCAGT | TCATCGGCGA | CAAGCTGAAG | CCGAAGACCG | AGTACGTGAT | CCAGTACACC | | 1800 |
| GTGAAGGGCA | AGCCATCGAT | TCACCTGAAG | GACGAGAACA | CCGGCTACAT | CCACTACGAG | | 1860 |
| GACACCAACA | ACAACCTGGA | GGACTACCAG | ACCATCAACA | AGCGCTTCAC | CACCGGCACC | | 1920 |
| GACCTGAAGG | GCGTGTACCT | GATCCTGAAG | AGCCAGAACG | GCGACGAGGC | CTGGGGCGAC | | 1980 |
| AACTTCATCA | TCCTGGAGAT | CAGCCCGAGC | GAGAAGCTGC | TGAGCCCGGA | GCTGATCAAC | | 2040 |
| ACCAACAACT | GGACCAGCAC | CGGCAGCACC | AACATCAGCG | GCAACACCCT | GACCCTGTAC | | 2100 |
| CAGGGCGGCC | GCGGCATCCT | GAAGCAGAAC | CTGCAGCTGG | ACAGCTTCAG | CACCTACCGC | | 2160 |
| GTGTACTTCA | GCGTGAGCGG | CGACGCCAAC | GTGCGCATCC | GCAACTCCCG | CGAGGTGCTG | | 2220 |
| TTCGAGAAGA | AGGACAAGTA | G | | | | | 2241 |